United States Patent
Acevedo et al.

(10) Patent No.: US 7,489,397 B2
(45) Date of Patent: Feb. 10, 2009

(54) INSTRUMENT, SYSTEM AND METHOD FOR AUTOMATED LOW COST ATMOSPHERIC MEASUREMENTS

(75) Inventors: Miguel Felipe Acevedo, Carrollton, TX (US); William T. Waller, Argyle, TX (US); Gilbert B. Nebgen, Saint Jo, TX (US)

(73) Assignee: University of North Texas, Denton, TX (US)

( * ) Notice: Subject to any disclaimer, the term of this patent is extended or adjusted under 35 U.S.C. 154(b) by 289 days.

(21) Appl. No.: 11/432,084

(22) Filed: May 11, 2006

(65) Prior Publication Data

US 2006/0266950 A1    Nov. 30, 2006

Related U.S. Application Data

(60) Provisional application No. 60/679,933, filed on May 11, 2005.

(51) Int. Cl.
*G01J 3/28* (2006.01)
(52) U.S. Cl. .............................. 356/326; 356/51; 356/72; 356/73; 250/339.05
(58) Field of Classification Search .................... 356/51, 356/72, 73, 326, 328; 250/339.05, 339.07, 250/339.13, 203.4, 372, 373
See application file for complete search history.

(56) References Cited

U.S. PATENT DOCUMENTS

| 3,868,186 A | 2/1975 | Paukert et al. |
| 4,867,563 A | 9/1989 | Wurm et al. |
| 2002/0191192 A1 | 12/2002 | Patzwald et al. |

OTHER PUBLICATIONS

Ulrich Kempfer, Measurement of atmospheric ozone of differential absorption of solar radiation using a compact optical spectrometer, Jul. 2000, Society of Photo-Optical Instrumentation Engineers, vol. 39 No.7, pp. 1989.*

(Continued)

*Primary Examiner*—Kara E Geisel
*Assistant Examiner*—Abdullahi Nur
(74) *Attorney, Agent, or Firm*—Jackson Walker L.L.P.

(57) ABSTRACT

An apparatus and method for measuring ozone in the atmosphere. The apparatus utilizes a fiber optic cable connected to a collimating lens located outdoors and a spectrometer that is located indoors. A pan-and-tilt positioning unit having a pan-axis capable of tracking an azimuth angle of the Sun, and a tilt-axis capable of tracking an elevation angle of the Sun, is utilized for automatically pointing the collimating lens directly at the Sun and taking readings for column ozone determination on any given day of the year. The apparatus and method utilizes a computer that is in electrical communication with the spectrometer and the pan-and-tilt unit.

21 Claims, 12 Drawing Sheets

OTHER PUBLICATIONS

Andrady Al, Hamid SH, Hu X, Torikai A. Effects of increased solar ultraviolet radiation on materials. J Photochem Photobiol B. Oct. 1998;46(1-3):96-103.

Aric-Defra. Ozone Depletion Fact Sheet Series for Key Stage 4 and A-Level. Web site accessed 2005. http://www.ace.mmu.ac.uk/Resources/Fact_Sheets/Key_Stage_4/Ozone_Depletion/index.html.

Bigelow D.S., Slusser J.R., Beaubien A.F., Gibson J.H. 1998. The USDA Ultraviolet Radiation Monitoring Program. Bull. Am. Metero. Soc. 79:601-615.

Bojkov R.D., Fioletov V.E. 1995. Estimating the Global Ozone Characteristics During the Last 30 Years. J. Geophys. Res. 100:16 537-551 (Abstract Only).

Bramstedt K., Gleason J., Loyola D., Thomas W., Bracher A., Weber M., Burrows J.P. 2002. Comparison of Total Ozone from the Satellite Instruments GOME and TOMS with Measurements from the Dobson Network 1996-2000. Atmos. Chem. Phys. Discuss. 2:1131-1157.

Caldwell M.M., Bjorn L.O., Bornman J.F., Flint S.D., Kulandaivelu G., Teramura A.H., Tevini M. 1998. Effects of Increased Solar Ultraviolet Radiation on Terestrial Ecosystems. J. Photochem. Photobiol. 46:40-52.

Farman J.C., Gardiner B.G., Shanklin J.D. 1985. Large Losses of Total Ozone in Antarctica Reveal Seasonal ClOx/NOx Interaction. Nature. 315:207-210.

Gao W., Youfey Z., Slusser J.R., He Y., Ronggang Z. 2003. Impact of Enhanced Ultraviolet B Irradiance on Maize Yield Formation and Structure: A Field Evaluation. Proceedings of the SPIE. Ultraviolet Ground and Space Based Measurements, Models and Effects III. 396-402. (Abstract Only).

Gonzalez R., Mepsted R., Wellburn A.R., Paul N.D. 1998. Non-Photosynthetic Mechanisms of Growth Reduction in Pea (Pisum Sativum L.) Exposed to UV-B Radiation. Plant, Cell and Environment. 21:23-32.

Hader D.P., Kumar H.D., Smith R.C. Worrest R.C. 1998. Effects on Aquatic Ecosystems. J. Photochem. Photobiol. 46:53-68.

Hartwig, M. 1994. Ultraviolet and Your Health. Currents in Science, Technology and Society, 3:11-12, 16.

Kaufman J.J., Dubovik O., Smirnov A., Holben B.N. 2002. Remote Sensing of Non-Aerosol Absorption in Cloud Free Atmosphere. Geophysical Research Letters 29(18):1857.

Kohler U. 1999. A Comparison of the New Filter Ozonometer MICROTOPS II with Dobson and Brewer Spectrometers at Hohenpeissenberg. Geophysical Research Letters. 26(10):1385-1388.

Midgley G.F., Wand S.J.E., Musil C.F. 1998. Repeated Exposure to Enhanced UV-B Radiation in Successive Generations Increases Developmental Instability (Leaf Fluctuating Asymmetry) in a Desert Annual. Plant, Cell and Environment. 21:437-442.

Molina L.T., Molina M.J. 1986. Absolute Absorption Cross Sections of Ozone in the 185-to 350-nm Wavelength Range. J. Geophys. Res. 91(D13):14501-14508.

Molina M.J., and Rowland F.S. 1974. Stratospheric Sink for Chlorofluoromethanes: Chlorine Atom-Catalysed Destruction of Ozone. Nature. 249:810-812. (Abstract Only).

Morys M., Mims F.M. III, Anderson S.E. 1996. Design, Calibration and Performance of MICROTOPS II Hand-Held Ozonometer. 12th International Symposium on Photobiology. Vienna, Austria.

NOAA-SRRB 2005b. General Solar Position Calculations.

Ocean Optics 2000. Operating Manual and User's Guide S2000 Miniature Fiber Optic Spectrometers and Accessories. Dunedin, Florida: Ocean Optics Inc.

Santee M.L., Read W.G., Waters J.W., Froidevaux L., Manney G.L., Flower D.A., Jarnot R.F., Harwood R.S., Peckham G.E. 1995. Interhemispheric Differences in Polar Stratospheric $HNO_e$, $H_2O$, ClO and $O_3$. Science. 267-849-853. (Abstract Only).

Slusser, J.R., Gibson J.H., Bigelow D.S., Kolinski D., Disterhoft P., Lantz K., Beaubien A. 2000. Lanagley Method of Calibrating UV Filter Radiometers. J. Geophys. Res. 105:4841-4849.

Ullrich S.E. 2002. Photoimmune Suppression and Photocarcinogenesis. Frontiers in BioSciences. 7:D684-703 (Abstract Only).

Varotsos C., Tzannis C., Christodoulakis J. 2002. Contribution of the Athens University to Envisat Intercomparison of the Total Ozone Observations at Athens, Greece. Proc. of Envisat Validation Workshop. Frascati, Italy. Dec. 2002 (ESA SP-531, Aug. 2003).

Fellers T.J., Davidson M.W. 2005. Optical Microscopy Primer: Digital Imaging in Optical Microscopy. Molecular Expressions.

NASA-TOMS 2005. Total Ozone Mapping Spectrometer: Earth Probe TOMS Data and Images.

NASA-TOMS 2005. OMI: Ozone Monitoring Instrument.

NASA-TOMS 2005. Earth Probe TOMS Instrument and Satellite Information.

NASA-GSFC 2003. Stratospheric Ozone An Electronic Textbook. Ch.7, Section 4.2.

National Research Council 1993. Protecting Visibility in National Parks and Wilderness Areas. Washigton, DC. National Academy Press. Ch.4.

NOAA 2004A. U.S. Global Change Research Program. Interagency Program on Ultraviolet Radiation.

NOAA 2004B. Stratospheric Ozone: Monitoring and Research in NOAA.

NOAA 2004B. Solar Backscatter Ultraviolet Instrument (SBUV/2).

NOAA 2004B. TOVS Total Ozone: Stuff You Should Know.

NOAA-CMDL 2004. CMDL Total Ozone.

NOAA-NWS-CPC 2004. Stratospher: UV Index.

NOAA-SRRB 2005A. Surface Radiation Research Branch.

NOAA-SRRB 2005A. What is UV?

NSF 2004. National Science Foundation. Polar Programs UV Monitoring Network.

PHOTOMET 2005. Photometrics: Encyclopedia.

PHOTOMET 2005. Photometrics: Encylopedia (Signal-to-Noise Ratio).

PHOTOMET 2005. Photometrics: Encyclopedia (Binning).

USDA 2004. UV-B Monitoring and Research Program.

USEPA 2004. Ultraviolet Monitoring Program.

USEPA 2005. The Effects of Ozone Depletion.

Xue Y et al. Daytime Monitoring of Urban NO2 Column Density by Solar Spectroscopic Method. Japanese Journal of Applied Physics, Japan Society of Applied Physics, Tokyo, JP, 2000, 39(2A, part 1):622-627.

Delahaigue A et al. Design of a Sun Tracker for a Laser Heterodyne Spectrometer. Infrared Physics, UK, 1988, 28(1):1-6.

Garrison LM et al. Total Ozone Determination by Spectroradiometry in the Middle Ultraviolet. Applied Optics USA, 1979, 18(6):850-855.

Georgiev A et al. Sun Following System Adjustment at the UTFSM. Energy Conversion and Management, Elsevier Science Publishers, Oxford, GB, 2004, 45(11-12):1795-1806.

PCT International Search Report and the Written Opinion of the International Searching Authority under PCT Rule 44.1, dated Sep. 25, 2006.

\* cited by examiner

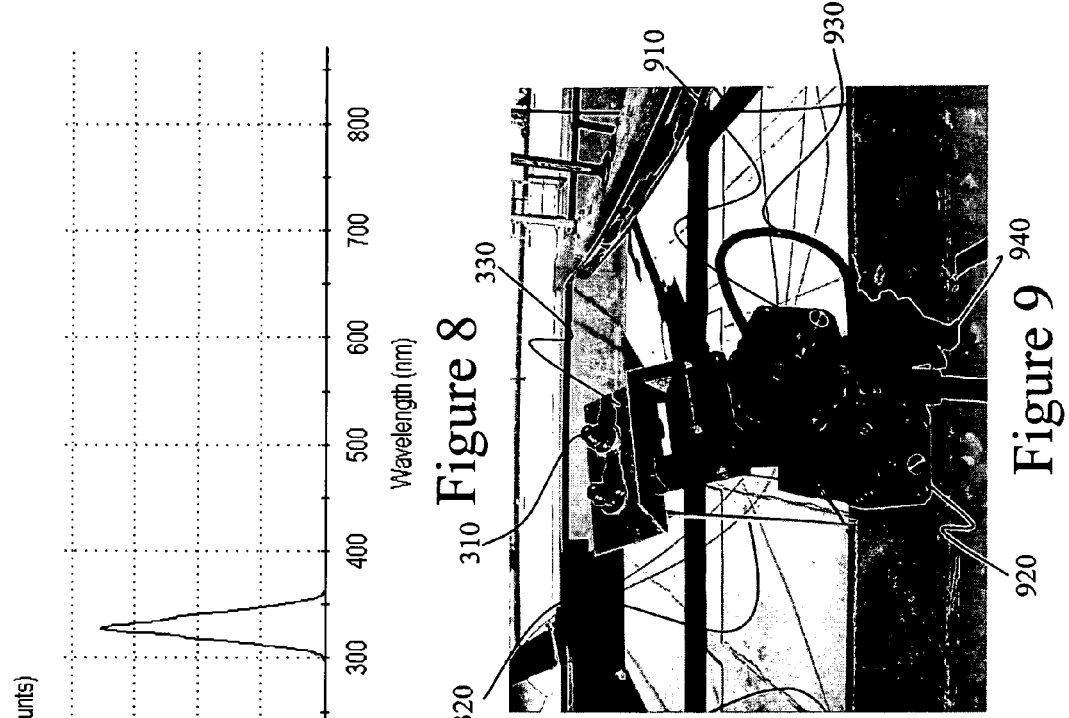
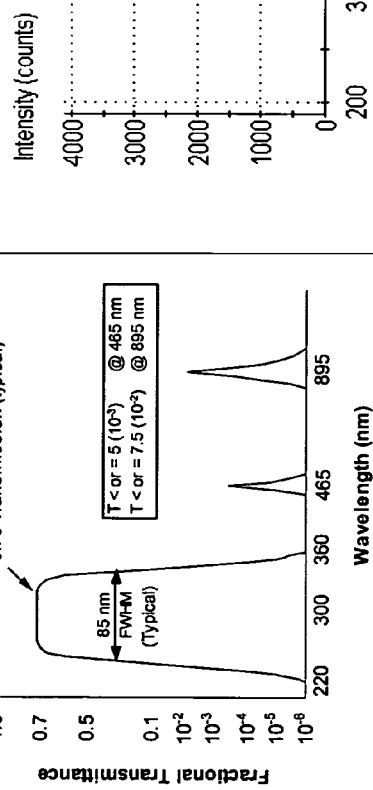
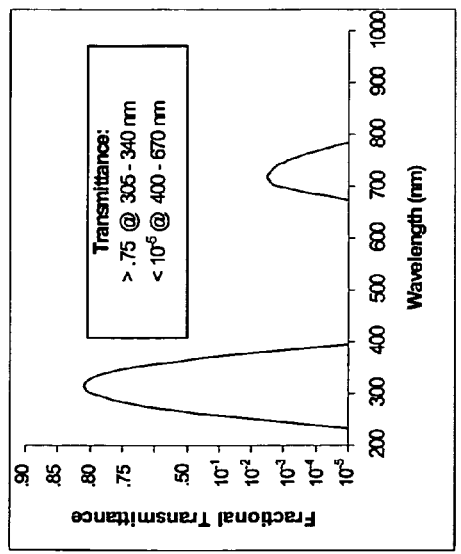

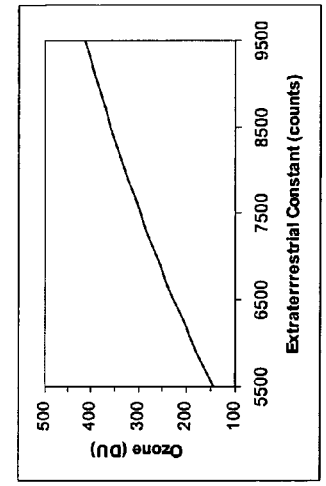
Figure 26
Figure 27
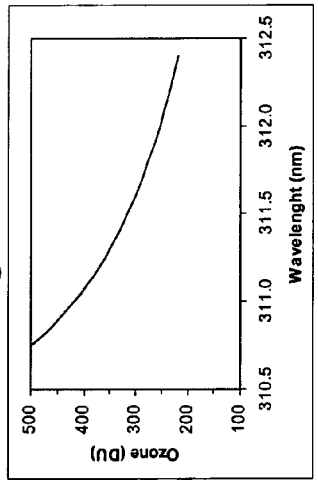
Figure 28
Figure 29
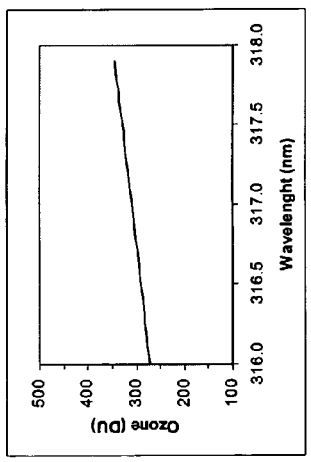
Figure 30

US 7,489,397 B2

INSTRUMENT, SYSTEM AND METHOD FOR AUTOMATED LOW COST ATMOSPHERIC MEASUREMENTS

RELATED APPLICATIONS

This application claims priority to U.S. Provisional Patent Application Ser. No. 60/679,933, entitled "Instrument, System and Method for Automated Low Cost Atmospheric Measurements" filed on May 11, 2005, having Acevedo et al., listed as the inventor(s), the entire content of which is hereby incorporated by reference.

STATEMENT OF RIGHTS TO INVENTIONS MADE UNDER FEDERALLY SPONSORED RESEARCH

No federal grants or funds were used in the development of the present invention.

BACKGROUND

This invention is related generally to an apparatus and method for measuring stratospheric ozone. More specifically, this invention is related to an instrument that employs a high-resolution fiber-optic spectrometer, coupled with precisely aimed fiber optics to acquire intensity data at multiple UV wavelengths within the UV-B range (280-320 nm). In this wavelength range, UV is attenuated by ozone, but not all is dissipated, as is the case for UV-C (100-280 mm). Although not wanting to be bound by theory, the equation used to calculate ozone incorporates the ratio of intensity for multiple wavelengths in order to eliminate interference effects from aerosols.

Life processes on earth are driven by energy which originates from the sun or has been stored from past solar radiation. The sun provides a broad spectrum of light energy, most of which is beneficial, and some of which is harmful, dependent upon exposure level. Exposure to full spectrum solar UV light, as it exists high in our atmosphere, is damaging to both biotic and abiotic entities. We therefore rely on most of this UV energy being filtered out before reaching the earth's surface. This filtering is done effectively by the earth's middle atmosphere, primarily by ozone in the stratosphere. The invention described herein is concerned with an cost effective apparatus for measuring stratospheric ozone for purposes of monitoring the Earth's UV filter.

The discovery of stratospheric ozone depletion over Antarctica provided impetus to the ozone depletion theory of Molina and Rowland and prompted the creation of networks to monitor changes in stratospheric ozone and related enhanced levels of ultraviolet radiation over the surface of the Earth, especially the biologically active UV-B. Estimates suggest that UV irradiance has increased since the early 1980s over mid- and high latitudes of both hemispheres.

Increased levels of UV have potential consequences for human health, agricultural systems, ecological systems, and material goods. Some human effects are DNA damage in cells which can lead to skin cancer, premature aging of the skin, increased risk of cataract development, and immune system repression.

Excessive UV-B has been shown to affect the physiological and developmental processes of plants. This has obvious agricultural implications for UV intolerant plant species and may necessitate the development of tolerant hybrids. The potential effects of increased levels of UV-B exposure on crops and ecosystems are not fully understood, but experiments have shown that increased UV-B exposure, especially during plant development, may induce effects such as reduction in grain yield and susceptibility to disease. Examples are reduced leaf area and DNA damage due to exposure during plant development that is not fully repaired and thus inherited by offspring and accumulated over generations, and reductions in dry matter accumulation that affect maize grain yield. Further effects of UV-B may be felt in forests and grasslands with implications on succession and biodiversity.

Recent decreases in concentration and emission rates of ozone-depleting compounds from their peak in the early 1990s indicate potential ozone recovery to pre-1980 values by the middle of the century. Observations during the 1990s indicate that ozone depletion is also occurring over the Arctic but the formation of an ozone hole similar to the one over Antarctica is unlikely. Ozone at middle latitudes has also been reduced. The average total column ozone (1997-2001) was 3% and 6% below the pre-1980 values in the Northern and the Southern Hemisphere respectively. Clearly, contributions from networks of ground-based instruments and satellite observations have greatly contributed to this understanding of ozone dynamics. Monitoring of ozone is useful while recovery of ozone occurs, due to global efforts to curb the use of products releasing chemicals harmful to the ozone layer.

Improving the spatial distribution of observing ground stations, for continued and expanded global monitoring of UV and ozone, is needed to assess current and future trends and to support satellite measurements. However, existing automatic total column ozone monitors are complex and expensive instruments. The instrument developed in this dissertation is a low-cost, yet automated, total column ozone instrument that permits the widespread distribution of monitors with potential to greatly improve our understanding of ozone dynamics.

Current Stratospheric Ozone and UV Monitoring Programs in US include the USEPA UV-Net consists of a network of 21 Brewer spectrophotometers in the United States that measure solar radiation in the LV-B and UV-A bands. Irradiance data are analyzed and disseminated to scientists and the public to assess distribution and trends of UV and long-term records for impact studies on biota and materials. Fourteen of these UV monitoring sites are located in National Parks and are operated by the National Park Service as part of the Park Research and Intensive Monitoring of Ecosystems Network ("PRIMENet"). The other seven sites correspond to urban areas. The National Ultraviolet Monitoring Center ("NUVMC") of the University of Georgia helps operate the UV-Net that is coordinated with programs of other U.S. Federal agencies through the U.S. Global Change Research Program. Total column ozone can be derived from the Brewer spectral measurements. One of ordinary skill in the art realizes that most US programs related to UV and ozone can be accessed via the UV-Net web page.

The UV Index forecast of the National Oceanic and Atmospheric Administration ("NOAA") Climate Prediction Center is a joint effort with US-EPA to produce a daily forecast of UV Index for 58 US cities as a text bulletin and in map form. It provides historical data in the form of past bulletins, monthly means and maxima and annual time series plots. NOAA's Aeronomy Laboratory ("AL"), Climate Monitoring and Diagnostics Laboratory ("CMDL"), Climate Prediction Center ("CPC") and the National Climatic Data Center ("NCDC") are involved in monitoring and research of ozone and the processes affecting its concentration in the stratosphere. CMDL maintains 15 stations based on the Dobson Ozone spectrophotometer, and is the World Dobson Ozone Calibration Center of Global Atmosphere Watch ("GAW"). This center is responsible for the calibration of about 100 instruments worldwide. Most of the ground-based total ozone instruments are part of the GAW program coordinated by the World Meteorological Organization ("WMO"). NOAA's Surface Radiation Research Branch operates the Central UV Calibration Facility ("CUCF"), the U.S. SurfRad Network of solar radiation instruments and conducts research on Uw Radiation and its effects on the earth.

In response to predictions of increased UV radiation in the polar regions, the National Science Foundation established, in 1988, the UV Monitoring Network, which currently consists of six high resolution spectroradiometers (e.g. BSI model SUV-100) located in Antarctica and other high latitude regions with a reference site in San Diego, Calif. The network perfoms measurements of global spectral irradiance in the UV and visible bands. Data are provided to researchers studying the effects of ozone depletion on terrestrial and marine biological systems.

The US Department of Agriculture ("USDA") maintains a UV-B Monitoring and Research Program initiated in 1992 to provide information on the geographical distribution and temporal trends of UV-B in the United States. This information is useful to the assessment of the potential impacts of increasing UV-B levels on crops and forests. The research network provides high resolution spectroradiometers to six selected sites.

Available Ozone Detection Instruments. The oldest ozone spectrophotometer was designed by Dobson in the 1920's, and uses prisms to select from two to six different wavelengths (between 305 and 345 nm) of the incoming light; it is still considered as the reference instrument for total ozone observations. Dobson instruments are regularly calibrated at international comparisons performed under the GAW program of WMO and related to the primary standard maintained by NOAA CMDL, Boulder, Colo.

The Brewer measures direct and global (direct+diffuse) spectral irradiance at high resolution in the wavelength range of 290-372 nm. For example, the MKIV provides spectral irradiance data in the range of 286.5 to 363 nm in steps of 0.5 nm. Total ozone is derived from direct sun measurements at four UV wavelengths. The Brewer allows automated measurements. For cloudy sky conditions, ozone may be derived from scattered UV radiation from the zenith direction. Concentration of $SO_2$ can also be derived from the instrument measurements.

The SUV-100 (Biospherical Instruments) is also high resolution (nominal bandwidth 1 nm) and is used by NSF Polar Region UV monitoring network. Based on a double monochromator and gratings, the SUV-100 is driven by a stepping motor with a step size of 0.05 nm. Other moderate resolution instruments are also used. For example the GUV 511 (Biospherical Instruments) measures UV irradiances in four channels, with center wavelengths at 305 nm, 320 nm, 340 nm and 380 nm. Bandwidths are approximately 10 m Full Width at Half Maximum ("FWHM").

The Microtops II hand-held ozonometer, manufactured by Solar Light Company, is a manual instrument which measures total column ozone and water vapor. The Microtops II is a five-channel sun-photometer with center wavelengths at 305.5, 312.5, 320, 940, and 1020 nm. The UV channels (305.5, 312.5, 320 nm) have a FWHM resolution of 2.5 nm and are used for total ozone column calculations.

Ozone Measurements from Satellites can be determined using a Total Ozone Mapping Spectrometer ("TOMS") provides data on UV and ozone. TOMS provides global distribution of ozone as well as total ozone estimates over selected sites. Backscattered radiation levels at wavelengths where ozone absorption does and does not take place are compared with the same wavelengths measured directly from the sun to derive a total ozone amount in the earth's atmosphere. This methodology is also used by NOAA's Solar Backscatter Ultraviolet ("SBUV/2") instrument. Ozone cannot be provided for the earth's shadow or polar night regions because ozone estimates are based on UV measurements. The SBUV/2 instrument currently onboard the NOAA-16 polar orbiting satellite measures the ultraviolet sunlight scattered by the Earth's atmosphere at several wavelengths ranging from 252 to 340 nm. Measurements at the shortest eight wavelengths are used to estimate ozone vertical profiles. Measurements at the longer four wavelengths, which penetrate into the lower atmosphere, are used to obtain estimates of total column ozone. It uses the ratio of two wavelengths of backscattered ultraviolet light where one is strongly absorbed by ozone while the other is absorbed very little. NOAA's TIROS Operational Vertical Sounder ("TOVS") instruments measure infrared radiation emitted by the Earth at several wavelengths instead of ultraviolet backscattered radiation. Thus, the TOVS can determine ozone at night.

Because ozone in the stratosphere is beneficial, it is often referred to as "good" ozone, compared to ozone at ground level which is frequently called "bad" ozone. Ozone in the stratosphere protects us from harmful UV, whereas ground level ozone causes respiratory problems in humans and can be deadly to plants. The apparatus and method described herein concerns the measurement of "good" ozone. Therefore, unless specified otherwise, the word ozone implies "good" ozone throughout this specification.

Ozone is a triple oxygen molecule that forms when a free oxygen atom joins with an $O_2$ molecule to form $O_3$. Both "good" and "bad" ozone have the same chemical structure, the only difference being the location in the atmosphere. The first step in ozone formation is the generation of a free oxygen atom. At ground level, the oxygen atom is produced when UV light bombards the air pollutant nitrogen dioxide, freeing one of the oxygen atoms according to the following reaction:

$$NO_2 + UV \rightarrow NO + O$$

In the stratosphere free oxygen is obtained primarily by the following reaction:

$$O_2 + UV \rightarrow O + O$$

where the UV photon energy required to split an $O_2$ molecule is much higher than that needed to separate the oxygen atom from $NO_2$. In order to split an $O_2$ molecule, the UV wavelength should be less than or equal 240 nm. Recall Planck's law $$E = h\nu$$

where E is energy, h is Planck's constant and $\nu$ is frequency, which in turn is written as the quotient of the speed of light (c) over wavelength ($\lambda$)

$$\nu = c/\lambda.$$

Thus, the shorter the wavelength, the higher the energy. Only photons with $\lambda \leq 240$ nm have enough energy to break $O_2$ bonds. Once a free oxygen atom is available, $O_3$ is formed by the reaction $$O_2 + O \rightarrow O_3.$$

In the stratosphere, the process of generating atomic oxygen by splitting $O_2$ molecules is slow due to the limited solar energy below 240 nm and, as a result, the creation of new ozone from oxygen is a slow process.

UV light is categorized as UV-A, UV-B, and UV-C dependent upon wavelength. Generally, light with a wavelength in the range 100-280 nm is considered UV-C, 280-320 nm is UV-B, and 320-400 nm is UV-A. By this definition, only UV-C has enough energy to split an $O_2$ molecule, but the total amount of UV-C available is much lower than UV-B or UV-A, resulting in a slow process for generating stratospheric ozone. The ozone layer is effective at filtering out UV-C and substantially none of it reaches the troposphere. UV-B is partially filtered by ozone whereas very little UV-A is filtered. It is therefore the biologically active UV-B with which we are primarily concerned as ozone thickness varies for any reason.

The process by which ozone absorbs and thereby attenuates harmful UV before it reaches the lower atmosphere is destruction of the ozone molecule itself. When UV light strikes an $O_3$ molecule it breaks apart into an $O_2$ molecule and an oxygen atom and the UV photon is absorbed. However, the free oxygen, usually very quickly, reacts with another $O_2$ molecule to reform $O_3$. This process of breaking and reforming $O_3$ is a fast process due to the fact that the photon energy required to break apart $O_3$ is not as high as for $O_2$ and due to the relative abundance of $O_2$. $O_3$ can be split by a photon with $\lambda \leq 325$ nm. There is an abundance of UV light in the stratosphere at these wavelengths, including some UV-A and the entire range of UV-B, and UV-C. FIG. 1 illustrates insight into the ozone creation and destruction process. Without unnatural trace gases present in the stratosphere, ozone concentration stays in balance as it is quickly destroyed by UV and then reformed. As shown in FIG. 1, some oxygen atoms escape the quick cycle by forming $O_2$ and returning to the slow process at the left of the figure (path 3), but other oxygen atoms are produced by high energy UV and these atoms reenter the fast ozone process to the right (path 1).

This cycle of ozone destruction and creation continues in a relative equilibrium fashion unless trace gases such as chlorine or bromine become more abundant and react with the free oxygen atoms, removing them from the cycle. Both chlorine and bromine found in the stratosphere are derived from man made chemicals that are transported to the stratosphere, break down, and destroy many ozone molecules.

The primary source of chlorine in the stratosphere is from the breakdown of chlorinated fluorocarbons ("CFCs") used as refrigerants, and formerly as propellants and for cleaning manufactured subassemblies. While CFCs are very stable in the troposphere and are somewhat heavier than air, they are nevertheless carried to the stratosphere by thermally driven currents called Brewer-Dobson circulation. Once CFCs reach the stratosphere, ultra-high energy UV breaks them down. This ultra-high energy UV is not present in the troposphere and CFCs are thus very stable at ground level.

Although not wanting to be bound by theory, the following reaction equations show how CFCs serve as a catalyst for ozone destruction. First, chlorine is freed from a CFC molecule (Freon-11 in this case) by a high energy UV photon and then it reacts with $O_3$ to produce chlorine monoxide. The chlorine monoxide then further consumes a free oxygen atom which would have potentially formed ozone. The net effect is that two oxygen molecules are produced from one ozone molecule and one free oxygen atom, an effective loss of two ozone molecules.

$$CFCl_3 + UV \rightarrow CFCl_2 + Cl$$
$$Cl + O_3 \rightarrow ClO + O_2$$
$$ClO + O \rightarrow Cl + O_2$$

NET: $O_3 + O \rightarrow 2 O_2$

At the end of the above set of reactions, the chlorine is still free to destroy more ozone and the cycle goes on until the chlorine atom finds another atom such as hydrogen, reacting to form HCl. At that point the damage finally ceases. It is estimated that one free chlorine atom destroys about 1000 ozone molecules before being taken out of circulation.

The apparatus and method of this invention was developed to be a substantially automated low-cost instrument to measure stratospheric ozone. Although not wanting to be bound by theory, the availability of this apparatus and method enables broader ground-based observations from repeatable positions, contributing to an expansion of UV and ozone data, and enabling a more complete mapping of ozone density. Additionally, data recorded by such instruments will support satellite observations and provide ozone data on days when satellite coverage is not available, due to satellite instrument field of view and longitudinal location of its orbit. This apparatus and method have a flexible platform, which may be adapted to study other atmospheric constituents with potential applications in a variety of ecosystem and air quality studies.

The new instrument employs a high-resolution fiber-optic spectrometer, coupled with precisely aimed fiber optics to acquire intensity data at multiple UV wavelengths within the UV-B range (280-320 nm). In this wavelength range, UV is attenuated by ozone, but not all is dissipated, as is the case for UV-C (100-280 mm). The equation used to calculate ozone incorporates the ratio of intensity for multiple wavelengths in order to substantially eliminate interference effects from aerosols. Wavelength selection was guided by past efforts such as the Dobson, Brewer, and MICROTOPS II instruments. Automation allows continuous monitoring and logging with only occasional periodic human intervention.

The invention described herein comprises:
1) A system architecture with specific system components;
2) Software algorithms used to collect and process UV-B spectral data;
3) A sun tracker based upon a two axis positioning mechanism;
4) An appropriate control method capable of integrating the entire system and developed software into a substantially automatic system;
5) Instrument calibration procedures including automated collection of Langley data;
6) The ability to calculate total column ozone using UV-B data from the spectrometer and save the intensity data and result in a file for future analysis; and
7) The ability to characterize the entire light collection subsystem including fiber optics, lenses, filters and pan and tilt mechanism;

The precision and accuracy of the instrument was determined by comparing its performance against MICROTOPS II and TOMS satellite data. The instrument's performance was evaluated to generate conclusions about the recommend methods of use for this apparatus. One of ordinary skill in the art will understand that ground based units are less expensive than satellites.

Additionally, ground based, conventional stratospheric ozone measuring instruments cost about $200,000 in 2005 U.S. dollars. The cost of these instruments greatly restricts the number that can be deployed for measuring stratospheric ozone. In contrast, the instrument, system and method of the present invention comprise a total column ozone measuring instrument which, advantageously, can be built for substantially less than a conventional instrument. The low cost of the present invention will permit expanded global monitoring of stratospheric ozone. Furthermore, the present invention is adapted to measure other trace gases and haze in the atmosphere.

SUMMARY

This invention is related generally to an apparatus and method for measuring stratospheric ozone. More specifically, this invention is related to an instrument that employs a high-resolution fiber-optic spectrometer, coupled with precisely aimed fiber optics to acquire intensity data at multiple UV wavelengths within the UV-B range. In this wavelength range, UV is attenuated by ozone, but not all is dissipated, as is the case for UV-C. The equations used to calculate ozone incorporates the ratio of intensity for multiple wavelengths in order to eliminate interference effects from aerosols.

One aspect of the current invention is an apparatus for measuring ozone in the atmosphere. The apparatus comprises (a) a fiber optic cable having a first end and a second end; (b) a collimating lens having narrow field of view coupled to the first end of the fiber optic cable, wherein light from a Sun is capable of being funneled from into the fiber-optic medium and is transmitted through the fiber optic cable, wherein the narrow field of view is in the range of about 1° to about 45°; (c) a spectrometer having a ultra-violet/visible light ("UV/VIS") channel coupled to the second end of the fiber optic cable; (d) an optical bandpass filter coupled to the fiber optic cable interposing the first end and the second end of the fiber optic cable; and (e) a pan-and-tilt positioning unit having a pan-axis capable of tracking an azimuth angle of the Sun, and a tilt-axis capable of tracking an elevation angle of the Sun, wherein pan-and-tilt positioning unit further comprises a means for mounting the collimating lens on the pan-and-tilt positioning unit. In a preferred embodiment, the means for mounting the collimating lens is an aluminum bracket with a 20° bend, however, the bracket can be made from plastic, metal, wood. Furthermore, the means for mounting the collimating lens to the positioning unit could be any type of fastener that is known in the art. The apparatus also utilizes a computer that is in electrical communication with the spectrometer and the pan-and-tilt unit. A RS232 interface is utilized by the computer to control the pan-axis and the tilt-axis via software. The fiber optic cable connects the collimating lens and the spectrometer through a barrier that separates an outdoor place from an indoor place (i.e. a rooftop of a building and a building).

In a preferred embodiment, the apparatus of this invention uses a software architecture having: a script; a mechanism control and calculation algorithm; a file storage device; and a spectrometer for communicating instructions and data. Generally, the script communicates information to the spectrometer, and the mechanism control and calculation algorithm. The spectrometer communicates information to the file storage device. The mechanism control and calculation algorithm communicates information to the file storage device. The file storage device communicates information to the script and to the mechanism control and calculation algorithm.

A second fiber optic cable having a first end and a second end can also be utilized for adding a second collimating lens that is coupled to the first end of the second fiber optic cable. The spectrometer of this invention can be equipped with a second channel for tracking a visible-light/near infra-red ("VIS/NIR") spectrum and connected to the second collimating lens. The first and second collimating lenses have a narrow field of view in the range of about 2.5°. The preferred fiber optic cable has a diameter of about 200 μm and a length up to about 20 meters. The bandpass filter of this invention is a two-stage optical bandpass filter capable of filtering wavelengths of light that are outside the range of about 260 nm to about 340 nm. The preferred spectrometer has a grating with about 1,800 lines for detecting UV/VIS in a range of about 200-350 nm; a 2048-element linear CCD array detector; a 10 um entrance slit; and optical resolution of 0.234 nm full width at half maximum ("FWHM").

The preferred pan-and-tilt positioning unit comprises a stepper motor driven mechanism capable of a 360° pan axis rotation with the tilt axis range being about 111° with a resolution of about 0.051° per half-step for each axis that corresponds to about 49 steps across an about 2.5° lens field of view. The means for mounting the collimating lens comprises an aluminum bracket having a bend angle of about 20°.

A second aspect of the current invention is a method for measuring ozone in the atmosphere. This method includes the general steps of: (a) initializing an outdoor pan-and-tilt positioning unit having a pan-axis capable of tracking an azimuth angle of a Sun, and a tilt-axis capable of tracking an elevation angle of the Sun, wherein the outdoor pan-and-tilt positioning unit comprises a mounted collimating lens that is coupled to an indoor spectrometer through a fiber optic cable, and the outdoor pan-and-tilt positioning unit is in electrical communication with a computer capable of controlling the pan-axis and the tilt-axis using software through an interface; (b) using the software for calculating the azimuth angle of the Sun and the elevation of the Sun for a date, time, and location, creating a calculated azimuth angle and a calculated elevation angle of the Sun; (c) pointing the mounted collimating lens toward the Sun by controlling the pan-axis and the tilt-axis with the computer using software through the interface, wherein mounted collimating lens is pointed toward the calculated azimuth angle and the calculated elevation angle of the Sun; (d) fine-positioning the collimating lens toward the Sun by programing a series of fine movements of the pan-axis and the tilt-axis until the light intensity striking the collimating lens has a maximum signal of about 330 nm for a filtered spectrum of sunlight having a range of about 260-340 nm; (e) gathering spectrometer data for calculating column ozone base upon Lambert-Beer-Bouguer Law, and calculating column ozone, forming a calculated column ozone value; (f) averaging the calculated column ozone value for each time step (e) is completed, forming an average column ozone value; (g) repeating step (b) at least once before recording the average column ozone value. A computer can be used for recording the average column ozone value.

The software architecture used for this method utilizes a script; a mechanism control and calculation algorithm; a file storage device; and a spectrometer for communicating instructions and data. Generally, the script communicates information to the spectrometer, and the mechanism control and calculation algorithm. The spectrometer communicates information to the file storage device. The mechanism control and calculation algorithm communicates information to the file storage device. The file storage device communicates information to the script and to the mechanism control and calculation algorithm. The method utilizes a closed loop positioning algorithm for determining the series of fine movements useful for determining the lens position where the light intensity striking the collimating lens has the maximum signal of about 330 nm for a filtered spectrum of sunlight.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6 shows a transmittance curve for solar blind filter.

FIG. 7 shows a transmittance curve for UG-11 Schott glass filter.

FIG. 8 shows a bandpass filtered solar spectrum.

FIG. 9 shows a pan and tilt mechanism in an outdoor aspect of an embodiment of the present invention.

FIG. 26 shows the sensitivity to ET 2.

FIG. 27 shows the sensitivity to ET 3.

FIG. 28 shows the sensitivity to $\lambda 1$.

FIG. 29 shows the sensitivity to $\lambda 2$.

FIG. 30 shows the sensitivity to $\lambda 3$.

DETAILED DESCRIPTION OF PREFERRED EMBODIMENTS

Figure 1:
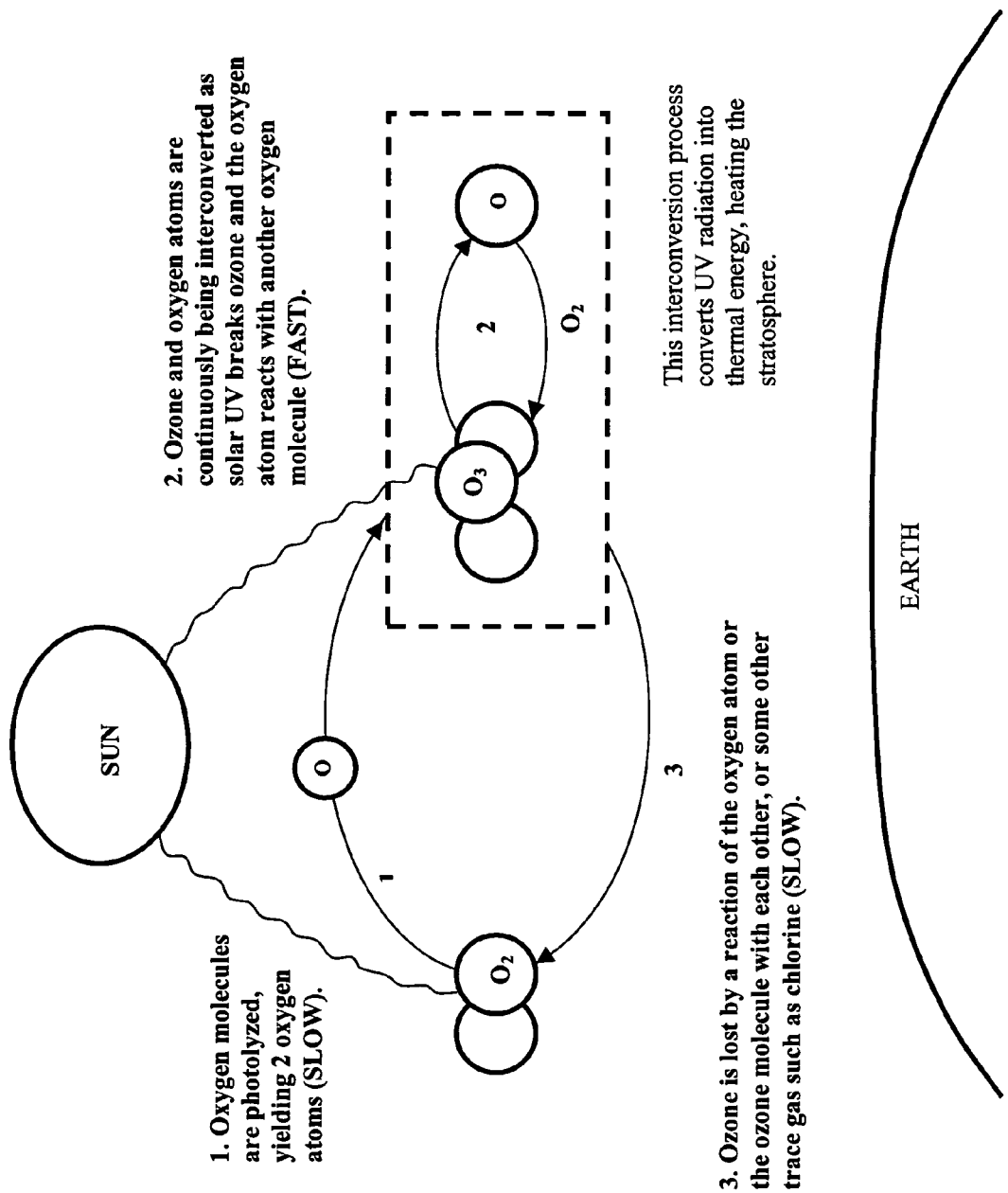
FIG. 1 shows a diagram of ozone dynamics on the Earth.

Before describing the present invention in detail, it is to be understood that this invention is not limited to particular components or component systems, which may vary. It is also to be understood that the terminology used herein is for the purpose of describing particular embodiments only, and is not intended to be limiting. In addition, before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. Additionally, when examples are given, they are intended to be exemplary only and not to be restrictive.

It should be noted that, as used in this specification and the appended claims, the singular forms "a," "an" and "the" include plural referents unless the context clearly dictates otherwise. Thus, for example, reference to "bandpass filter" may include two or more such elements, reference to "a computer" may include two or more computers, and the like.

In describing and claiming the present invention, the following terminology will be used in accordance with the definitions set out below:

The term "indoors", as used herein, includes vans, trailers, labs or any work environment in which ordinary computer equipment can be operated.

Generally, conventional automated instruments capable of measuring total column ozone comprise a spectrometer housed in a weatherproof, climate controlled enclosure placed outdoors to capture direct sunlight. By employing fiber optics to transmit sunlight indoors, the present invention enables the use of an original equipment manufacturer ("OEM") low cost spectrometer placed in a laboratory environment where there is no additional need for temperature or humidity control or weatherproofing. Furthermore, fiber optic cables, which are light weight, can be aimed at the sun with a small, inexpensive positioning device, typical of the device used to aim security cameras.

The instrument and system of the present invention is operable to transmit sunlight indoors where the devices such as the spectrometer, optical filters and controlling computer do not require expensive insulation, weatherproofing, air conditioning, or compensation.

The present invention further comprises a method to optimally aim the end of at least one fiber optic cable having light collection optics coupled to the end thereof, at the sun. The method is preferably implemented using software which is configured to run a personal computer ("PC") that drives a pan and tilt mechanism which is coupled to the fiber optic cable. The method of the present invention first calculates the position of the sun using the date and time from a PC and then uses feedback from the spectrometer to perform a series of intensity optimizing movements. At least one fiber optic cable is properly aimed at the sun when the spectrometer signal is maximized. This semi-closed loop scheme effects the relaxation of all mounting tolerances for the aiming device as well as accommodating any inaccuracy in the solar position equations. Effectively, there are no tight positional tolerances to be met since the instrument and system implementing the method uses light intensity feedback to fine position the light collection optics. The foregoing method is implemented using the instrument and system of the present invention.

The instrument, system, and method of the present invention has cost and simplicity advantages over existing instruments. The cost is less than any other automated total column ozone instrument. The low cost enables a broader group of scientists and interested users to make measurements. This in turn, results in greater coverage and resolution of ground based ozone mapping. Furthermore, setup of the present invention is less complicated than that of conventional instruments due to the closed loop positioning algorithm.

Figure 2:
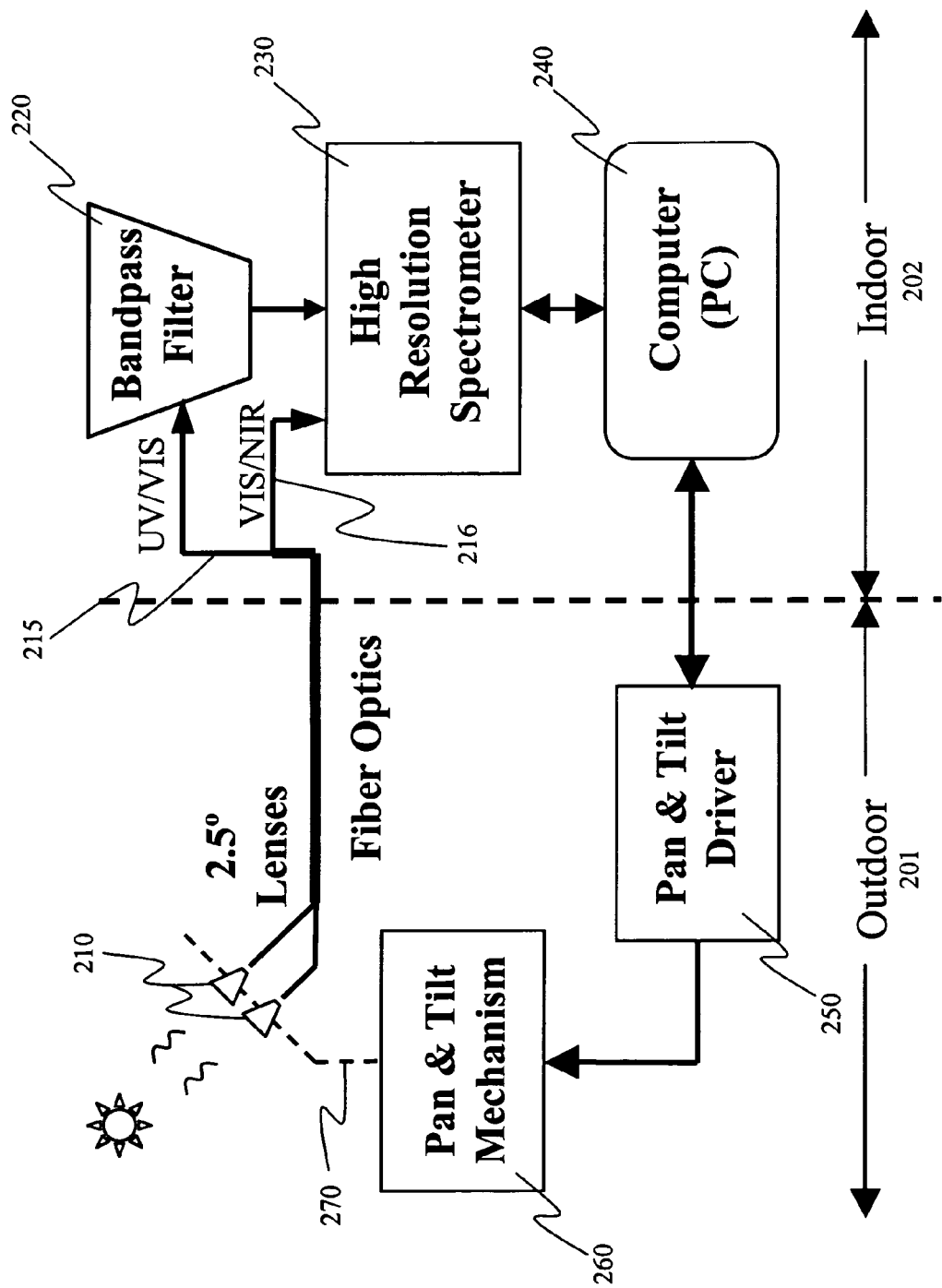
FIG. 2 shows a block diagram of both an indoor and an outdoor aspect of an apparatus in an embodiment of the present invention.

As shown in FIG. 2, the present invention comprises: a fiber-optic high-resolution spectrometer (230) receiving light from the sun via at least one fiber optic cable (215 or 216), or light filtered through a bandpass filter (220). The sunlight being channeled through light collection optics, such as lenses (210) coupled to the end thereof, aimed at the sun by a pan and tilt mechanism (260), and driven from a PC (240) via an interface card 250. The lenses (210) are mounted to the pan and tilt mechanism (260) using a bracket (270). In addition parameters other than ozone can be measured by using spectral data in various bands. This instrument and system is operational for ozone measurement, and it has been contemplated that other applications can be added. The data from the instrument and system of the present invention can be posted on an environmental education web page, such as http)://www.ecoplex.unt.edu/ where the significance of the data is explained and related to health concerns.

Although not wanting to be bound by theory, advantages of the present invention include: the instrument electronics that can be placed remotely from the light collection hardware, which minimize the need for expensive enclosures and thermal compensation, and only a simple pan and tilt device is required to move the lightweight fiber optic cables. This enables the use of a small footprint positioning mechanism to aim the light collection optics.

An exemplary embodiment of the present invention comprises a high resolution spectrometer with fiber optics, lenses, calibration lamps, PC and PC interface driving a pan and tilt mechanism. The pan and tilt mechanism is capable of aiming the fiber optic components at the sun for any daylight angle under remote control by a PC. Electronics to drive the pan and tilt mechanism can be installed on a roof in a weather proof enclosure.

The present invention further comprises software to: calculate the azimuth and elevation of the sun for the then current time and date. The software is operable to, among other things: issue commands to aim the pan and tilt mechanism at the calculated angles; enable remote fine tuning of the position of the pan and tilt mechanism in order to maximize the signal magnitude on the spectrometer; acquire UV and visible spectral data from the spectrometer, and locate a particular frequency and read its magnitude. The UV data are used to calculate the stratospheric ozone column.

Figure 20:
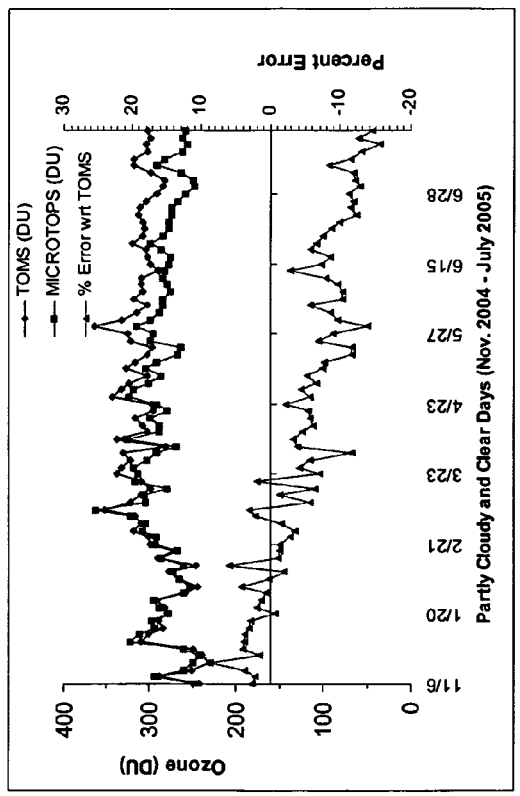
FIG. 20 shows a comparison of TOMS and MICROTOPS II.
Figure 21:
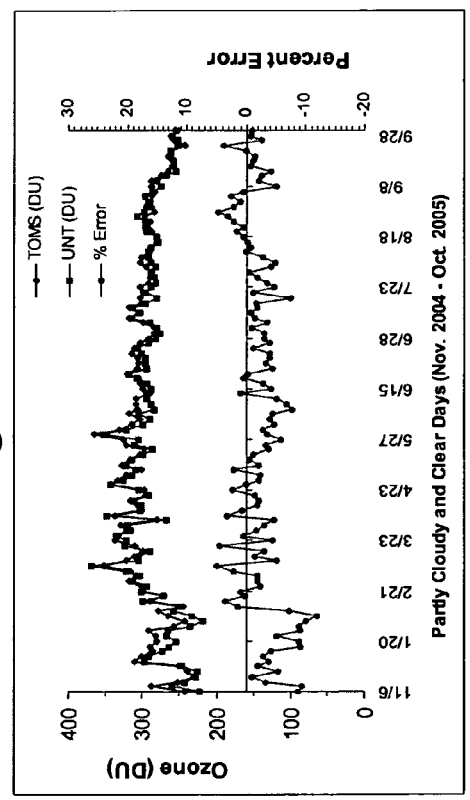
FIG. 21 shows a comparison of TOMS and UNT.
Figure 23:
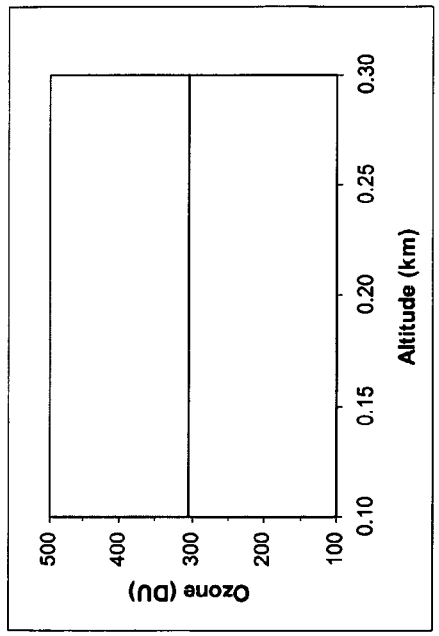
FIG. 23 shows the sensitivity to altitude.
Figure 22:
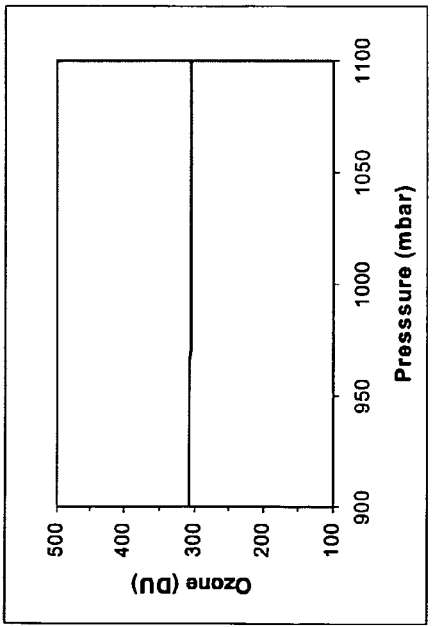
FIG. 22 shows the sensitivity to pressure.
Figure 25:
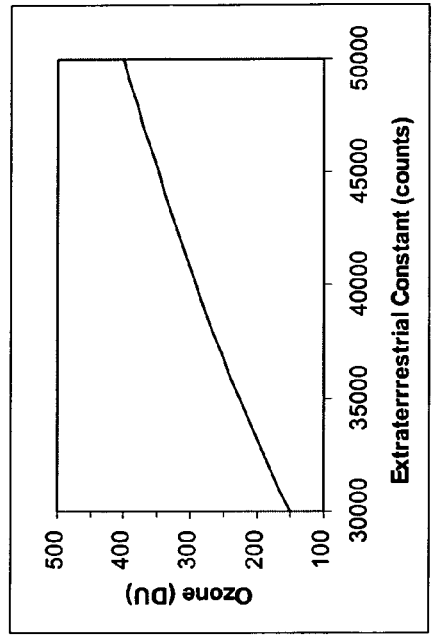
FIG. 25 shows the sensitivity to ET 1.
Figure 24:
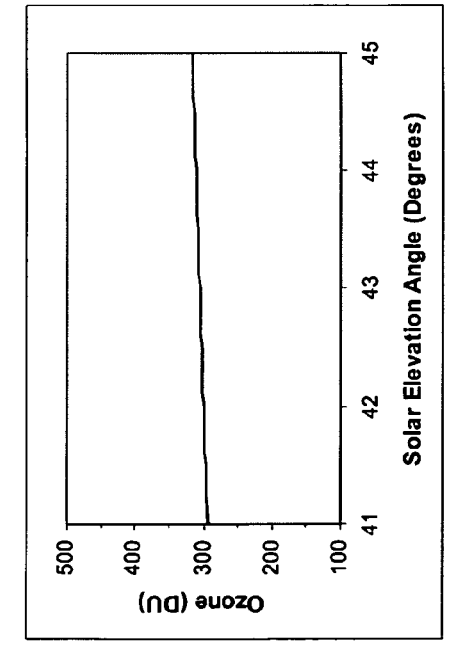
FIG. 24 shows the sensitivity to elevation angle.

FIGS. 20 and 21 show the comparison of the first data taken by the instrument of the present invention with two conventional ozone measuring instruments. The instrument labeled MICROTOPS II is a handheld manual (non-automated) instrument made by the Solar Light Company, TOMS is the Total Ozone Mapping Satellite, and the UNT system is the current invention. As seen therein, the present invention tracked the other two sources fairly well in the beginning. At the midpoint, where calibration procedures and algorithms were improved, which resulted in improved tracking.

The instrument, system and method of the present invention shown and described above is only exemplary. Even though several characteristics and advantages of the present invention have been set forth in the foregoing description together with details of the invention, the disclosure is illustrative only and changes may be made within the principles of the invention to the full extent indicated by the broad general meaning of the terms used in herein and in the attached claims.

This invention is related generally to an apparatus and method for measuring stratospheric ozone. More specifically, this invention is related to an instrument that employs a high-resolution fiber-optic spectrometer, coupled with precisely aimed fiber optics to acquire intensity data at multiple UV wavelengths within the UV-B range (280-320 nm). In this wavelength range, UV is attenuated by ozone, but not all is dissipated, as is the case for UV-C (100-280 nm). Although not wanting to be bound by theory, the equation used to calculate ozone incorporates the ratio of intensity for multiple wavelengths in order to eliminate interference effects from aerosols.

EXAMPLES

The following examples are provided to further illustrate this invention and the manner in which it may be carried out. It will be understood, however, that the specific details given in the examples have been chosen for purposes of illustration only and not be construed as limiting the invention.

Example 1

Existing ground based stratospheric ozone measuring instruments compute total column ozone from spectral data gathered by a spectrometer. The phrase "total column ozone" implies a measurement of all ozone between the sun and the earth's surface, though very little ozone is present outside the stratosphere. Total column ozone is usually expressed in Dobson Units ("DU"). To understand what a Dobson Unit is, imagine a hollow column (i.e. cylindrical or rectangular) which extends from the ground to the top of the atmosphere. This column contains the same air as the atmosphere around it at each elevation. Now, remove all atmospheric constituents from the column except for ozone. Next, imagine a piston inserted at the top of the column which is pushed down the column, compressing the ozone, until the pressure becomes 1 atmosphere. During this process the temperature in the column is held to 0° C. Finally, measure the thickness (mm) of the ozone in the column, multiply by 100, and you will have the total column ozone measured in DU. For example if the ozone thickness is measured at 3 mm, then the total column ozone is 300 DU.

Ozone absorbs UV radiation and it more efficiently dissipates shorter wavelengths. This property will be used to infer the amount of ozone between the observer and the sun by looking at the differences in UV attenuation at several wavelengths. Ozone calculations will be based on the Lambert-Beer-Bouguer ("LBB") law of light attenuation applied at specific wavelengths, $\lambda$.

The general form of the LBB Law is $$I(\lambda)=I_0(\lambda)e^{-a(\lambda)x} \quad (1)$$

where $I(\lambda)$ is the intensity of light at a given wavelength $\lambda$ after passing through a medium, $I_0(\lambda)$ is the intensity of light before passing through the medium, $a(\lambda)$ is the attenuation constant, and x is the thickness of the medium, ozone in this case.

If ozone were the only factor attenuating UV radiation, then the ozone thickness x could be determined directly by the above equation. However, other factors such as Rayleigh (molecular) and Mie (aerosol) scattering serve to attenuate UV intensity received at the earth's surface. A more accurate equation for atmospheric attenuation of UV, including all three factors, is the following:

$$I(\lambda)=I_0(\lambda)e^{-a(\lambda)x}e^{-b(\lambda)y}e^{-c(\lambda)z} \quad (2)$$

which can be simplified to $$I(\lambda)=I_0(\lambda)e^{-a(\lambda)x-b(\lambda)y-c(\lambda)z} \quad (3)$$

where:
 $a(\lambda)$=ozone attenuation constant x=ozone thickness
 $b(\lambda)$=Rayleigh scattering attenuation constant y=Rayleigh path length ratio
 $c(\lambda)$=Mie scattering attenuation constant z=Mie path length ratio Of the three atmospheric attenuators of UV included in the above equation, ozone absorption and Rayleigh scattering are fairly well understood and documented, but Mie scattering is unpredictable due to day-to-day, hour-to-hour, particulate variation. Equations exist for ozone absorption and Rayleigh scattering coefficients based upon wavelength ($\lambda$) and path length through the atmosphere, but Mie scattering is dependent upon aerosol composition and concentration. If it were not for the uncertainty of Mie attenuation, the above equation could be solved for x, and thus yield the ozone thickness directly.

Fortunately, within the UV range of interest (280-320 nm), the attenuation of UV by aerosols is only slightly wavelength dependent. The intensity ratio can thus be taken for two different values of $\lambda$, one wavelength being more strongly absorbed by ozone than the other, resulting in a cancellation of the aerosol effect. This is illustrated by simplification of the following equation, which is the ground level intensity ratio for two wavelengths.

$$\frac{I_1}{I_2} = \frac{I_{01}e^{-a_1 x - b_1 y - c_1 z}}{I_{02}e^{-a_2 x - b_2 y - c_2 z}} \quad (4)$$

(The nomenclature in this equation has been shortened: $I(\lambda)$ has been replaced by $I_\lambda$ so that $I_1$ indicates the intensity at $\lambda_1$, $a_1$ is the ozone attenuation constant at $\lambda_1$, etc.) If $\lambda_1$ and $\lambda_2$ are chosen within a few nanometers of each other, then $c_1 \approx c_2$. This allows the aerosol effect to be cancelled from the equation. Equation (4) is then simplified to $$\frac{I_1}{I_2} = \frac{I_{01}}{I_{02}} e^{(a_2 - a_1)x + (b_2 - b_1)y} \quad (5)$$

The effect of particulate scattering is thus eliminated by taking the intensity ratio of two closely spaced wavelengths.

Now, the goal is to solve the above equation for x, the total column ozone thickness. Performing the algebra yields $$x = \frac{\ln \frac{I_{01}}{I_{02}} - \ln \frac{I_1}{I_2} + (b_2 - b_1)y}{a_1 - a_2} \quad (6)$$

The variables within this equation can be measured or calculated $a_\lambda = \alpha_\lambda \mu(Z)$ $b_\lambda = \beta_\lambda$ $y = m(Z)P/P_0$ where:
- $I_{0\lambda}$=intensity of light before passing through the atmosphere
- $I_\lambda$=intensity of light at a given wavelength $\lambda$, at the Earth's surface
- $\alpha_\lambda$=absorption coefficient for ozone
- $\mu(Z)$=ratio of actual and vertical path lengths through the ozone layer
- $\beta_\lambda$=Rayleigh scattering coefficient
- $m(Z)$=ratio of actual and vertical path lengths through entire atmosphere; This ratio is called "airmass." Airmass is a function of Z, the Zenith angle and is typically calculated as $1/\cos(Z)$
- P=atmospheric pressure
- $P_0$=standard atmospheric pressure (1013.25 mb)

Parameter $\mu(Z)$ is calculated from the site elevation and latitude, as well as the height of the ozone layer and Earth's radius. $\alpha_\lambda$ and $\beta_\lambda$ are calculated from independent models proposed by Molina and Penndorf. $I_\lambda$ and P are obtained via measurement by spectrometer and barometer respectively. The only remaining unknown is the extraterrestrial light intensity $I_{0\lambda}$ which is obtained using the Langley method.

OVERVIEW OF SYSTEM ARCHITECTURE. FIG. 2 is a block diagram of the instrument. Both UV/visible and visible/NIR fiber optic cables are employed to capture and transmit light into respective channels of the high resolution spectrometer, the dashed line in FIG. 2 delineates indoor and outdoor components. Light collected from the UV/visible fiber is routed through a two-stage optical bandpass filter which passes only the band from 260-340 nm to the spectrometer so as not to exceed the stray light handling capability of the spectrometer. The 260-340 nm light is used to calculate the total column ozone. The visible/IR band is provided for applications beyond ozone.

The tip of each fiber is fitted with a narrow field of view (2.5°) collimating lens (210) to collect sunlight and focus it on the tip of the fiber optic. As shown in FIG. 2, light from both channels is transmitted to the spectrometer located indoors (230), and data collected by the spectrometer are ported to the PC (240). This computer processes the algorithm to calculate ozone and is also in charge of sending the commands to the sun targeting hardware (260).

The fiber optic lenses are aimed automatically at the sun during daylight hours by a pan and tilt ("PT") unit with fine positioning resolution. The pan motion is made to track the sun's azimuth angle, while the tilt axis tracks the sun's elevation. The PT position is remotely controlled by the PC via RS232 interface (250).

This instrument provides affordability without sacrificing reliability. This architecture gains a cost advantage over commercially available units such as the Dobson or Brewer instruments in that the spectrometer and PC are located within a controlled environment. The instrument of this invention provides a means of transmitting sunlight indoors. Because the tip of the fiber and lens are the only optical components exposed outdoors, compensation of temperature and humidity effects are greatly simplified. Controlled environmental conditions provide improved overall instrument stability and enable longer intervals between calibration. By placing the major electronics indoors, the typical need for weatherproofing and expensive thermal compensation is almost eliminated. Additional cost savings result from the fact that the pan and tilt device has a relatively light load, moving only the lightweight fiber optic cables/lenses. This enables the use of a small footprint, inexpensive, positioning mechanism, which allows the system to utilize an inexpensive spectrometer.

INSTRUMENT HARDWARE COMPONENTS. This automated total column ozone instrument has been developed using a high-resolution spectrometer system with fiber optics, lenses, optical filters, calibration lamps, and PC interface comprise the light measurement subsystem. A precision PT unit provides motion for sun tracking.

Figure 3:
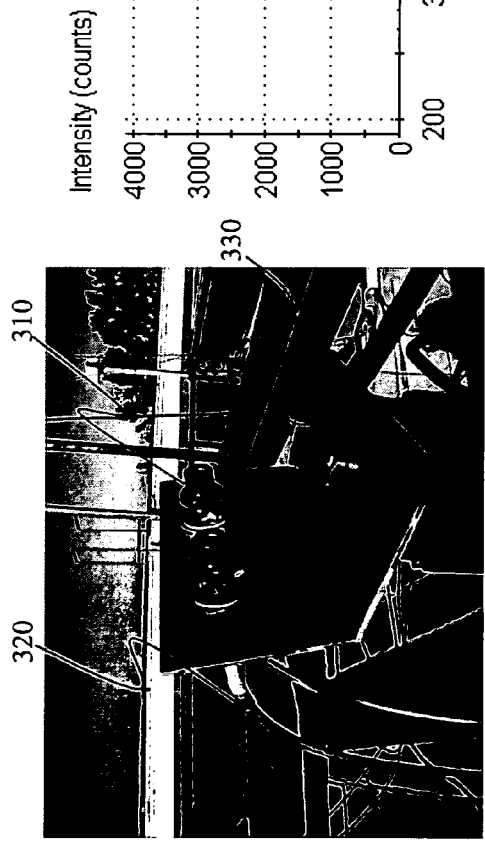
FIG. 3 shows fiber optics and lenses (light collection end) mounted to a pan and tilt mechanism in an outdoor aspect of an embodiment of the present invention.

Fiber Optics and Lenses. Sunlight was collected outdoors (e.g. on the roof of the UNT Environmental Education Science and Technology ("EESAT") building) using two narrow field of view collimating lenses coupled to fiber optic cables. The optical fibers transmit this light to the spectrometer (e.g. located in the Ecosystems Laboratory (top/3rd floor of building)). The two lenses are mounted to a 20° angle bracket bolted to the top of the PT unit (FIG. 3). One UV/visible fiber optic cable and one visible/IR fiber optic cable are attached to these collection lenses and were routed to the laboratory via an existing conduit. The UV/visible band was used to calculate ozone and the visible/IR band is for future applications of this system.

Narrow field of view lenses are employed to collect light directly from the sun and focus it on the tip of the fiber optic. This maximizes the signal transmitted to the fiber optic cable and subsequently the spectrometer. The lenses used for this purpose are Ocean Optics 74-UV collimating lenses, however, one of ordinary skill in the art will understand other lenses could be used without departing from the spirit and scope of the invention. These lenses have a field of view which is adjustable over the range ~1° to ~45°. The solar disk just fits within a 2.5° circular field of view, making this a desired beam divergence angle for the lenses.

The UV fiber optic cable used for ozone measurement is a laboratory grade, 200 um diameter, 20 m long, UV-VIS solarization resistant fiber optic cable, also from Ocean Optics (see Table 1 for fiber optic cable specifications).

TABLE 1

Fiber optic cable specs

| | |
|---|---|
| Operating wavelength: | UV-VIS or High-OH (250-800 nm) fiber<br>VIS-NIR or Ultra-low-OH (400-2100 nm) fiber<br>UV solarization-resistant (200-800 nm) fiber |
| Bare Fiber: | Pure fused-silica core, fluorine-doped silica cladding and polyimide coating |
| Fiber profile: | Step-index multimode |
| Numerical aperture: | 0.22 +/− 0.02 or 24.8° |
| Core-to-cladding ratio: | 1:1.1 (for core diameters 200 μm or greater);<br>1:2.5 (for core diameter of 50 μm) |
| Bend radius: | Momentary = 200x diameter<br>Long-term = 400x diameter | http://www.oceanoptics.com/products/fiberspecs.asp

The 20 m cable length was set for this installation by the location of the Ecosystems Laboratory within the EESAT building. A conduit was in place, which runs from the roof, where the light collection lenses are located, to the laboratory located on the 3rd floor. For other installations the optimal fiber length will vary, depending upon spectrometer proximity to an outside location with good sun exposure. Although not wanting to be bound by theory, it is beneficial to select a location that allows the fiber optic cable length to be as short as possible for two reasons: 1) to minimize signal attenuation, and 2) to minimize cost. If the fiber length must be longer than about 20 meters, then a fiber diameter larger than 200 um should be considered to reduce signal attenuation. Fiber optic diameter and spectrometer signal integration time go hand-in-hand to produce a trace intensity centered within the spectrometer's amplitude range. Larger fiber diameters transmit more light and enable shorter spectrometer integration times. The result is quicker ozone measurement time and better scan-to-scan consistency by reducing effects of atmospheric variability.

Figure 4:
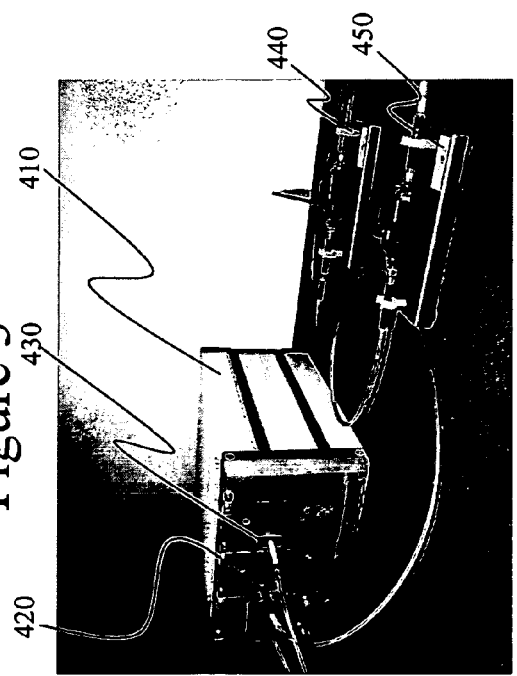
FIG. 4 shows a spectrometer and a two-stage optical bandpass filter in an indoor aspect of an embodiment of the present invention.

Spectrometer. As mentioned above, both UV/visible and visible/NIR fiber optic cables were routed to the spectrometer in the Ecosystems Laboratory. The visible/NIR cable (430) attaches directly to the spectrometer, whereas light collected from the UV/visible fiber (420) is routed through the two-stage optical band-pass filter (440/450) (FIG. 4). The spectrometer (410) shown in FIG. 4 is an Ocean Optics SD-2000-TR with one UV and one VIS channel. This spectrometer has a temperature regulated ("TR") optical bench, which allows for more stable dark readings if the spectrometer is used in an environment where the temperature varies. The temperature regulation feature is not used in this instrument for two reasons: 1) new dark readings are taken prior to collecting each set of ozone data and, 2) the laboratory temperature is regulated via thermostat. Therefore, an Ocean Optics SD-2000 would perform just as well for less cost.

TABLE 2

Spectrometer specifications

SD-2000 (UV Channel):

Grating #10: 1800 lines (200-350 nm)
2048-element linear CCD array detector
10 um entrance slit (3.2 pixel resolution)
Stray Light Rejection:

>2 × 10³ at 600 nm
>1 × 10³ at 435 nm
Signal-to-Noise:

250:1 single acquisition
750:1 average of 9 acquisitions
Optical Resolution:

0.234 nm FWHM

General spectrometer specifications for the UV channel, given in Table 2, and are briefly discussed here (Ocean Optics 2000). Grating #10 was selected along with a 10 um entrance slit to yield fine resolution in the 200-350 nm range. Optical resolution for this spectrometer is determined by the equation $$\tau_o = \frac{\psi}{\varepsilon} \times \rho \quad (7)$$

where $\tau_o$ is the optical resolution (nm), $\psi$ is spectral range (150 nm), $\varepsilon$ is the number of elements (2048 pixels) in the CCD (Charge Coupled Device) array and the 10 μm entrance slit produces a resolution, $\rho$, of 3.2 pixels (Ocean Optics, 2000). Substituting these values into Equation (7) yields $$\tau_o = \frac{150}{2048} \times 3.2 = 0.234 \text{ nm}$$

Figure 5:
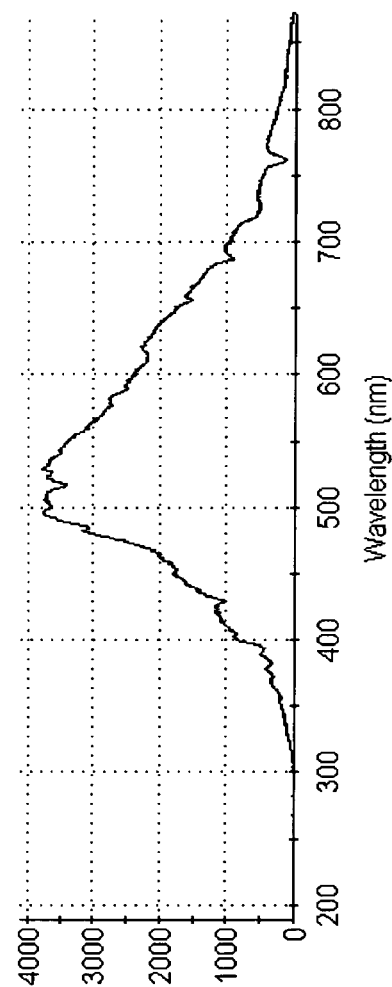
FIG. 5 shows an unfiltered UV/visible solar spectrum.

Optical Band-pass Filter and Stray Light Rejection. Light in the 305-320 nm wavelength range is used to calculate total column ozone. This presents a challenge because sunlight intensity at 500 nm is many orders of magnitude greater than that at 300 nm. For example, FIG. 5 is an unfiltered solar spectrum acquired using a spectrometer with a UV/Visible channel. Notice that the 300 nm magnitude appears to be zero by comparison to the 500 nm intensity. The 500 nm intensity is actually greater than 10⁴ times that at 300 nm.

Since the band of interest is from 305 to 320 nm, light outside that range is considered stray light and should be adequately dealt with in order not to exceed the spectrometer's stray light handling capability (see Table 2). Exceeding the spectrometer stray light spec causes cross-coupling of longer wavelength light to lower wavelength pixels on the CCD, and this results in excess and erroneous intensity for the wavelengths needed to measure ozone. Longer wavelength light should therefore be substantially attenuated prior to spectrometer entry. This was accomplished for this instrument by employing a two stage bandpass filter with elements selected to pass only the band from 260-340 nm.

A single stage filter that would adequately attenuate all frequencies outside the band of interest could also be utilized. The dual stage optical filter in this instrument is comprised of a Solar Blind SB-300-F optical filter from Corion, Division of Spectra Physics, and a Schott UG-11 optical filter purchased from Melles Griot. The input/output light path and mounting for both filters is accomplished using in-line filter holders from Ocean Optics (model # FHS-UV). The filter holders include collimating lenses and SMA (Sub-Miniature version A coaxial RF connectors) 905 terminators compatible with fiber optic cable connectors. Specifications for both filters are given in Table 3, FIG. 6, and FIG. 7.

FIG. 6 shows a percent transmittance curve for the solar blind filter. Notice the cross-over leakage peaks centered at 465 nm and 895 nm. Because of these leakage peaks, the solar blind filter, by itself, is not adequate to attenuate the high intensity sunlight present at these frequencies. The Schott glass filter was employed to provide more attenuation at the leakage peaks and thereby compliment the solar blind filter (see FIG. 7). Combining both the solar blind and Schott glass filters yields a percent transmittance of about 55% in the band of interest (305-320 nm).

The total out-of-band rejection, including the spectrometer plus both filters, is $2 \times 10^{10}$ at 465 nm and $2 \times 10^{14}$ at 600 nm. These are estimated by multiplying the spectrometer stray light rejection by the filter's out of band rejection at the appropriate wavelength as follows $$R = r \times t_1 \times t_2,$$

where R is the total out of band rejection, r is the spectrometer stray light rejection, and $t_1$ and $t_2$ are the solar blind and Schott glass filter fractional transmittances, respectively. For example, using values from Table 2 and Table 3 at 465 nm $$R = 10^3 \times 2 \times 10^2 \times 10^5$$

$$R = 2 \times 10^{10}$$

TABLE 3

| Filter specifications |
|---|
| Solar Blind SB-300-F: |
| Out of Band Rejection: |
| $2 \times 10^2$ at 465 nm |
| $1 \times 10^6$ at 600 nm |
| Transmittance: |
| 70% at 270-330 nm |
| Schott UG-11: |
| Out of Band Rejection: |
| $1 \times 10^5$ at 400-670 nm |
| Transmittance: |
| >75% at 305-340 nm |

Thus, out of band signal at 465 nm is attenuated by $2 \times 10^{10}$ and this is adequate to eliminate interference from high intensity solar emissions in this band.

FIG. 8 shows the solar spectrum filtered by this two stage bandpass filter. The spectrometer integration time was increased to raise the intensity. As can be seen, the filter provides a relatively sharp cutoff of the out-of-band frequencies. Notice particularly the negative slope in the 330-350 nm range where the full solar spectra rises sharply (see FIG. 5 also). The filter provides excellent roll-off in this range and is very adequate overall for eliminating unwanted light before it enters the spectrometer.

Each of the components in the light path attenuates the light intensity a certain amount. At least 60% of the in-band light is lost due to the combination of filters and filter holders. The fiber diameter should be sized to accommodate all of the losses and still provide enough signal. The 200 μm fiber has shown to be adequate for lengths up to 20 m.

Sun Tracking Hardware. The positioning mechanism used in this instrument is a pan and tilt (PT) unit (model PTU-46-17.5) manufactured by Directed Perception. The PT is located on the roof of the EESAT building and is shown in FIG. 9. This mechanism is presently capable of aiming the fiber optics at the sun for any daylight angle and is remotely controlled by the PC in the Ecosystems Laboratory via serial RS232 communications.

The PT is a stepper motor driven mechanism capable of 360° rotation (azimuth) with a tilt range of 111° (10° below horizon to 101° elevation with 20 degree bracket). The PT resolution is 0.051° per "halfstep" for each axis, corresponding to 49 steps across the 2.5° lens field of view in each axis (azimuth and elevation). This resolution is accomplished within the mechanism by half-stepping 1.8° stepper motors, which are gear reduced by a 17.5:1 gear ratio. Resolution ($\tau_m$) for this mechanism is calculated by the following equation.

$$\tau_m = \frac{1.8 \ [°/\text{step}]}{2 \ [\text{halfsteps/step}] \times 17.5} = 0.051 \ [°/\text{halfstep}]$$

The worst case open loop accuracy of the PT is not specified. Typical stepper motors are capable of a worst case accuracy of one halfstep. Considering drive screw accuracy/backlash as well as the motor driver current variation, the total axis subsystem accuracy may be a little worse than one halfstep. In actuality however, worst case conditions rarely apply and the overall subsystem accuracy is probably better than one halfstep. But, due to compensation afforded by the closed loop sun tracking algorithm described below, this is not a critical issue. Given closed loop positioning, the accuracy of each axis will be no worse than the axis resolution calculated above (±0.051°).

While the PT is capable of moving at speeds up to 200°/sec. (12 volt operation), it is operated only at 45°/sec. (both axes) in this application, since quick motion is not required and only adds to component stress. The acceleration for the PT is set by the ozone instrument software to 180°/sec². The velocity profiles for the PT are trapezoidal which means that, once a move is initiated, final velocity is achieved in $V_f/A$ seconds, where $V_f$ is final (e.g. maximum) velocity (°/sec.) and A is acceleration (°/sec.²). So for a 45° move, final velocity is attained in 45/180=0.25 sec. The total move time for a 45° trapezoidal move is 1.25 sec. (0.25 sec. acceleration, 0.75 sec. at final velocity, 0.25 sec. deceleration).

The payload capability for the PT far exceeds the requirements for this ozone instrument since it was designed to move cameras weighing up to 4 lbs. The total weight of the mounting bracket, lenses, and fiber optic ends for the ozone instrument is less than 0.25 lb. This light load is very helpful in obtaining good accuracy from the PT by demanding less torque and resulting in less total system backlash (stepper motor and drive screw).

The control software of the ozone instrument sets velocity, acceleration, run current, and idle current and turns off software limits for the PT before any other action is taken. Run current is set to high current, and hold (or detent) current is set to low current for both axes. Software limits are disabled in order to attain the full range of motion from the PT specified above. Turning off software limits is not an issue unless the PT is commanded beyond its usable range. In that case, without software limits, it will hit the end of travel stops and absolute position will be lost, requiring that the PT be re-homed via software command or power cycling. This has not been a problem for this instrument since azimuth and elevation angles are calculated via software, and the range of computed values are within the range of motion of the PT.

Two ~20 meter long cables are used to drive the PT mechanism, power and RS232 link. These cables were routed through the same conduit that contains the fiber optic cables. The power cable connects the PT to a 3A, 12 volt DC power supply located in the Ecosystems Lab. Both ~20 meter cables were constructed using off-the-shelf components.

The specifics of the RS232 interface to the PT are the following: 9600 baud, 1 start bit, 8 data bits, 1 stop bit, no parity, no handshaking. However, other configurations can be used.

Driver electronics which control the pan and tilt mechanism were located on the roof of EESAT in a 6"×8" weatherproof enclosure with no temperature or humidity control. The components within this controller were robust to temperature and humidity excursions, however they should be kept out of direct condensation.

In order to take full advantage of the PT tilt range, a bracket (330) was employed which has a bend angle of 20° (See FIG. 9). This enables a range of elevation angles from 100° to 11° below the horizon. The bracket (330) which is used on the current instrument was $\frac{1}{16}$" thick aluminum. This material thickness allows for ease of bending and drilling while providing adequate rigidity for stable positioning. Aluminum is a good material choice because it does not oxidize when exposed to damp conditions, and other materials could also be used.

The PT/sun tracker (910/920/930/940) was thus well suited to this application, allowing excellent centering of the solar disk within the collimating lens collection area and providing more than adequate speed and payload capability. The built-in RS232 interface makes automated control easy to establish.

Figure 10:
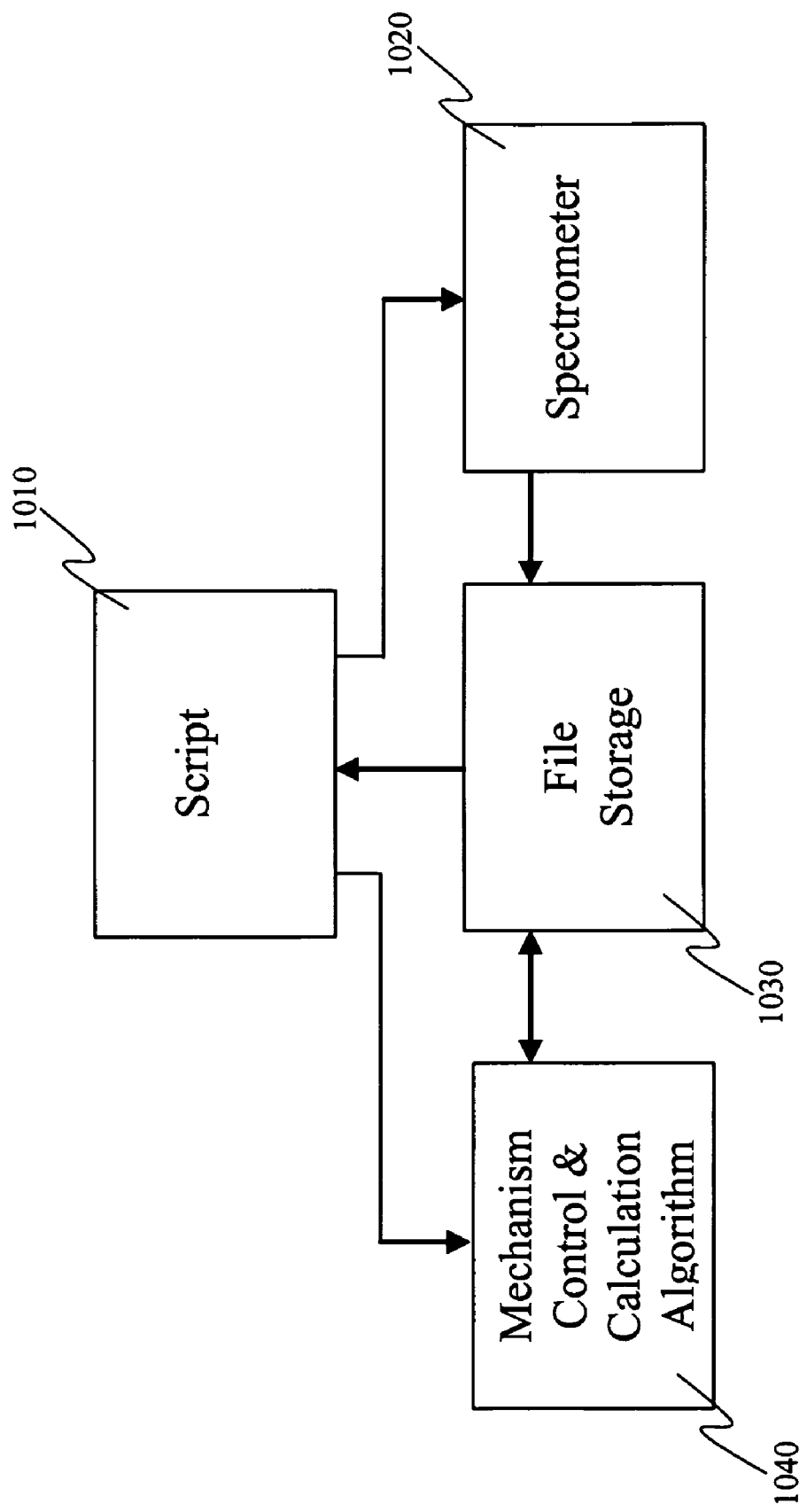
FIG. 10 shows the software hierarchy.

FIG. 10 is a hierarchical flowchart of the software which controls the ozone instrument. At the top is a script program (1010) which directs when the various instrument functions will be performed. This script is available to one of ordinary skill in the art using this section as guidance. For example, the current script program was written in a language called AutoIt, which is very adept at opening and closing windows, manipulating files, simulating keystrokes, and the like. As such this program is ideal for directing the mechanism control & calculation algorithm (1040) and the spectrometer (1020), both of which respond to keystrokes, either simulated or from the keyboard. A copy of a useful script for this purpose can be found in Appendix A in Nebgen, G., B. "AUTOMATED LOW COST INSTRUMENT FOR MEASURING TOTAL COLUMN OZONE," Dissertation, 2006, University of North Texas, Denton, Tex., the entirety of which is specifically incorporated herein by reference.

The mechanism control & calculation algorithm (1040) is a custom program responsible for sun tracking and ozone calculation. The spectrometer operating software (1020) is shipped with the spectrometer and controls all spectrometer functions. As indicated in FIG. 10, files (1030) are shared between the spectrometer (1020), the mechanism control & calculation algorithm (1040), and the script program (1010). These files contain the spectrometer data from the last scan as well as status information being passed from the mechanism control & calculation algorithm to the script program.

Figure 11:
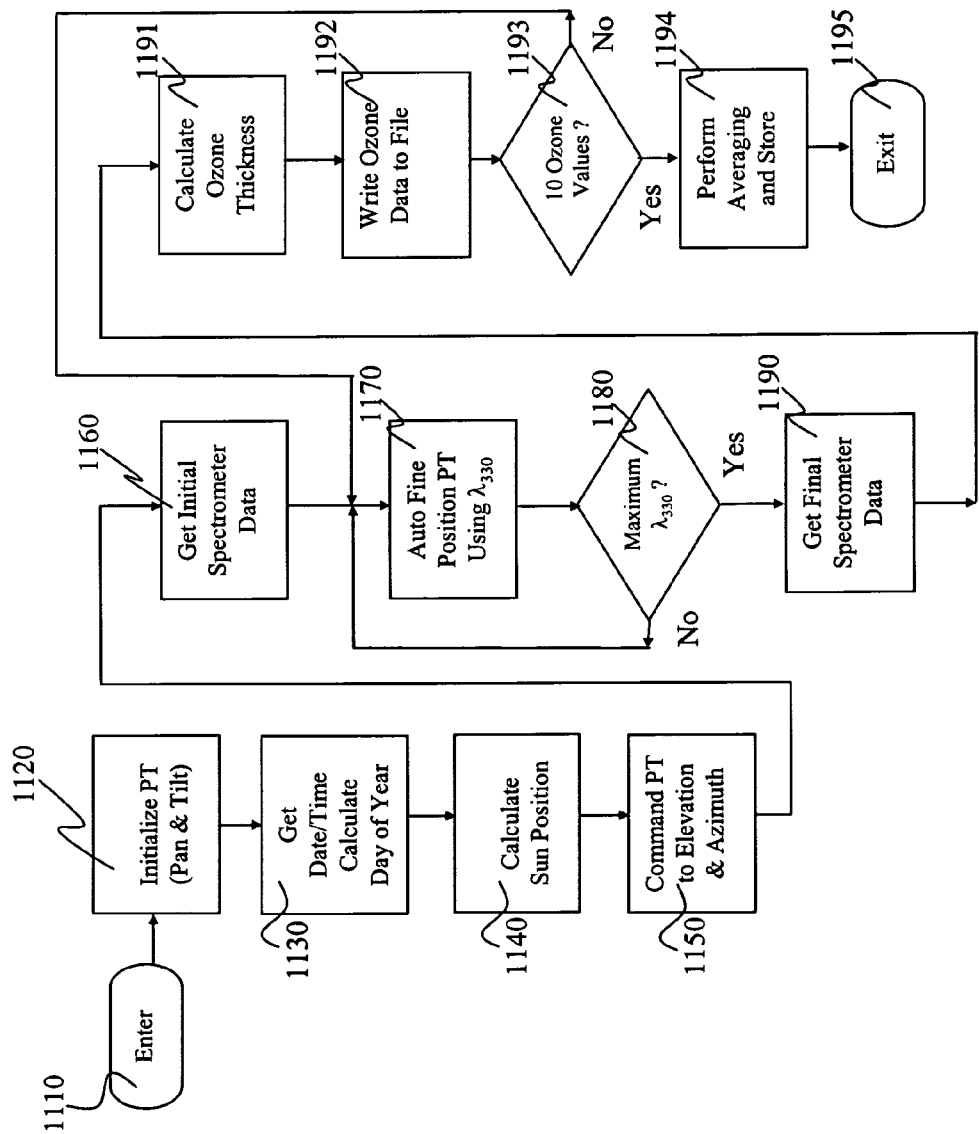
FIG. 11 shows the mechanism control and calculation algorithm flowchart.

Mechanism Control & Calculation Algorithm (1040). The mechanism control and calculation program for the current apparatus was written in QuickBASIC version 4.50. However, script is available to one of ordinary skill in the art using this section as guidance. It was designed specifically for this instrument. FIG. 11 is a block diagram for the mechanism control and calculation algorithm. This program will be hereafter referred to simply as the calculation routine, calculation program, or calculation algorithm. A copy of a useful script for this purpose can be found in Appendix B in Nebgen, G., B. "AUTOMATED LOW COST INSTRUMENT FOR MEASURING TOTAL COLUMN OZONE," Dissertation, 2006, University of North Texas, Denton, Tex.

Upon entry (1110) into the calculation routine, the Pan and Tilt ("PT") unit is initialized (1120) and sent to its home position. Initialization sets parameters such as run current, hold current, acceleration, and velocity. The PT software limits are disabled to allow full range of motion for both axes.

Once the PT is initialized, variables are dimensioned and initialized for all other modules within the program. This includes calculating $\alpha$'s and $\beta$'s (wavelength dependent attenuation constants) for the Lambert-Beer-Bouguer ("LBB") Law. After completing this, the program waits for a command from the script program to take an ozone reading.

When the script routine opens the calculation program window and issues an "o" keystroke, the calculation routine begins preparation for taking an ozone reading. The next function of the calculation routine is to read the time and date from the PC calendar and clock (1130) and utilize this information in conjunction with the local latitude and longitude to calculate the sun's azimuth and elevation angles (1140). These coordinates are used to aim the light collection lenses at the sun (1150).

Accurately pointing the lenses directly at the sun is accomplished in two stages. First, the PT unit is commanded to the calculated solar azimuth and elevation coordinates Second, fine positioning is controlled by software, using the spectrometer output to guide a series of intensity-optimizing moves. The light intensity at 330 nm is monitored on the spectrometer (1160) and a series of progressively finer moves (1170) are made with the PT until the position of maximum signal is obtained (1180). At these optimal coordinates, the solar disk is centered within the collection lens' field of view.

Equations were obtained from the NOAA Surface Radiation Research Branch ("SRRB") website which calculate solar azimuth and elevation angles, utilizing the day of year, time, time zone, and local longitude and latitude. It was necessary to make a slight correction to the azimuth equation provided on the website (Equation 15 below is the corrected equation for $\theta$). Solar azimuth and elevation angles are calculated in this instrument using the seven steps outlined here:

Step 1: Obtain fractional year in radians (e.g. how far the earth has progressed in its orbit of the sun);
Step 2: Calculate equation of time (time correction for elliptical orbit);
Step 3: Calculate solar declination angle;
Step 4: Convert local time to true solar time;
Step 5: Compute hour angle (convert true solar time into angular position of sun relative to solar noon);
Step 6: Calculate solar zenith angle; and
Step 7: Calculate solar azimuth angle.

Symbol definitions for the solar equations discussed below are given in Table 4.

TABLE 4

Symbol Definitions for Solar Equations $d$ = day of year (1-366)
$h$ = hour (24 hour basis)
$m$ = minutes
$s$ = seconds
$e_t$ = equation of time [minutes]

TABLE 4-continued

Symbol Definitions for Solar Equations $f_t$ = time offset for location in time zone [minutes]
$n_t$ = solar noon [minutes]
$s_t$ = true solar time [minutes]
$z_t$ = time zone [hours from UTC]
$\alpha$ = longitude [degrees]
$\beta$ = latitude [degrees]
$\delta$ = solar declination [radians]
$\varphi$ = solar zenith angle [degrees]
$\gamma$ = fractional year [radians]
$\theta$ = solar azimuth angle [degrees]
$\tau$ = hour angle [degrees]

Step 1: The fractional year ($\gamma$) is given by the equation $$\gamma = \frac{2\pi}{365} \times \left(d - 1 + \frac{h-12}{24}\right). \quad (8)$$

The fractional year is an angular measurement of the earth's position in its orbit around the sun. At noon on January 1 (day 1), $\gamma$ is zero, on July 1 (day 182 or 183 for leap year), $\gamma$ is about $\pi$ radians, and on December 31 it is about $2\pi$ radians. Since leap years are not accounted for by the constant 365 days used in the equation, 12 is subtracted from the hour. This gives a good overall average within the four year leap year cycle, due to the approximate 365 days and 6 hours required for the earth to orbit the sun. Subtracting 12 hours makes the fractional year a little low for the first two years of the leap year cycle and a little high for years three and four.

Step 2: The equation of time (minutes) is calculated by $e_t$=229.18×(0.000075+0.001868 cos($\gamma$)−0.032077 sin($\gamma$)−0.014615 cos(2$\gamma$)−0.040849 sin(2$\gamma$)). (9)

The equation of time yields a value which accounts for the change in the time of solar noon during the course of a year. Earth's orbit is elliptical and, based upon Kepler's law, equal areas are traversed by orbiting planets in equal times. This means that, when the earth is farther from the sun, its velocity is slower. Consequently, the equations predicting solar noon based upon an exact 24 hour day (constant velocity, e.g. circular orbit) should be corrected. The equation of time provides this correction (NOAA-SRRB 2005). Depending upon the day of year, the equation of time yields values from a minimum of about −14 minutes to a maximum of approximately +17 minutes.

Step 3: Solar declination angle is given by:

$\delta$=0.006918−0.399912 cos($\gamma$)+0.070257 sin($\gamma$)−
0.006758 cos(2$\gamma$)+0.000907 sin(2$\gamma$)−0.002697
cos(3$\gamma$)+0.00148 sin(3$\gamma$). (10)

The result is in radians. Declination is the sun's angle above or below the celestial equator (the projection of the earth's equator onto the celestial sphere).

Step 4: In order to calculate the solar zenith and azimuth angles, time should be converted to "true solar time." The following equations accomplish this. True solar time ($s_t$) is given in decimal minutes by $s_t$=60×h+m+s/60+$f_t$ (11)

where "time offset" ($f_t$) accommodates the factors which affect the time of solar noon and is computed by $f_t$=$e_t$+60×$z_t$−4×$\alpha$. (12)

Solar noon is different depending upon whether you are at the east, west or center of your time zone and this is accounted for in equation (12) along with the offset due to the equation of time ($e_t$). To account for the location within time zone, equation (12) references back to UTC (Coordinated Universal Time). The location dependent component of $f_t$ is computed in minutes by multiplying the local time zone ($z_t$) by sixty and the subtracting four times $\alpha$ (longitude). Four times $\alpha$ is subtracted because there are 4 minutes time change per degree of longitude (24 hrs=1440 minutes; 1440 minutes/ 360° longitude=4 minutes per degree of longitude).

Step 5: One more step is needed prior to calculating zenith and azimuth angles. It is necessary to convert true solar time into the angular position of the sun in degrees. The name given to this value is "solar hour angle" ($\tau$). The solar hour angle is defined as zero at solar noon, and is calculated by $\tau$=($s_t$/4)−180°. (13)

Again the 4 minute per degree longitude is used, this time to convert from time in minutes to angle in degrees.

Step 6: Finally the solar zenith angle can be calculated by the equation $\cos(\varphi)$=$\sin(\beta)\sin(\delta)$+$\cos(\beta)\cos(\delta)\cos(\tau)$ (14)

and the azimuth angle (Step 7) is computed using the equation $$\cos(\theta) = -\frac{\sin(\beta)\cos(\varphi) - \sin(\delta)}{\cos(\beta)\sin(\varphi)}. \quad (15)$$

The equation for azimuth angle yields a value for $\theta$ measured clockwise from north before solar noon and counterclockwise from north after solar noon. Therefore, after solar noon, the azimuth angle is 360°−$\theta$ (when measuring azimuth clockwise from north). Solar noon (in minutes) is determined by the equation $n_t$=720+4×$\alpha$−$e_t$ (16)

where longitude ($\alpha$) is in units of degrees.

Returning now to the flowchart of the calculation routine (FIG. 11), the next step, after calculating the azimuth and elevation angles, is to command the PT to these angular positions. The number of steps from home which attains these positions is calculated for each axis. The pan axis is commanded to move to the azimuth angle and the tilt axis is commanded to the solar elevation. The gear ratio and mounting offsets for each axis are included in the calculations.

Once aimed at the computed solar azimuth and elevation, fine positioning is performed automatically in a closed loop manner, using feedback from the spectrometer to optimize positions of both PT axes (FIG. 11). The spectrometer output at 330 nm wavelength guides a series of intensity optimizing small increment moves of the PT. When the spectrometer signal intensity is maximized at the 330 nm wavelength, the fiber optics are properly aimed at the sun. The wavelength of 330 nm was chosen because it is the peak amplitude of the entire trace and yields reasonable magnitudes with only a 30 ms integration time. This short scan time helps to shorten the duration of automated fine positioning, since it is an iterative process.

Figure 12:
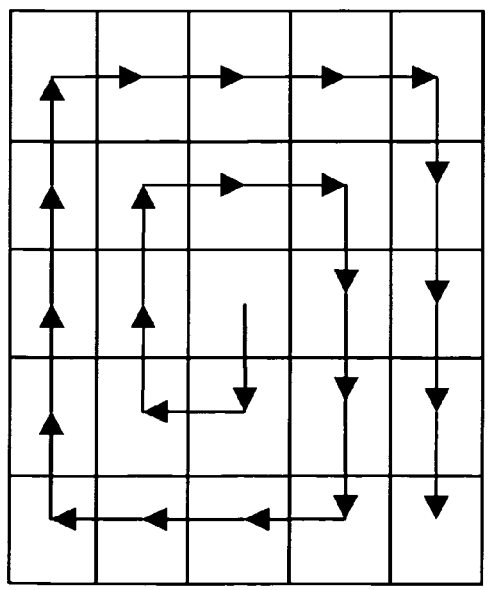
FIG. 12 shows the 5×5 spiral move.

In the following discussion, "step" refers to the smallest move increment of either PT axis, which is one halfstep of the motor. "Step" and "halfstep" will be used interchangeably unless otherwise specified. The fine positioning algorithm is capable of accommodating up to a two degree error in the open loop aiming of the optics (due to mounting error, calculation error and PT accuracy), even if no 330 nm signal is initially present. This is accomplished by performing a series of 20 step (1°) moves in a 5×5 square pattern spiral around the initial coordinates, until an intensity of 100+ counts is obtained (see FIG. 12). An intensity of 100 counts provides adequate feedback and closed loop control is then invoked. Offsets between the coordinates of this "100+ count" location and the calculated location are noted and they are added to the calculated coordinates the next time auto-positioning is done. If no location produces a reading over 100, then the process aborts, since there is either heavy cloud cover or the solar elevation is too low.

As soon as an intensity of greater than 100 is found, fine positioning continues with a series of east/west and up/down 5 step moves until the signal is maximized. Once optimized with 5 step moves, the offsets are again stored for use the next time auto-positioning is invoked. Then 1 step moves (0.05°) are taken in an up/down east/west sequence until the maximum intensity is found. The 1 step move sequence is repeated a second time, this time very quickly attaining a maximum, in order to correct for solar motion during the first longer duration series of moves. The final number of 1 step moves is not recorded as an offset for the next run. Having maximized the intensity at 330 nm, the solar disk is centered within the collection lens' field of view.

Due to the geometry of the PT unit, where the tilt axis rides on the pan axis, the actual angular displacement of the collection lens across the sky is equal to the pan angular motion only when the lens is aimed at the horizon (solar elevation angle of 0°). At the other extreme, if the lens is aimed vertically (solar elevation angle of 90°), motion of the pan axis does not change the angle of the lens, it only rotates about a vertical axis. At any elevation angle between horizontal and vertical, the lens translates at an angular distance which is less than and proportional to the cosine of the elevation angle. The relationship between lens motion and pan motion is $$\gamma = \theta \times \cos(\phi) \quad (17)$$

where $\gamma$ is the lens translation (degrees), $\theta$ is the pan rotational angle (degrees) and $\phi$ is the solar elevation angle (degrees). Because of this relationship, lens positioning by the pan axis is much finer than 0.051° per pan halfstep whenever the elevation angle is large. Consequently, for elevation angles greater than 60°, the minimum pan increment is increased (above 1 halfstep) by the control algorithm. Table 5 shows the pan increments used for fine positioning based upon elevation angle. Use of table values yields a maximum of 0.051° lens translation per pan increment. If the minimum pan increments were not adjusted upward for large elevation angles, then tracking the sun's azimuth angle would be slow or impossible when the sun is high over head.

TABLE 5

Minimum pan increment vs. elev. angle

| Elevation Angle (deg.) | Minimum Pan Increment (halfsteps) |
|---|---|
| 0-60 | 1 |
| >60-71 | 2 |
| >71-76 | 3 |
| >76-79 | 4 |
| >79 | 5 |

The closed loop fine positioning scheme described here allows for the relaxation of all mounting tolerances for the aiming device as well as accommodating any inaccuracy in the solar position equations. Effectively, there are no tight positional tolerances to be met since the instrument uses light intensity feedback to fine position the light collection optics.

Calculating Ozone and Storing Data. Having precisely aimed the collection lenses at the sun, the azimuth and elevation are recalculated and the final spectrometer scans (1190) are taken, acquiring the intensity data needed to calculate the ozone column thickness (FIG. 11). The recalculation of azimuth and elevation is necessary because of the time lapsed while auto-fine positioning searched for the optimal coordinates (about 30-45 seconds). Spectrometer intensity values used to calculate ozone are at 305.57 nm, 312.52 nm, and 320.09 nm wavelengths.

Once total column ozone is calculated (1191), the calculation routine then stores all of the measured parameters (1192) and calculated result in a file named "O3DATA" (FIG. 11). The parameters saved are: time of day (decimal hours), elevation (degrees), azimuth (degrees), intensities from the spectrometer at 305, 312, and 320 nm, and calculated ozone thickness DU. Once per calendar day, before the first intensity and ozone data are stored, the following additional values are saved: effective wavelengths and extraterrestrial intensities (obtained from Langley plots during calibration), day of year, and year.

As shown in FIG. 11, ten independent ozone readings (1193) are obtained every time the calculation routine is commanded to determine total column ozone. Automatic fine positioning is performed between each of the ten readings to accommodate the small change in solar position. Only the finest PT step increments are used for subsequent readings since the course adjustments from the first reading are still adequate. After all ten ozone samples are taken, the data is parsed and averaged (1194) to eliminate "noise." Two different averages are then stored: overall average and average excluding outliers.

The calculation algorithm is menu driven with keystrokes entered by the script program or from the keyboard, depending upon which function is desired. The keys that are active and the respective functions which they initiate are listed here:

a: auto-position: entered by a script program, which is dedicated to automatically aiming the collection lenses at sun; Calculated coordinates and closed loop spectrometer feedback are employed. This function is useful for testing the closed loop system. A copy of a useful script for this purpose can be found in Appendix D in Nebgen, G., B. "AUTOMATED LOW COST INSTRUMENT FOR MEASURING TOTAL COLUMN OZONE," Dissertation, 2006, University of North Texas, Denton, Tex.

c: calibrate—entered by a script program, which is dedicated to the automatic collection of Langley data. A copy of a useful script for this purpose can be found in Appendix E in Nebgen, G., B. "AUTOMATED LOW COST INSTRUMENT FOR MEASURING TOTAL COLUMN OZONE," Dissertation, 2006, University of North Texas, Denton, Tex.

f: finished—entered by a script program to indicate data collection complete o: ozone read—entered by a script program, which is dedicated to reading ozone. A copy of a useful script for this purpose can be found in Appendix A in Nebgen, G., B. "AUTOMATED LOW COST INSTRUMENT FOR MEASURING TOTAL COLUMN OZONE," Dissertation, 2006, University of North Texas, Denton, Tex.

t: track sun—entered from keyboard to aim PT at the calculated solar coordinates The means for manually positioning the PT from the PC keyboard is also provided within the calculation routine. In a few iterations, an operator can perform fine positioning by maximizing the signal magnitude displayed by the spectrometer. This capability is very useful when setting up the PT in a new location or after moving it for any reason. New mounting offsets can be determined by moving each PT axes until the maximum intensity is Spectrometer Software, Settings, and Display obtained. The total number of steps moved from the calculated coordinates are recorded and used as the new offsets for the specific installation.

The keys which control the manual positioning of the PT are listed here:

m: enter the magnitude (number of steps) for each of the following moves; the default move increment is 20 steps u: move tilt axis up d: move tilt axis down e: move pan axis counter-clockwise (east of home position for Denton location)

w: move pan axis clockwise (west of home position for Denton location)

The S2000 spectrometer is shipped with OOIBase32 Spectrometer Operating Software, which controls all spectrometer functions and operates in a windows environment. Table 7 below, lists the topics included in the Table of Contents of the OOIBase 32 Software Manual. As can be seen, a complete range of functions is provided which control data acquisition, display modes, file saving and printing. A copy of the complete operating software manual is available online at http://www.oceanoptics.com/technical/ooibase32.pdf.

There are several modes of control that may be used to operate the S2000. The primary mode when setting up an experiment or project is keyboard control. Other methods of control include external software or hardware triggering (see Operating Software Manual) and control via a script program. This ozone instrument uses a free script program called AutoIt, available for download on the internet, to issue simulated keyboard commands to the S2000 spectrometer.

Prior to running the script program, the spectrometer settings should be changed to save files with no headers, no overwrite notification, and a saved precision of zero. "Time Acquisition" mode, should be enabled and "Boxcar" averaging set to 5. The intensities for the four wavelengths of interest (305.57, 312.52, 320.09, 330.02 all in nm) are stored with each acquisition and streamed to a file named "uvlambda.txt", which resides in the qb45 directory. The four wavelengths are selected in the "time acquisition channel configuration" menu. File "uvlambda.txt" is accessed by the calculation program to obtain specific wavelength intensities used to calculate ozone.

Figure 13:
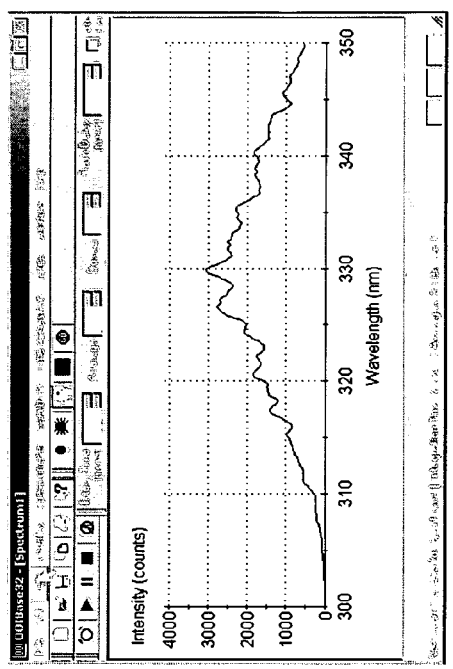
FIG. 13 shows a filtered solar spectrum with 30 ms integration time.
Figure 14:
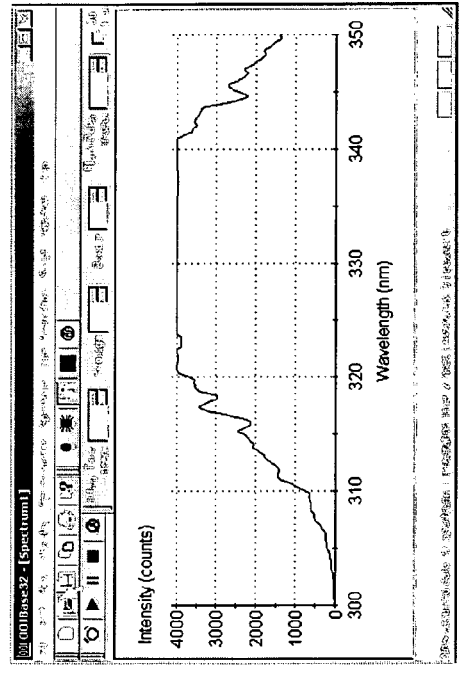
FIG. 14 shows a filtered solar spectrum with 80 ms integration time.

FIG. 13 is a depiction of the spectrometer screen displaying the bandpass filtered solar spectrum. Notice the peak amplitude at about 330 nm (the boxcar setting of 5, and the 30 ms integration times are not visible on this graphic). FIG. 14 shows a trace with 80 ms integration time, used to collect the 312.5 nm intensity. On this trace notice that the 330 nm signal is off scale and the 320 nm signal would be off scale for a slightly lower airmass. Due to the light intensity differences across the spectrum, even with the optical bandpass filter, separate scans are required for each desired wavelength, with longer integration times for the shorter wavelengths. Four integration times were selected so that the amplitude of each of the four utilized wavelengths can be a significant percentage of the spectrometer's full scale intensity, but never off scale, for all possible airmass values at the station latitude. It is not practical to use only one integration time that keeps the longer wavelengths on scale (like in FIG. 13) because the shorter wavelengths would become almost undetectable, with the result that their stored amplitude readings are influenced by noise and quantization error. The integration times employed for each wavelength used in this system are as shown in Table 6:

TABLE 6

Integration times

| Wavelength | Integration Time |
|---|---|
| 305.57 nm | 400 ms |
| 312.52 nm | 80 ms |
| 320.09 nm | 40 ms |
| 330.02 nm | 30 ms |

TABLE 7

OOIBase32 Table of Contents

1 OOIBase32 Introduction

Product Overview
Free Updates
2 Setting Up OOIBase32

Connecting an A/D Converter to the PC
Install OOIBase32
Configuring OOIBase32 and your Hardware
Configure Sampling Optics
Getting Help
3 File Menu Functions New Spectrum Window (Ctrl+N)
New
Open
Close
Save
Autoincrement Filenames
Print
Print Preview
Print Setup
Exit
4 Edit Menu Functions Copy Spectral Data
Copy Graphical Spectra (Ctrl+C)
Settings
5 View Menu Functions Display Properties
Display Property Files
Spectrum Scale
Background Image
Set Graph Background Color
Set Axis Text Properties
Set Graph Title
Rename Spectral Window
Cursor
Grid
Legend
Main Status Bar
6 Overlay Menu Functions Select to add overlay
Clear All
7 Spectrometer Menu Functions Configure
Open Configuration

TABLE 7-continued

OOIBase32 Table of Contents

Save Configuration As
8 Spectrum Menu Functions

Store Dark
Store Reference
Snapshot
Single Exposure
Emergency Reset
Global
Configure Data Acquisition
Scope Mode
Scope Mode Minus Dark
Absorbance Mode
Transmission Mode
Relative Irradiance
Specular Reflection Mode
Script-defined Custom Mode
Reference Color Temperature
Configure Standard Correction
Take Log of Vertical Scale
Time Normalized Intensity
9 Time Acquisition Menu Functions Configure
Activate Time Acquisition
Start
Pause
Stop
Suspend Graph Display
Save Data
10 Other Menu Functions Script Menu Functions
Window Menu Functions
Help Menu Functions
11 Sample Experiments Preparing for Experiments
Absorbance Experiments
Transmission Experiments
Reflection Experiment 55
Relative Irradiance Experiments
Time Acquisition Experiments
Appendix A: Toolbar Index General Functions
Platinum Functions
Global Functions
Acquisition Parameter
Spectrum Controls
Cursor
Graph Scale
Spectral View Mode
Time Acquisition
USB-LS-450
NIR512
USB-ISS-UV/VIS
Appendix B: Toolbar Buttons Quick Reference Appendix C: File Formats Spectral Data Files
Experimental Parameters Files
Display Properties Files
Spectrometer Configuration Files
Time Acquisition Parameters Files
Time Acquisition Data Files and Stream Files
Grams/32 SPC Files
Copied Data Clipboard Format
Index Script. Overall instrument control is performed by a script program written in AutoIt, version 3.0.101. AutoIt v3 is an opensource "freeware" programming language that is downloadable from website http://www.autoitscript.com/autoit3/. It may be copied and used without charge with very minimal restrictions (see End-User License Agreement at http://www.autoitscript.com/autoit3/docs/license.htm).

Figure 15:
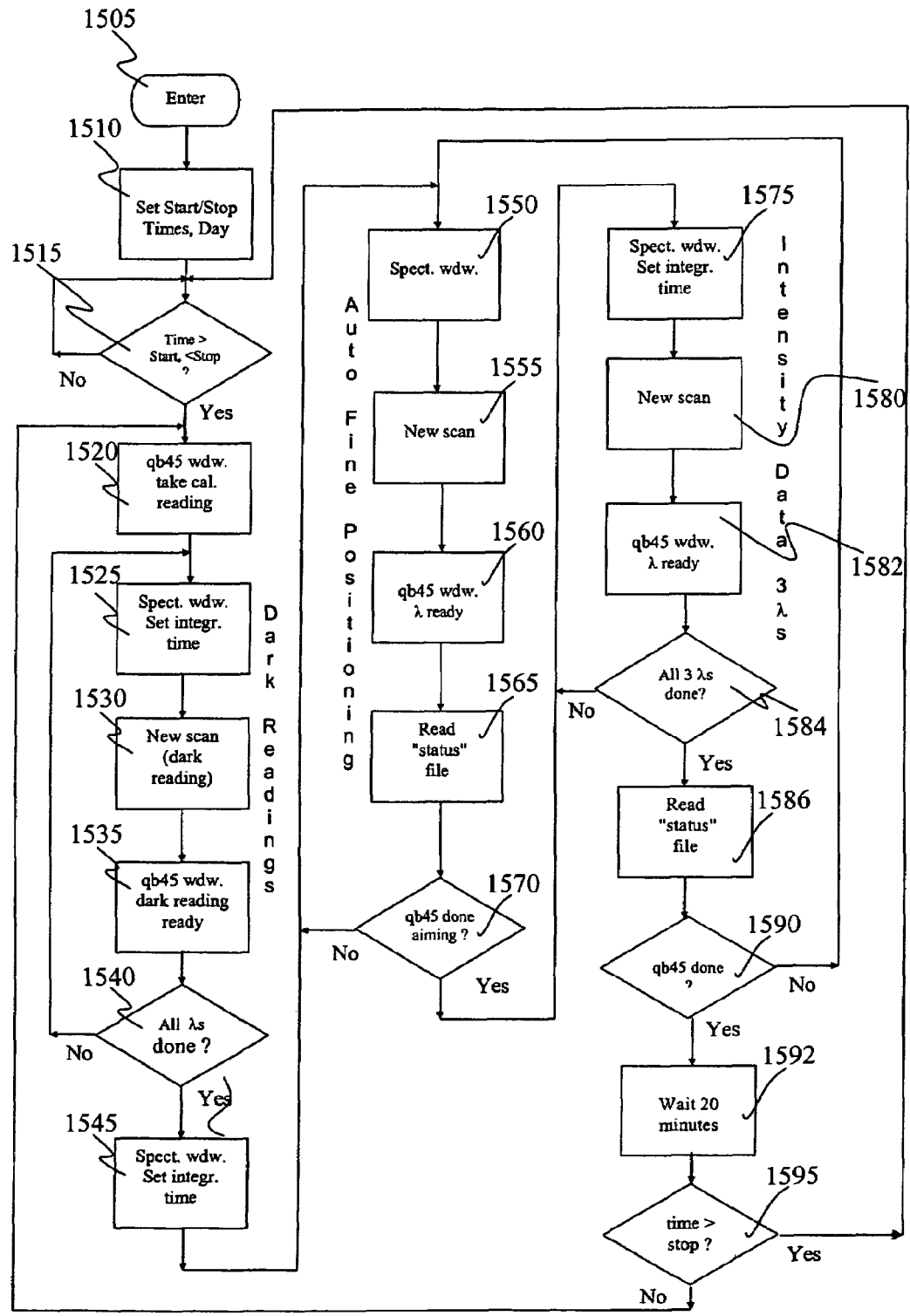
FIG. 15 shows a script program flow.

AutoIt v3 provides all of the function needed to control the spectrometer and the calculation program and coordinate the shared files. A copy of a useful script for this purpose can be found in Appendix B in Nebgen, G., B. "AUTOMATED LOW COST INSTRUMENT FOR MEASURING TOTAL COLUMN OZONE," Dissertation, 2006, University of North Texas, Denton, Tex. FIG. 15 is a flowchart for this program.

Following FIG. 15, the script program begins by initializing the start time, stop time, and stop day for collecting ozone samples. Ozone data collection will continue, unattended, starting at the time specified by parameters $starthr and $startmin, and running until $stophr and $stopmin are reached. The script program will start and stop each day at these times without intervention until the specified stop day ($stopday) is reached. If $stopday is set to zero, the program will run daily until manually stopped.

When the pc clock time equals the script program start time, the program initiates data collection (for calibration or ozone reading purposes). The first operation is to activate the calculation program window (qb45 window) and issue a "c" or "o" keystroke, telling the calculation routine whether a calibration or an ozone reading is to be performed, respectively. The spectrometer window is then activated and the integration time is set for the appropriate wavelength. For example, for 320 nm the key sequence issued by the script program to the spectrometer is the following: "Alt", s, d, "Enter", 40, "Enter". This key sequence sets the integration time to 40 ms. After setting the integration time, a sample is collected by the spectrometer, which is already set to the "Time Acquisition" mode. The key sequence for storing a scan is "Alt", t, s.

The script program then waits while the spectrometer finishes the last scan plus the requested time acquisition. After this wait, the qb45 window is activated and script issues the key "n", which signals the calculation program that the spectrometer data is ready. The calculation program immediately stores the dark value for the particular wavelength(s). This process continues until dark readings for all four wavelengths have been recorded. The 320 nm and 330 nm dark readings are both taken during a single 40 ms scan, which is the exact sample integration time used for the 320 nm wavelength. The sample integration time used for 330 nm during aiming of the lenses is 30 ms. Based upon many observations, the dark readings obtained at 30 ms and 40 ms integration times are seldom different by a single count, and it is not necessary to get an exact dark reading for 330 nm since it is used only to determine relative intensity when aiming the PT.

Next, the spectrometer window is activated and the integration time is set to 30 ms in preparation for repetitive scanning as the calculation program fine tunes the aiming of the PT. A new scan is taken, qb45 is activated, and the "n" key is issued telling the calculation routine that a new scan is available. The "STATUS" file is read by the script routine to determine if qb45 has indicated "done". This sequence repeats until the calculation program is finished aiming the PT and issues the "done" status.

At this point the final three scans which are used to calculate ozone (or calibrate) are taken, beginning with 320 nm, and ending with 305 nm. The integration times are different for each wavelength due to light intensity differences at each wavelength. Once the calculation routine has received all three values, it calculates ozone. The script program repeats the process of providing closed-loop feedback for aiming, and taking new final scans until the qb45 program indicates in the "STATUS" file that it is finished. This allows for multiple reads to be taken and averaged by the calculation routine. When the calculation routine indicates that it is finished calculating ozone ("doneo3" or "doneca" in the "STATUS" file), the script program waits 20 minutes and then checks the time and compares it to $stophr and $stopmin. If the stop time has not yet been reached, the data collection process is repeated, with new dark readings taken. If the stop time has been reached, the script program goes back into the wait loop until the start time arrives the next day.

Ozone Equation. Algorithms to calculate ozone were developed based upon the Lambert-Beer-Bouguer (LBB) Law explained above. The following equation (Equation 6) was derived for calculating ozone thickness x.

$$x = \frac{\ln\frac{I_{01}}{I_{02}} - \ln\frac{I_1}{I_2} + (b_2 - b_1)y}{a_1 - a_2} \quad (6)$$

The equation variables were defined as $a_\lambda = \alpha_\lambda \mu(Z)$ $b_\lambda = \beta_\lambda$ $y = m(Z)P/P_0$ where
- $I_{0\lambda}$ = intensity of light before passing through the atmosphere
- $I_\lambda$ = intensity of light at a given wavelength $\lambda$, at the Earth's surface.
- $\alpha_\lambda$ = absorption coefficient for ozone
- $\mu(Z)$ = ratio of actual and vertical path lengths through the ozone layer
- $\beta_\lambda$ = Rayleigh scattering coefficient
- $m(Z)$ = ratio of actual and vertical path lengths through entire atmosphere; This ratio is called "airmass." Airmass is a function of Z, the Zenith angle, and is typically calculated as $1/\cos(Z)$ (OSC 2004).
- P = atmospheric pressure
- $P_0$ = standard atmospheric pressure (1013.25 mb)

As previously discussed, the ratio of two wavelengths causes the effect of aerosols to cancel out of the equation. The cancellation of aerosols is useful because of their variability and our inability to accurately know the atmospheric constituents and concentrations of aerosols at the time we are measuring ozone. Also, great difficulty would be encountered in the determination of attenuation constants for the individual aerosols.

In actuality, UV attenuation by particulate matter is somewhat wavelength dependent, and the effect is more pronounced when particulate levels are high. Therefore, given high aerosol concentrations, Equation (6) will produce some amount of error because the aerosol effect does not perfectly cancel out. A better result can be obtained by introducing a third wavelength into the equation. Recall the derivation for two wavelengths (Equation 4)

$$\frac{I_1}{I_2} = \frac{I_{01}e^{-a_1x - b_1y - c_1z}}{I_{02}e^{-a_2x - b_2y - c_2z}} \quad (4)$$

which was algebraically solved for ozone thickness x to obtain Equation (6). Introducing a third wavelength and using a two pair ratio gives $$\frac{I_1/I_2}{I_2/I_3} = \frac{I_{01}e^{-a_1x - b_1y - c_1z}/I_{02}e^{-a_2x - b_2y - c_2z}}{I_{02}e^{-a_2x - b_2y - c_3z}/I_{03}e^{-a_3x - b_3y - c_4z}} \quad (18)$$

which can be solved for x using the same methodology as used for the single pair of wavelengths. Doing the algebra yields $$x = \frac{\left(\ln\frac{I_{01}}{I_{02}} - \ln\frac{I_1}{I_2}\right) - \left(\ln\frac{I_{02}}{I_{03}} - \ln\frac{I_2}{I_3}\right) +}{(a_1 - a_2) - (a_2 - a_3)} \quad (19)$$
$$\frac{[(b_2 - b_1) - (b_3 - b_2)]y + [(c_2 - c_1) - (c_3 - c_2)]z}{(a_1 - a_2) - (a_2 - a_3)}$$

which has the same format as Equation (6) except that the aerosol terms are present in the equation. The aerosol effect is $$(c_2 - c_1) - (c_3 - c_2) \quad (20).$$

If wavelength 2 is approximately centered between wavelengths 1 and 3, then the two components of Equation (20) approximately cancel. The difference $c_2 - c_1$ is about equal to $c_3 - c_2$, if one assumes a linear change in aerosol absorption with wavelength. This is an acceptable assumption as long as the wavelengths are not spread apart very far. The result is that the two pair calculation better accommodates the aerosol effect by allowing its cancellation for a greater range of particulate concentrations. It has been found that the two pair ozone calculation yields more accurate results than the single pair calculation for airmass values below 3. The two pair calculation thus serves to minimize the error introduced by the small wavelength dependency of particulate absorption.

Now, canceling the aerosol terms from Equation (19) gives $$x = \frac{\left(\ln\frac{I_{01}}{I_{02}} - \ln\frac{I_1}{I_2}\right) - \left(\ln\frac{I_{02}}{I_{03}} - \ln\frac{I_2}{I_3}\right) + [(b_2 - b_1) - (b_3 - b_2)]y}{(a_1 - a_2) - (a_2 - a_3)}. \quad (21)$$

This instrument calculates total column ozone using Equation (21). The details for obtaining each of the constants and variables needed to obtain a numeric solution to this equation will now be discussed.

As mentioned earlier, the three intensities $I_1$, $I_2$, and $I_3$ needed to calculate ozone are read from the spectrometer at wavelengths 305.57, 312.52, and 320.09 nm. These wavelengths are very nearly the same as used in MICROTOPS II (Morys et al. 1996). These $\lambda$s are spaced far enough apart so that ozone absorption is different between them, thereby yielding reasonably large intensity ratios in Equation (21). But, the spacing between wavelengths is not so large as to invalidate the aerosol cancellation discussed above. Usage of these $\lambda$s has been validated through years of field experience with the MICROTOPS II hand held ozonometer. Thus the number of unknowns in the development of this new instrument were reduced by starting with a proven set of wavelengths.

The Langley Method. Extraterrestrial constants ($I_0$s) for each wavelength used in Equation (21) are obtained using the Langley method. The Langley method extrapolates the linear relation between the natural log of light intensity and path length through the atmosphere to obtain the zero airmass (top of atmosphere) light intensity. This is the extraterrestrial intensity, $I_0$.

The Langley method also employs the LBB Law for light extinction through the atmosphere (Hall 2000):

$$I(\lambda)=I_0(\lambda)e^{-\delta(\lambda)m(z)} \quad (22)$$

where m(z) is the airmass as defined above and $\delta(\lambda)$ is an overall light attenuation constant, including the lumped effects of ozone and Rayleigh attenuation. Mie scattering is assumed to be negligible because Langley plots are best performed on a clear day at high altitude where there is little particulate pollution. To simplify, for a given wavelength and airmass, $I(\lambda)$, $I_0(\lambda)$, and $\delta(\lambda)$, and m(z) will be denoted by I, $I_0$, $\delta$, and m respectively. Equation (22) is then rewritten as $$I=I_0 e^{-\delta m} \quad (23)$$

Algebraically rearranging Equation (23) yields:

$$\frac{I}{I_0} = e^{-\delta m} \quad (24)$$

$$\ln\left(\frac{I}{I_0}\right) = -\delta m \quad (25)$$

$$\ln I - \ln I_0 = -\delta m \quad (26)$$

$$\ln I = -\delta m + \ln I_0 \quad (27)$$

This is the equation of a line where I is the intensity after passing through the atmosphere (as received at the spectrometer in our case), $-\delta$ is the slope, m (airmass) is the independent variable, and $\ln(I_0)$ is the y-intercept (airmass=0). Thus, by taking the anti-log of the y-intercept, the extraterrestrial intensity ($I_0$) can be obtained for the particular wavelength.

By collecting multiple intensity measurements with a spectrometer over the course of a cloudless day, a best-fit straight line for the data can be obtained by regression analysis. The slope $-\delta$ and the y-intercept are readily obtained from the regression equation. Since this ozone instrument automatically tracks the sun and records calibration data at 5 minute increments, Langley data is easily recorded without operator intervention. After data collection is complete, intensity data can be reviewed prior to plotting to verify that no interferences were present and that the sky remained clear during the entire period.

To accomplish the linear regression, the Langley data which is stored in file "O3DATA" by the calculation routine is opened in Microsoft Excel. The airmass (1/cos(Z)) is calculated for each solar elevation angle and the natural log of intensity is computed for each wavelength. Table 8 shows a subset of the data, which was used to generate the Langley plot of FIG. 16. This data and plot are for a calibration that was done on Mar. 30, 2005.

TABLE 8

Subset of Langley data for Mar. 30, 2005
Day/Year 89 2005

| Time | Elev. (Deg) | Azimuth (Deg) | 305.57 nm | 312.52 nm | 320.09 nm | Airmass | ln (305 nm) | ln (312 nm) | ln (320 nm) |
|---|---|---|---|---|---|---|---|---|---|
| 10.14583 | 44.91788 | 123.5861 | 1184 | 1217 | 1354 | 1.42 | 7.08 | 7.10 | 7.21 |
| 10.15333 | 44.99634 | 123.6997 | 1184 | 1218 | 1345 | 1.41 | 7.08 | 7.10 | 7.20 |
| 10.16194 | 45.0863 | 123.8305 | 1202 | 1226 | 1361 | 1.41 | 7.09 | 7.11 | 7.22 |
| 10.16917 | 45.16165 | 123.9405 | 1180 | 1214 | 1346 | 1.41 | 7.07 | 7.10 | 7.20 |
| 10.2725 | 46.22878 | 125.5454 | 1281 | 1285 | 1405 | 1.38 | 7.16 | 7.16 | 7.25 |
| 10.28028 | 46.30825 | 125.6686 | 1281 | 1285 | 1410 | 1.38 | 7.16 | 7.16 | 7.25 |
| 10.28917 | 46.39892 | 125.8098 | 1260 | 1265 | 1384 | 1.38 | 7.14 | 7.14 | 7.23 |
| 10.29889 | 46.49791 | 125.9648 | 1264 | 1269 | 1394 | 1.38 | 7.14 | 7.15 | 7.24 |
| 10.40972 | 47.61235 | 127.7707 | 1381 | 1353 | 1464 | 1.35 | 7.23 | 7.21 | 7.29 |
| 10.41833 | 47.69781 | 127.9141 | 1360 | 1322 | 1442 | 1.35 | 7.22 | 7.19 | 7.27 |
| 10.42639 | 47.77762 | 128.0487 | 1370 | 1333 | 1451 | 1.35 | 7.22 | 7.20 | 7.28 |
| 10.43639 | 47.87649 | 128.2162 | 1350 | 1315 | 1431 | 1.35 | 7.21 | 7.18 | 7.27 |
| 10.54167 | 48.90316 | 130.0185 | 1471 | 1393 | 1498 | 1.33 | 7.29 | 7.24 | 7.31 |
| 10.54917 | 48.97528 | 130.1496 | 1481 | 1402 | 1504 | 1.33 | 7.30 | 7.25 | 7.32 |
| 10.55639 | 49.04461 | 130.2762 | 1462 | 1394 | 1495 | 1.32 | 7.29 | 7.24 | 7.31 |
| 10.56528 | 49.12976 | 130.4324 | 1449 | 1388 | 1488 | 1.32 | 7.28 | 7.24 | 7.31 |

Figure 16:
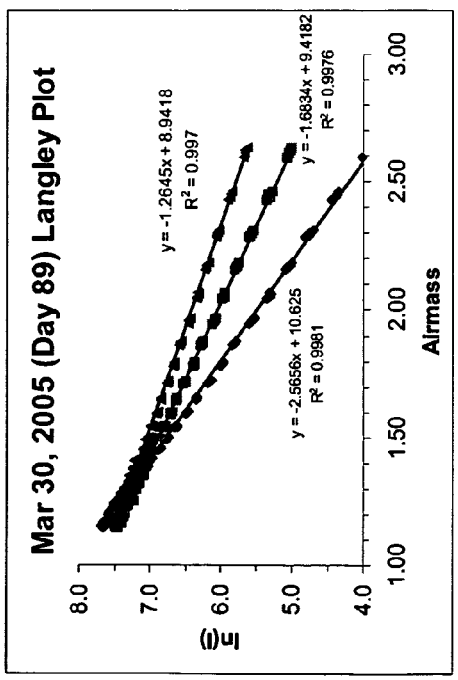
FIG. 16 shows a Langley Plot.

The lower trace in FIG. 16 is for $\lambda=305$ nm and the upper trace is for $\lambda=320$ nm. The steepest slope is associated with the shortest wavelength, since ozone attenuation is stronger for the higher frequencies. The y-intercepts are read directly from the regression equations. Taking the anti-log of these intercepts gives us the extraterrestrial constants. The results are summarized in Table 9.

TABLE 9

| | Extraterrestrial constants | |
|---|---|---|
| $\lambda$ (nm) | y-intercept | $I_0 = e^{yint}$ |
| 305 | 10.625 | 41151 |
| 312 | 9.4182 | 12310 |
| 320 | 8.9418 | 7645 |

Figure 18:
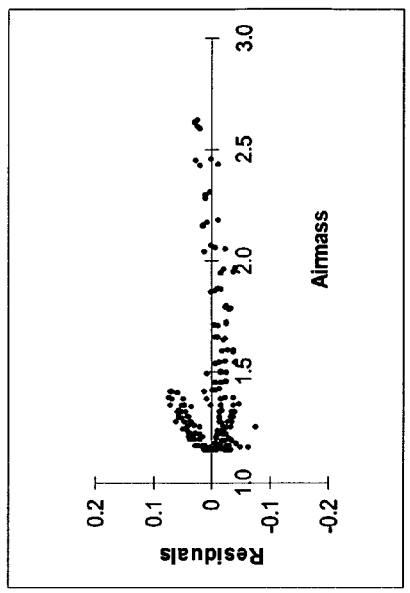
FIG. 18 shows the residuals for 312 nm.
Figure 19:
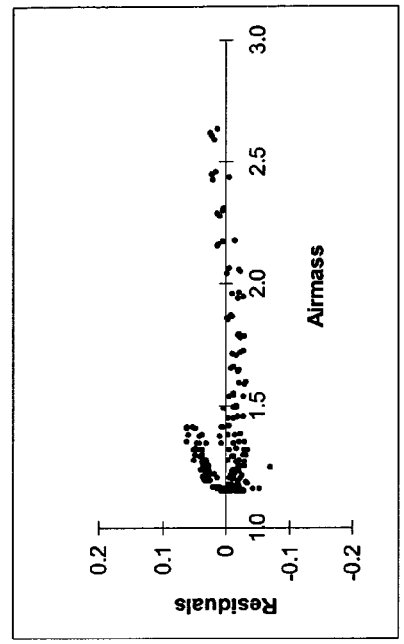
FIG. 19 shows the residuals for 320 nm.
Figure 17:
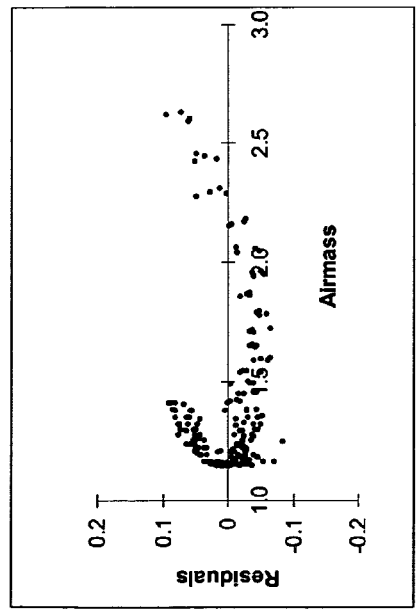
FIG. 17 shows the residuals for 305 nm.

Notice in FIG. 16 that the $R^2$ values are close to 1.0, indicating a good fit of the regression line to the data. The residuals for the three Langley plots are shown in FIG. 17 through FIG. 19. Some non-linearity is indicated by the residuals, particularly for the 305 nm wavelength. However, the percent errors are small, enabling the high $R^2$ values which were obtained for each wavelength. Understanding the source of these non-linearities will be the topic of future work to improve Langley calibrations.

The extraterrestrial constants in Table 9 have no absolute units such as lumens, watts per square meter, etc. The values represent how many counts the CCD in the spectrometer would produce if the spectrometer and fiber optics were located at the top of the atmosphere. Recall our ozone equation, which uses the ratio of ground level intensity to extraterrestrial intensity. Any intensity units cancel out of the equation, negating the need for specific units. Since the spectrometer reads in counts, intensity is measured in counts. It is not a problem that the $I_0$s exceed the spectrometer's full scale reading of 4096 counts (12 bits) because the $I_0$s are extrapolated from the Langley plot, not measured by the spectrometer.

Now, having a method for obtaining the extraterrestrial constants, the remaining variables needed in Equation (21) to calculate ozone are y, α (ozone attenuation constant) and β (Rayleigh attenuation constant). The variable y is simply defined as m (airmass) times P (atmospheric pressure) divided by $P_0$ (standard pressure). Only a little accuracy is lost by assuming $P=P_0$, and setting y equal to airmass.

Recall that ozone absorbs shorter wavelength UV more than longer wavelength UV. The relationship of ozone attenuation constant to UV wavelength is non-linear. Previously, absolute light absorption cross sections for ozone in the UV range 185 to 350 nm have been determined. The results are tabulated at 0.5 nm increments for each wavelength in this range. Developers of MICROTOPS II derived the following equation which was curve fitted to this data, to enable easy instrument calibration without table look-up and interpolation (Morys et al. 1996):

$$\alpha(\lambda) = (2.1349 \times 10^{19})e^{-0.14052\lambda} \quad (28)$$

Similarly, Rayleigh scattering also causes greater attenuation of shorter UV wavelengths and the relationship is non-linear as well. A table of Rayleigh scattering coefficients was developed by Pendorf for wavelengths in the range of 200 nm to 20 μm in 10 nm increments (Penndorf 1957). Much like the method for developing Equation (28) for ozone absorption, MICROTOPS II developers also fit a polynomial to this tabular Rayleigh data (Morys et al. 1996). The MICROTOPS II equation for Rayleigh coefficients is $$\beta(\lambda) = 16.407 - 0.085284\lambda + 0.00011522\lambda^2 \quad (29)$$

Both Equations (28) and (29) are implemented in the ozone calculation program to obtain values for ozone and Rayleigh attenuation constants.

Effective Wavelengths. Prior to determining ozone and Rayleigh attenuation constants for each wavelength used in the ozone equation, "effective" wavelengths are determined for each λ and these effective wavelengths are used to calculate the attenuation constants. Effective wavelengths are essentially overall system "calibrated" wavelengths and are adjustments to the theoretical wavelengths read directly from the spectrometer. They are obtained by using a known and accurate ozone reading to empirically determine what the effective system wavelengths should be to yield that result. This procedure will be explained in detail below. Accurately defining effective wavelengths plays a part in instrument calibration as will be shown.

To derive a method for obtaining effective wavelengths requires us to visit the LBB law again. Equation (3) above is copied here for easy reference.

$$I(\lambda) = I_0(\lambda)e^{-a(\lambda)x - b(\lambda)y - c(\lambda)z} \quad (3)$$

This equation can be written simply as $$I = I_0 e^{-ax-by-cz} \quad (30)$$

with wavelength dependence implicit. This equation takes into account ozone (a), Rayleigh (b), and Mie (c) attenuation. The effects of Mie scattering will be eliminated because calibration data will be collected on perfectly clear days (preferably at high altitude) when particulate concentration is very low. Removing the term for Mie scattering and substituting the definitions of a(λ) and b(λ) yields $$I = I_0 e^{-\alpha\mu x - \beta m \frac{P}{P_0}} \quad (31)$$

where the dependence on λ and Z (zenith angle) is not shown but is still implicit. A further simplification can be made for low values of airmass. For low airmass values, m and μ are approximately equal allowing a further simplification to be made (Morys et al. 1996).

$$I = I_0 e^{-m\left(\alpha x - \beta \frac{P}{P_0}\right)} \quad (32)$$

Taking the natural log of both sides of this equation gives $$\ln I = \ln I_0 - m\left(\alpha x - \beta \frac{P}{P_0}\right) \quad (33)$$

Which can be rewritten as $$\ln I = -\left(\alpha x - \beta \frac{P}{P_0}\right)m + \ln I_0 \quad (34)$$

This is the equation of the line for ln I vs. m with slope $$-\delta = -\left(\alpha x - \beta \frac{P}{P_0}\right) \quad (35)$$

Looking back at Equation (27) used for the Langley plots, it is the same as Equation (34), when −δ is defined as in Equation (35). Thus the slopes of the Langley regression lines provide empirical values for −δ for each wavelength. Using an empirical value for −δ and substituting Equations (28) and (29) for α and β into Equation (35) allows the effective wavelength of the system to be calculated for each λ. However, this requires that an accurate measurement for total column ozone (x) be available from some other reference instrument. Doing the substitution yields $$\delta = -\left(2.1349 \times 10^{19} e^{-0.14052\lambda} x' - \right. \quad (36)$$
$$\left. (16.407 - 0.085284\lambda + 0.00011522\lambda^2)\frac{P}{P_0}\right)$$

This is a quadratic equation and, given a calibrated value for ozone (x), all values are known except for the effective wavelength λ. The equation can be solved for λ, or a trial and error solution can easily be done since the approximate wavelength is already known (it was read from a calibrated spectrometer). Note that x' was substituted for x in Equation (36), where x'=x/1000, converting from DU to atm-cm, the units compatible with the equations for α and β.

As noted, obtaining effective wavelengths requires that total column ozone be accurately known at the time and location where the instrument is being calibrated. This usually implies collocation at a site with a calibrated Dobson or Brewer instrument. Due to expense of collocation, because of distance to nearest Dobson or Brewer, effective wavelengths were determined for this instrument by using TOMS and MICROTOPS II to obtain local total column ozone data. Clearly, more accurate effective wavelengths, which are an integral part of instrument calibration, would result by collocation with a benchmark instrument.

Ozone Path Length. Recall that the equation used to calculate ozone (Equation 21) requires us to know $\alpha_\lambda$ (the ozone attenuation constant), which is equal to $\alpha_\lambda \mu(Z)$. $\alpha_\lambda$ is the absorption coefficient for ozone for which an equation was given in the previous section and $\mu(Z)$ is the ratio of the actual and vertical path lengths through the ozone layer. $\mu(Z)$ is calculated using the following equation:

$$\mu(Z) = \frac{1}{\sqrt{1 - v \times \sin^2 Z}} \quad (37)$$

where $v$ is given by $$v = \frac{(R+r)^2}{(R+h)^2} \quad (38)$$

R=mean earth radius (6371 km)
r=height of ozone measuring instrument above sea level [km]
h=height of ozone layer above sea level [km]

$$h \approx 26 - 0.1 \times \beta \quad (39)$$

where $\beta$ is the station latitude in degrees.

Calculation of Ozone. We now have a means of determining all of the variables needed to calculate ozone using Equation (21) developed above. The ground level light intensities for the three wavelengths are measured using the spectrometer, and the Langley method is employed to obtain extraterrestrial constants as well as the regression line slopes needed to calculate effective wavelengths for the instrument. An ozone reading is obtained from a calibrated instrument (such as MICROTOPS II) to enable effective wavelength calculation via Equation (36). Once effective wavelengths and extraterrestrial constants are determined, the values are inserted as constants in the calculation program, which computes the ozone and Rayleigh attenuation constants based upon those values.

Having determined all variables needed to calculate ozone, the instrument will automatically take ozone readings daily, hourly, every 20 minutes (or other specified time) and store the results consecutively in a file. Periodic instrument calibration is required and includes both system components (such as extraterrestrial constants and effective wavelengths) and subsystem components (such as spectrometer and collimating lenses).

Noise Reduction. Algorithmic and data collection methods are employed to reduce measurement error which arises from several noise sources. Two sources of noise which can affect accuracy are spectrometer signal to noise ratio and rapidly changing atmospheric conditions. Rapidly changing means that, between successive scans of the spectrometer, the atmospheric clarity is different due to cloud thickness or other particulate variation (e.g. smoke, airplane vapor trails, etc.)

Spectrometer Boxcar Averaging. As specified in Table 2, the spectrometer has a signal to noise ratio of 250:1 for a single acquisition. This means that for single acquisitions the error due to signal to noise ratio (S/N) could be as high as 0.4%. The ozone equation uses the ratio of two pair of wavelengths, allowing this error component to rise to 0.8% per pair (1.6% total) if, say, the numerator has a plus error and the denominator has a minus error. This is a worst case scenario that is statistically unlikely, but considering both pairs of wavelengths, it is not unreasonable to expect 0.8% error due to this effect. This is almost 1% and can be significant, especially since there are error sources other than the spectrometer S/N.

Spectrometer S/N is dictated by three sources of error inherent in CCD array spectrometers: photon noise, dark noise, and read noise. Photon noise is a result of the randomness in the arrival of photons at the CCD array. Photon arrival rate is characterized by the Poisson distribution. Dark noise originates in the CCD itself due to thermally generated electrons which are independent of photon induced current. Dark noise also follows a Poisson distribution. The third source of S/N error, termed "read noise" is a compilation of error due to all electrical signal processing. The largest contributor to read noise is the preamplifier which amplifies the signal prior to its analog to digital conversion. The preamplifier is part of the CCD chip itself. The next largest source of read noise is the analog to digital converter (A/D) wherein the signal is quantized and digitized.

The best way to improve S/N for a given spectrometer is to employ signal averaging. This can be done by averaging several scans together or by "binning." Binning is a technique used in digital photography wherein the charge from a specified number of adjacent pixels is combined when reading the CCD. The result is an image consisting of averaged pixels. This technique is good for removing read noise, but the tradeoff is lower image resolution. Ocean Optics spectrometers have the capability to perform binning, but it is called "boxcar" averaging. With an Ocean Optics spectrometer, boxcar averaging means that for a single spectrometer trace, n pixels before and n pixels after each pixel are averaged with the specific (center) pixel. The average value is then assigned to the specific pixel.

Both multiple scan averaging and binning techniques smooth the data, and both techniques improve S/N by the square root of the number of scans or pixels used for averaging (Ocean Optics 2000). But, the tradeoffs required by each method are different. Averaging several scans exacts a time penalty, since multiple scans should be made. If integration times are short, this may not be an issue, but for integration times greater than about 50 ms, the time penalty can be significant. This instrument requires a 400 ms scan in order to get a reasonable number of counts for the 305 nm wavelength. If ten scans were averaged the total time just to collect the 305 nm wavelength would be 4.0 sec. If the atmosphere were perfectly stable this might not be an issue since all three wavelengths would be measured under the same conditions (as is required for a good reading—recall we are using the ratios of multiple wavelengths). But small (sometimes large) changes occur quickly, especially around a metropolitan area where smog is present. The result is that, in order to use multiple scan averaging, integration times should be reduced. This may be accomplished by increased optical fiber diameter or another of the suggested methods for bringing more light into the spectrometer.

Boxcar averaging is employed in this instrument in order to use a 200 um fiber and keep total sample time low. The downside to boxcar averaging is that spectral resolution is reduced due to averaging shorter and longer wavelengths with the pixel of interest. This would be a serious issue if we were relying wholly on the spectrometer calibration to accurately identify the appropriate wavelength. But, because we are using the Langley plots to calculate effective wavelengths, the spectrometer does not need very fine wavelength resolution. As long as the effective wavelengths for each of the three UV λs used to calculate ozone are sufficiently separated, there is no problem. Obviously, if the boxcar averaging window were spread too wide, the wavelengths would be interrelated and their unique information would be lost. In order to compute accurate ozone values, the attenuation constants (slope of Langley plots) for each wavelength should be substantially different. A wide boxcar window would produce very little difference between the three λs.

The Langley plots shown in FIG. 16 above were made with boxcar averaging set to 5. This means that 5 pixels before and 5 pixels after the desired λ were averaged with the center pixel to produce the value for λ reported by the spectrometer. As can be seen in FIG. 16, the slopes of the three λs are substantially different, and the regression fit is very good. This implies that, even though a total of 11 pixels are being averaged for varying airmass, the effective wavelengths are not changing as solar elevation changes. Therefore, the attenuation constants are also not changing with elevation angle and total column ozone can be accurately calculated with the effective wavelengths.

Thus the spectrometer signal to noise ratio is increased by boxcar averaging, from 250:1 to $$250 \times \sqrt{11}:1 = 250 \times 3.32:1 = 829:1$$

and the total worst case error contributed by a single wavelength ratio is ±0.12%.

Data Averaging. Spectrometer signal to noise error has been adequately dealt with by using boxcar averaging, and attention is now turned to other error sources such as atmospheric variations between successive scans, and any other system variation that shows up as "noise" in the total ozone calculation. To lessen the effects of these sources of error, a heuristic methodology was incorporated in the calculation program. The algorithm collects ten independent sets of data each time the script program commands it to take an ozone reading. The highest and lowest values are then trimmed and the remaining values are averaged. The trimming and averaging algorithm operates as follows: First, any values which are stored as −1 are eliminated. The calculation routine stores −1 whenever any wavelength intensity is zero or the calculated ozone value is negative. The remaining data are then sorted from lowest to highest. If seven or more values remain (after eliminating the −1 values), then the highest two and lowest two are eliminated. If only 4-6 values were non-negative, then just the single highest and single lowest values are eliminated. If less than 4 values were non-negative, then the ozone average is reported as −1, indicating that a good reading could not be obtained for existing sky conditions.

Once the data is sorted and the high and low values trimmed, the remaining data are averaged. To enhance the effectiveness of averaging in reducing overall noise, another average is then computed which excludes values that still appear to be outliers. Elimination of remaining outliers is done is two steps: First, if the removal of any of the remaining values changes the overall average by more than 5 DU, it is defined as an outlier and is removed. Once all values are tested, then a new average is computed without the eliminated values. Next, any remaining value which differs from this new average by more than 5 is eliminated. If no values remain, a −1 is stored in the data file ("O3DATA"). Otherwise, the average is again recalculated, minus the eliminated values, and this final average "w/o outliers" is stored in the file. The final average is the value that is reported for total column ozone. Normally, for clear sky conditions, no values are eliminated as outliers once the initial trimming process is complete, and both averages are the same.

Future work may be done to provide statistical support and enhancements for the heuristic averaging technique just described. For example "robust statistical methods" are known to deal adequately with data containing large outliers that have an extreme affect on estimated results. As alluded to above, large outliers can occur in this instrument when a rapidly moving light cloud, or other variation, changes the optical density of the atmosphere between successive scans of the same measurement. The next section will quantify overall instrument performance, which validates the effectiveness of the heuristic noise reduction technique.

Instrument Performance Verification. The UNT ozone instrument was initially calibrated against the MICROTOPS II (S/N 5348) hand held ozone instrument, which was calibrated in Mauna Loa, Hi. on Oct. 18, 2004 (valid until Oct. 18, 2005) by the Solar Light Company. Side by side measurements were taken in Denton, Texas, on the UNT campus, with the UNT instrument and the MICROTOPS II hand held ozone meter, for comparison of results and verification. The MICROTOPS II has been reported to be capable of providing quality ozone data (within 1% of Dobson and Brewer instruments) for low values of air mass (large solar elevation angles) and clear sky conditions. The deviation with respect to reference instruments is reported to increase to 2-3% for high values of air mass and hazy sky conditions. Therefore, MICROTOPS II comparisons were done at a time of day with low airmass and cloudless and haze-free (as much as possible) sky conditions.

For further comparison and validation, ozone data was also recorded from the Earth Probe Total Ozone Mapping Spectrometer ("EP/TOMS") satellite, launched and maintained by NASA. EP/TOMS is in sun-synchronous orbit at an altitude of 740 km, inclination of 98.385°, and 99.65 minute period and has a field of view of 39 km. EP/TOMS orbits the earth just over 14 times per day with a local equator crossing time (ALECT) of 10:47 a.m., standard local time. Accounting for the latitude difference at the University of North Texas, the UNT flyover time was calculated to be 10:56 a.m. CST (11:56 a.m. CDT).

These comparisons serve as verification and validation for the new ozone instrument in lieu of more rigorous collocation experiments with standards such as the Dobson and Brewer instruments. If future project funding is obtained, collocation studies would provide a superior validation of the design. RMS (Root Mean Squared) error techniques have been employed to determine precision and accuracy of the new instrument.

Instrument Accuracy. Data collection for the UNT system began Nov. 6, 2004 using initial Langley calibration data taken on the same day. After collecting data for the period Nov. 6, 2004 through Jul. 23, 2005, it was observed that the MICROTOPS II ozone results were drifting downward relative to both TOMS and the UNT system. Table 10 contains ozone data comparing MICROTOPS II and TOMS for this period. Considering TOMS data to be the base value, the percent error was calculated and tabulated for MICROTOPS II. FIG. 20 is a plot of the ozone data (top) and percent error (bottom).

TABLE 10

Comparison of TOMS and MICROTOPS II (S/N 5348)

| Date | TOMS (DU) | MICROTOPS (DU) | % Error |
|---|---|---|---|
| Nov. 6, 2004 | 242.0 | 248.2 | 2.6 |
| Nov. 24, 2004 | 287.0 | 293.0 | 2.1 |
| Nov. 30, 2004 | 251.0 | 260.5 | 3.8 |
| Dec. 1, 2004 | 229.0 | 248.8 | 8.6 |
| Dec. 2, 2004 | 238.0 | 241.5 | 1.5 |
| Dec. 3, 2004 | 250.0 | 259.8 | 3.9 |
| Jan. 13, 2005 | 309.0 | 320.4 | 3.7 |
| Jan. 14, 2005 | 300.0 | 311.0 | 3.7 |
| Jan. 17, 2005 | 285.0 | 293.8 | 3.1 |
| Jan. 19, 2005 | 289.0 | 296.9 | 2.7 |
| Jan. 20, 2005 | 279.0 | 277.0 | −0.7 |
| Jan. 21, 2005 | 282.0 | 287.3 | 1.9 |
| Jan. 22, 2005 | 292.0 | 295.5 | 1.2 |
| Jan. 24, 2005 | 258.0 | 259.5 | 0.6 |
| Jan. 25, 2005 | 243.0 | 253.1 | 4.2 |
| Jan. 26, 2005 | 265.0 | 265.6 | 0.2 |
| Feb. 3, 2005 | 277.0 | 271.5 | −2.0 |
| Feb. 4, 2005 | 245.0 | 259.5 | 5.9 |
| Feb. 14, 2005 | 289.0 | 285.6 | −1.2 |
| Feb. 15, 2005 | 271.0 | 267.2 | −1.4 |
| Feb. 21, 2005 | 298.0 | 293.7 | −1.4 |
| Feb. 22, 2005 | 300.0 | 291.5 | −2.8 |
| Feb. 28, 2005 | 318.0 | 306.6 | −3.6 |
| Mar. 7, 2005 | 308.0 | 303.3 | −1.5 |
| Mar. 8, 2005 | 315.0 | 321.7 | 2.1 |
| Mar. 9, 2005 | 351.0 | 361.6 | 3.0 |
| Mar. 10, 2005 | 321.0 | 302.8 | −5.7 |
| Mar. 11, 2005 | 309.0 | 305.1 | −1.3 |
| Mar. 14, 2005 | 298.0 | 278.7 | −6.5 |
| Mar. 21, 2005 | 309.0 | 315.3 | 2.0 |
| Mar. 23, 2005 | 336.0 | 312.2 | −7.1 |
| Mar. 24, 2005 | 332.0 | 317.9 | −4.2 |
| Mar. 30, 2005 | 321.0 | 302.6 | −5.7 |
| Apr. 7, 2005 | 329.0 | 290.6 | −11.7 |
| Apr. 8, 2005 | 280.0 | 269.0 | −3.9 |
| Apr. 11, 2005 | 336.0 | 324.6 | −3.4 |
| Apr. 12, 2005 | 301.0 | 287.3 | −4.6 |
| Apr. 14, 2005 | 316.0 | 298.1 | −5.7 |
| Apr. 22, 2005 | 295.0 | 279.0 | −5.4 |
| Apr. 23, 2005 | 297.0 | 290.4 | −2.2 |
| Apr. 26, 2005 | 342.0 | 322.0 | −5.8 |
| Apr. 27, 2005 | 332.0 | 317.0 | −4.5 |
| Apr. 28, 2005 | 322.0 | 300.5 | −6.7 |
| May 11, 2005 | 301.0 | 285.3 | −5.2 |
| May 14, 2005 | 327.0 | 302.8 | −7.4 |
| May 17, 2005 | 315.0 | 290.4 | −7.8 |
| May 19, 2005 | 302.0 | 266.9 | −11.6 |
| May 20, 2005 | 297.0 | 262.6 | −11.6 |
| May 24, 2005 | 321.0 | 299.0 | −6.9 |
| May 27, 2005 | 324.0 | 294.4 | −9.1 |
| Jun. 1, 2005 | 364.0 | 313.5 | −13.9 |
| Jun. 2, 2005 | 331.0 | 298.6 | −9.8 |
| Jun. 6, 2005 | 314.0 | 287.1 | −8.6 |
| Jun. 7, 2005 | 302.0 | 284.7 | −5.7 |
| Jun. 9, 2005 | 318.0 | 284.9 | −10.4 |
| Jun. 10, 2005 | 307.0 | 275.0 | −10.4 |
| Jun. 11, 2005 | 308.0 | 278.1 | −9.7 |
| Jun. 13, 2005 | 308.0 | 283.6 | −7.9 |
| Jun. 14, 2005 | 290.0 | 281.6 | −2.9 |
| Jun. 15, 2005 | 299.0 | 277.3 | −7.3 |
| Jun. 16, 2005 | 302.0 | 276.3 | −8.5 |
| Jun. 17, 2005 | 304.0 | 286.8 | −5.7 |
| Jun. 20, 2005 | 319.0 | 297.9 | −6.6 |
| Jun. 21, 2005 | 307.0 | 284.1 | −7.5 |
| Jun. 22, 2005 | 305.0 | 277.8 | −8.9 |
| Jun. 23, 2005 | 307.0 | 276.6 | −9.9 |
| Jun. 24, 2005 | 313.0 | 274.4 | −12.3 |
| Jun. 25, 2005 | 310.0 | 274.3 | −11.5 |
| Jun. 27, 2005 | 303.0 | 266.9 | −11.9 |
| Jun. 28, 2005 | 291.0 | 258.1 | −11.3 |
| Jun. 29, 2005 | 284.0 | 247.8 | −12.7 |
| Jun. 30, 2005 | 283.0 | 248.5 | −12.2 |
| Jul. 4, 2005 | 299.0 | 263.5 | −11.9 |
| Jul. 8, 2005 | 318.0 | 291.1 | −8.4 |
| Jul. 14, 2005 | 318.0 | 281.6 | −11.4 |
| Jul. 20, 2005 | 301.0 | 262.2 | −12.9 |
| Jul. 21, 2005 | 303.0 | 255.5 | −15.7 |
| Jul. 22, 2005 | 298.0 | 260.7 | −12.5 |
| Jul. 23, 2005 | 302.0 | 258.2 | −14.5 |

As shown in FIG. 20, the MICROTOPS II unit (S/N 5348) was drifting downward from the very onset of data collection in November 2004. Based upon this continued trend, it was not possible to use the MICROTOPS II for determining the precision or accuracy of the UNT system.

EP/'TOMS ozone data thus became the standard for comparison. Table 11 and FIG. 21 contain ozone data and graphs for both UNT and TOMS instruments for the period starting Nov. 6, 2004 and extending through Oct. 4, 2005. FIG. 21 contains graphs for ozone data for both systems and a plot of the error between the two. Initially the UNT system produced ozone readings that were consistently about 5-10% below TOMS values. Then, upon recalibration of the UNT system on Feb. 14, 2005, the error was reduced substantially. The first calibration done in November 2004 used "ideal" wavelengths read directly from the spectrometer as compared to calculating "effective wavelengths." This resulted in consistently low readings for the UNT system until the recalibration on Feb. 14, 2005. All subsequent calibrations used effective wavelengths determined from slopes of Langley plots in accordance with the procedures documented in this report. As a result, the error was reduced, typically in the range of 0-3% with occasional errors in the 5-7% range. The maximum errors (after the Feb. 14, 2005 calibration) were +4.8% and −7.7%.

TABLE 11

Comparison of TOMS and UNT

| Date | TOMS (DU) | UNT (DU) | % Error |
|---|---|---|---|
| Nov. 6, 2004 | 242.0 | 221.0 | −8.7 |
| Nov. 24, 2004 | 287.0 | 259.8 | −9.5 |
| Nov. 30, 2004 | 251.0 | 242.8 | −3.3 |
| Dec. 1, 2004 | 229.0 | 226.7 | −1.0 |
| Dec. 2, 2004 | 238.0 | 224.8 | −5.5 |
| Dec. 3, 2004 | 250.0 | 245.3 | −1.9 |
| Jan. 13, 2005 | 309.0 | 296.9 | −3.9 |
| Jan. 14, 2005 | 300.0 | 291.6 | −2.8 |
| Jan. 17, 2005 | 285.0 | 272.5 | −4.4 |
| Jan. 19, 2005 | 289.0 | 262.1 | −9.3 |
| Jan. 20, 2005 | 279.0 | 254.0 | −9.0 |
| Jan. 21, 2005 | 282.0 | 267.0 | −5.3 |
| Jan. 22, 2005 | 292.0 | 265.1 | −9.2 |
| Jan. 24, 2005 | 258.0 | 235.1 | −8.9 |
| Jan. 25, 2005 | 243.0 | 218.3 | −10.2 |
| Jan. 26, 2005 | 265.0 | 233.2 | −12.0 |
| Feb. 3, 2005 | 277.0 | 256.6 | −7.4 |
| Feb. 4, 2005 | 245.0 | 248.2 | 1.3 |
| Feb. 14, 2005 | 289.0 | 299.0 | 3.5 |
| Feb. 15, 2005 | 271.0 | 271.2 | 0.1 |
| Feb. 21, 2005 | 298.0 | 300.6 | 0.9 |
| Feb. 22, 2005 | 300.0 | 293.1 | −2.3 |
| Feb. 28, 2005 | 318.0 | 311.6 | −2.0 |
| Mar. 7, 2005 | 308.0 | 302.2 | −1.9 |
| Mar. 8, 2005 | 315.0 | 321.7 | 2.1 |
| Mar. 9, 2005 | 351.0 | 368.0 | 4.8 |
| Mar. 10, 2005 | 321.0 | 304.2 | −5.2 |

TABLE 11-continued

Comparison of TOMS and UNT

| Date | TOMS (DU) | UNT (DU) | % Error |
|---|---|---|---|
| Mar. 11, 2005 | 309.0 | 304.8 | −1.4 |
| Mar. 14, 2005 | 298.0 | 289.0 | −3.0 |
| Mar. 21, 2005 | 309.0 | 322.6 | 4.4 |
| Mar. 23, 2005 | 336.0 | 321.0 | −4.5 |
| Mar. 24, 2005 | 332.0 | 333.5 | 0.4 |
| Mar. 30, 2005 | 321.0 | 315.8 | −1.6 |
| Apr. 7, 2005 | 329.0 | 318.9 | −3.1 |
| Apr. 8, 2005 | 280.0 | 266.4 | −4.9 |
| Apr. 11, 2005 | 336.0 | 346.6 | 3.2 |
| Apr. 12, 2005 | 301.0 | 302.7 | 0.6 |
| Apr. 13, 2005 | 307.0 | 300.8 | −2.0 |
| Apr. 14, 2005 | 316.0 | 309.0 | −2.2 |
| Apr. 22, 2005 | 295.0 | 291.0 | −1.4 |
| Apr. 23, 2005 | 297.0 | 303.7 | 2.3 |
| Apr. 26, 2005 | 342.0 | 342.2 | 0.1 |
| Apr. 27, 2005 | 332.0 | 324.8 | −2.2 |
| Apr. 28, 2005 | 322.0 | 314.5 | −2.3 |
| May 11, 2005 | 301.0 | 307.3 | 2.1 |
| May 14, 2005 | 327.0 | 320.3 | −2.0 |
| May 17, 2005 | 315.0 | 313.3 | −0.5 |
| May 19, 2005 | 302.0 | 298.1 | −1.3 |
| May 20, 2005 | 297.0 | 285.5 | −3.9 |
| May 24, 2005 | 321.0 | 310.2 | −3.4 |
| May 27, 2005 | 324.0 | 304.8 | −5.9 |
| Jun. 1, 2005 | 364.0 | 351.1 | −3.5 |
| Jun. 2, 2005 | 331.0 | 321.8 | −2.8 |
| Jun. 6, 2005 | 314.0 | 299.1 | −4.7 |
| Jun. 7, 2005 | 302.0 | 290.1 | −3.9 |
| Jun. 9, 2005 | 318.0 | 303.4 | −4.6 |
| Jun. 10, 2005 | 307.0 | 283.3 | −7.7 |
| Jun. 11, 2005 | 308.0 | 287.2 | −6.8 |
| Jun. 13, 2005 | 308.0 | 292.3 | −5.1 |
| Jun. 14, 2005 | 290.0 | 292.8 | 1.0 |
| Jun. 15, 2005 | 299.0 | 286.5 | −4.2 |
| Jun. 16, 2005 | 302.0 | 293.1 | −2.9 |
| Jun. 17, 2005 | 304.0 | 305.2 | 0.4 |
| Jun. 20, 2005 | 319.0 | 318.0 | −0.3 |
| Jun. 21, 2005 | 307.0 | 293.4 | −4.4 |
| Jun. 22, 2005 | 305.0 | 294.8 | −3.3 |
| Jun. 23, 2005 | 307.0 | 294.3 | −4.1 |
| Jun. 24, 2005 | 313.0 | 300.3 | −4.1 |
| Jun. 25, 2005 | 310.0 | 306.0 | −1.3 |
| Jun. 27, 2005 | 303.0 | 290.8 | −4.0 |
| Jun. 28, 2005 | 291.0 | 281.8 | −3.2 |
| Jun. 29, 2005 | 284.0 | 275.4 | −3.0 |
| Jun. 30, 2005 | 283.0 | 279.9 | −1.1 |
| Jul. 4, 2005 | 299.0 | 288.5 | −3.5 |
| Jul. 8, 2005 | 318.0 | 313.4 | −1.4 |
| Jul. 12, 2005 | 304.0 | 301.6 | −0.8 |
| Jul. 14, 2005 | 318.0 | 311.7 | −2.0 |
| Jul. 20, 2005 | 301.0 | 295.7 | −1.8 |
| Jul. 21, 2005 | 303.0 | 280.2 | −7.5 |
| Jul. 22, 2005 | 298.0 | 294.1 | −1.3 |
| Jul. 23, 2005 | 302.0 | 287.4 | −4.8 |
| Jul. 25, 2005 | 291.0 | 280.8 | −3.5 |
| Jul. 26, 2005 | 289.0 | 283.6 | −1.9 |
| Jul. 29, 2005 | 288.0 | 286.6 | −0.5 |
| Aug. 1, 2005 | 295.0 | 282.6 | −4.2 |
| Aug. 2, 2005 | 302.0 | 287.2 | −4.9 |
| Aug. 3, 2005 | 300.0 | 291.5 | −2.8 |
| Aug. 11, 2005 | 291.0 | 291.1 | 0.0 |
| Aug. 13, 2005 | 290.0 | 287.8 | −0.8 |
| Aug. 17, 2005 | 279.0 | 278.4 | −0.2 |
| Aug. 18, 2005 | 279.0 | 279.9 | 0.3 |
| Aug. 19, 2005 | 288.0 | 292.6 | 1.6 |
| Aug. 20, 2005 | 293.0 | 294.1 | 0.4 |
| Aug. 29, 2005 | 289.0 | 295.1 | 2.1 |
| Aug. 30, 2005 | 297.0 | 306.1 | 3.1 |
| Aug. 31, 2005 | 283.0 | 296.2 | 4.7 |
| Sep. 1, 2005 | 287.0 | 293.0 | 2.1 |
| Sep. 3, 2005 | 289.0 | 291.6 | 0.9 |
| Sep. 5, 2005 | 288.0 | 295.5 | 2.6 |
| Sep. 6, 2005 | 284.0 | 284.9 | 0.3 |
| Sep. 8, 2005 | 288.0 | 273.3 | −5.1 |
| Sep. 9, 2005 | 287.0 | 280.7 | −2.2 |
| Sep. 13, 2005 | 274.0 | 266.5 | −2.7 |
| Sep. 14, 2005 | 265.0 | 253.4 | −4.4 |
| Sep. 19, 2005 | 259.0 | 257.1 | −0.7 |
| Sep. 20, 2005 | 260.0 | 256.8 | −1.2 |
| Sep. 21, 2005 | 264.0 | 260.1 | −1.5 |
| Sep. 22, 2005 | 261.0 | 261.0 | 0.0 |
| Sep. 26, 2005 | 243.0 | 251.9 | 3.7 |
| Sep. 27, 2005 | 258.0 | 251.0 | −2.7 |
| Sep. 28, 2005 | 261.0 | 258.8 | −0.8 |
| Oct. 4, 2005 | 256.0 | 253.6 | −0.9 |

In order to quantify the difference between the UNT system and TOMS, the root mean square error (RMS) was calculated for the data in Table 11, beginning on Feb. 14, 2005. Taking the TOMS value as the "truth," designated $X(t_i)$, and the UNT system reading as the estimated value, designated $\hat{X}(t_i)$, the error for one set of ozone readings is calculated as $$e(t_i) = X(t_i) - \hat{X}(t_i) \qquad (40)$$

where $t_i$ indicates a specific time (a single row in Table 11). The squared error for a particular pair of readings is then $$e^2(t_i) = \left(X(t_i) - \hat{X}(t_i)\right)^2 \qquad (41)$$

and the total squared error for all "n" ozone pairs being compared is $$E = \sum_{i=1}^{n} e^2(t_i). \qquad (42)$$

Now the RMS error is $$\text{RMS}(e) = \sqrt{\frac{E}{n}} = \sqrt{\frac{\sum_{i=1}^{n} e^2(t_i)}{n}} \qquad (43)$$

The RMS error for the UNT system ozone readings given in Table 11 has been calculated and is tabulated in Table 12. Tabl3 12 is an Excel® spreadsheet which calculates daily, total, and RMS error, per the above equations. The RMS error for the period Feb. 14, 2005 through Oct. 4, 2005 is shown to be 9.56 DU. The average daily ozone reading for this same period is 300.1 DU which gives an overall percentage error of 3.19%. Thus ±3.19% is the current RMS accuracy of the UNT system, when compared to EP/TOMS.

TABLE 12

Calculation of RMS error

| n | $X(t_i)$ | $X(t_i)$ hat | $e(t_i)$ | $e^2(t_i)$ |
|---|---|---|---|---|
| 1 | 289.0 | 299.0 | 10.0 | 100.0 |
| 2 | 271.0 | 271.2 | 0.2 | 0.1 |

TABLE 12-continued

Calculation of RMS error

| n | $X(t_i)$ | $X(t_i)$ hat | $e(t_i)$ | $e^2(t_i)$ |
|---|---|---|---|---|
| 3 | 298.0 | 300.6 | 2.6 | 6.8 |
| 4 | 300.0 | 293.1 | −6.9 | 47.9 |
| 5 | 318.0 | 311.6 | −6.4 | 41.0 |
| 6 | 308.0 | 302.2 | −5.8 | 33.6 |
| 7 | 315.0 | 321.7 | 6.7 | 44.9 |
| 8 | 351.0 | 368.0 | 17.0 | 289.0 |
| 9 | 321.0 | 304.2 | −16.8 | 282.2 |
| 10 | 309.0 | 304.8 | −4.2 | 17.6 |
| 11 | 298.0 | 289.0 | −9.0 | 81.0 |
| 12 | 309.0 | 322.6 | 13.6 | 183.6 |
| 13 | 336.0 | 321.0 | −15.0 | 225.0 |
| 14 | 332.0 | 333.5 | 1.5 | 2.2 |
| 15 | 321.0 | 315.8 | −5.2 | 27.0 |
| 16 | 329.0 | 318.9 | −10.1 | 102.0 |
| 17 | 280.0 | 266.4 | −13.6 | 185.0 |
| 18 | 336.0 | 346.6 | 10.6 | 112.4 |
| 19 | 301.0 | 302.7 | 1.7 | 2.9 |
| 20 | 307.0 | 300.8 | −6.2 | 38.4 |
| 21 | 316.0 | 309.0 | −7.0 | 49.0 |
| 22 | 295.0 | 291.0 | −4.0 | 16.0 |
| 23 | 297.0 | 303.7 | 6.7 | 44.9 |
| 24 | 342.0 | 342.2 | 0.2 | 0.0 |
| 25 | 332.0 | 324.8 | −7.2 | 51.8 |
| 26 | 322.0 | 314.5 | −7.5 | 56.3 |
| 27 | 301.0 | 307.3 | 6.3 | 39.7 |
| 28 | 327.0 | 320.3 | −6.7 | 44.9 |
| 29 | 315.0 | 313.3 | −1.7 | 2.9 |
| 30 | 302.0 | 298.1 | −3.9 | 15.2 |
| 31 | 297.0 | 285.5 | −11.5 | 132.3 |
| 32 | 321.0 | 310.2 | −10.8 | 116.6 |
| 33 | 324.0 | 304.8 | −19.2 | 368.6 |
| 34 | 364.0 | 351.1 | −12.9 | 166.4 |
| 35 | 331.0 | 321.8 | −9.2 | 84.6 |
| 36 | 314.0 | 299.1 | −14.9 | 222.0 |
| 37 | 302.0 | 290.1 | −11.9 | 141.6 |
| 38 | 318.0 | 303.4 | −14.6 | 213.2 |
| 39 | 307.0 | 283.3 | −23.7 | 561.7 |
| 40 | 308.0 | 287.2 | −20.8 | 432.6 |
| 41 | 308.0 | 292.3 | −15.7 | 246.5 |
| 42 | 290.0 | 292.8 | 2.8 | 7.8 |
| 43 | 299.0 | 286.5 | −12.5 | 156.3 |
| 44 | 302.0 | 293.1 | −8.9 | 79.2 |
| 45 | 304.0 | 305.2 | 1.2 | 1.4 |
| 47 | 307.0 | 293.4 | −13.6 | 185.0 |
| 48 | 305.0 | 294.8 | −10.2 | 104.0 |
| 49 | 307.0 | 294.3 | −12.7 | 161.3 |
| 50 | 313.0 | 300.3 | −12.7 | 161.3 |
| 51 | 310.0 | 306.0 | −4.0 | 16.0 |
| 52 | 303.0 | 290.8 | −12.2 | 148.8 |
| 53 | 291.0 | 281.8 | −9.2 | 84.6 |
| 54 | 284.0 | 275.4 | −8.6 | 74.0 |
| 55 | 283.0 | 279.9 | −3.1 | 9.6 |
| 56 | 299.0 | 288.5 | −10.5 | 110.3 |
| 57 | 318.0 | 313.4 | −4.6 | 21.2 |
| 58 | 304.0 | 301.6 | −2.4 | 5.8 |
| 59 | 318.0 | 311.7 | −6.3 | 39.7 |
| 60 | 301.0 | 295.7 | −5.3 | 28.1 |
| 61 | 303.0 | 280.2 | −22.8 | 519.8 |
| 62 | 298.0 | 294.1 | −3.9 | 15.2 |
| 63 | 302.0 | 287.4 | −14.6 | 213.2 |
| 64 | 291.0 | 280.8 | −10.2 | 104.0 |
| 65 | 289.0 | 283.6 | −5.4 | 29.2 |
| 66 | 288.0 | 286.6 | −1.4 | 2.0 |
| 67 | 295.0 | 282.6 | −12.4 | 153.8 |
| 68 | 302.0 | 287.2 | −14.8 | 219.0 |
| 69 | 300.0 | 291.5 | −8.5 | 72.3 |
| 70 | 291.0 | 291.1 | 0.1 | 0.0 |
| 71 | 290.0 | 287.8 | −2.2 | 4.8 |
| 72 | 279.0 | 278.4 | −0.6 | 0.4 |
| 73 | 279.0 | 279.9 | 0.9 | 0.8 |
| 74 | 288.0 | 292.6 | 4.6 | 21.2 |
| 75 | 293.0 | 294.1 | 1.1 | 1.2 |
| 76 | 289.0 | 295.1 | 6.1 | 37.2 |
| 77 | 297.0 | 306.1 | 9.1 | 82.8 |
| 78 | 283.0 | 296.2 | 13.2 | 174.2 |
| 79 | 287.0 | 293.0 | 6.0 | 36.0 |
| 80 | 289.0 | 291.6 | 2.6 | 6.8 |
| 81 | 288.0 | 295.5 | 7.5 | 56.3 |
| 82 | 284.0 | 284.9 | 0.9 | 0.8 |
| 83 | 288.0 | 273.3 | −14.7 | 216.1 |
| 84 | 287.0 | 280.7 | −6.3 | 39.7 |
| 85 | 274.0 | 266.5 | −7.5 | 56.3 |
| 86 | 265.0 | 253.4 | −11.6 | 134.6 |
| 87 | 259.0 | 257.1 | −1.9 | 3.6 |
| 88 | 260.0 | 256.8 | −3.2 | 10.2 |
| 89 | 264.0 | 260.1 | −3.9 | 15.2 |
| 90 | 261.0 | 261.0 | 0.0 | 0.0 |
| 91 | 243.0 | 251.9 | 8.9 | 79.2 |
| 92 | 258.0 | 251.0 | −7.0 | 49.0 |
| 93 | 261.0 | 258.8 | −2.2 | 4.8 |
| 94 | 256.0 | 253.6 | −2.4 | 5.8 |
| ave. O3 | 300.1 | total squared error | | 8590.1 |
| | | RMS error (DU) | | 9.56 |
| | | % Error | | 3.19 |

Precision, as it applies to measuring devices and instruments, is a measure of the instrument's repeatability when making multiple readings of the same quantity. Thus an accurate instrument will inherently have good precision, but good precision does not necessarily imply high accuracy. In order to study the precision of this instrument, a modification was made to the script program. The script program dictates when ozone data is collected and, for this test, was set to collect data continuously during the hours of 11:45 a.m. to 1:45 p.m. Assuming that total column ozone was constant during this period of time, this provided multiple measurements of the same ozone value, so that precision could be determined. The assumption of constant ozone is subject to error on days when strong fronts are passing through, so these days were avoided.

Table 13 contains data taken on three separate days that were used to calculate precision. The highest imprecision, obtained on Oct. 24, 2005, was ±2.3%. The fact that total column ozone may actually vary a few percent during the data collection time, casts some doubt on the accuracy of this method for calculating precision. Not being collocated with another instrument of known high accuracy, this is about the best that can be done. This method probably yields a worst-case scenario.

TABLE 13

Ozone (DU) 10:45 a.m. to 1:45 p.m.

| Oct. 20, 2005 | Oct. 24, 2005 | Oct. 25, 2005 |
|---|---|---|
| 254.8 | 314.8 | 293.1 |
| 251.5 | 316.5 | 295.0 |
| 251.2 | 314.9 | 293.1 |
| 252.9 | 306.8 | 293.1 |
| 247.7 | 309.3 | 291.9 |
| 250.8 | 306.5 | 293.1 |
| 249.2 | 306.5 | 293.8 |
| 252.5 | 309.9 | 293.4 |
| 249.4 | 312.3 | 293.5 |
| 251.3 | 309.6 | 293.3 |
| 250.1 | 304.5 | 292.3 |
| 249.6 | 302.3 | 294.6 |
| 250.6 | 303.1 | 288.9 |
| 250.0 | 307.0 | 291.8 |
| 252.1 | 307.2 | 291.7 |
| 253.3 | 308.4 | 293.2 |
| 248.0 | 311.0 | 295.0 |
| 251.8 | 312.7 | 292.2 |

TABLE 13-continued

Ozone (DU) 10:45 a.m. to 1:45 p.m.

|  | Oct. 20, 2005 | Oct. 24, 2005 | Oct. 25, 2005 |
|---|---|---|---|
|  | 251.1 | 313.8 | 292.1 |
| MIN | 247.7 | 302.3 | 288.9 |
| MAX | 254.8 | 316.5 | 295.0 |
| AVE | 250.9 | 309.3 | 292.9 |
| Precision (+ %) | 1.5 | 2.3 | 0.7 |
| Precision (− %) | 1.3 | 2.3 | 1.4 |

Sensitivity Analysis. Analyses were done to quantify sensitivity of the ozone equation to parameter variation. The purpose was to determine the variables for which a small error affects the result. The end goal was to employ this understanding to minimize effects of the sensitive variables. This analysis was done using a Quick BASIC program specifically written for this purpose. The actual ozone equation was implemented and realistic parameter values were input to and/or calculated by the program. A loop incrementally varied each parameter in the ozone equation, one at a time. The parameter and resulting ozone value were stored for each pass through the loop. This data was then read into a spreadsheet (Table 14-Table 16) where sensitivity was calculated in %/% and graphs were plotted showing the effect of each parameter on calculated ozone (FIG. 22-FIG. 30).

All sensitivity graphs have the same ordinate variable and scale. Though each graph has a different variable on the abscissa, plausible ranges were selected so that a realistic indication of sensitivity is discernable via the slope of the graph. For example, elevation angle was allowed to vary plus and minus two degrees. This range includes the possible error limits of the solar position equations, but the range is not so large as to falsely lower the slope of the sensitivity line. Extraterrestrial constants were each varied by about plus and minus 25% (a fairly wide band due to multiple possible error sources when collecting Langley data), and wavelengths were varied by about plus and minus 0.3% each (about 1 nm).

TABLE 14

Ozone equation sensitivity to pressure, altitude, and solar elevation

| Pressure (mbar) | OZONE | %/% | altitude (km) | OZONE | %/% | solar elev. angle | OZONE | %/% |
|---|---|---|---|---|---|---|---|---|
| 900 | 305.8 | −0.03 | 0.10 | 304.9 | 0.00 | 41.00 | 293.2 | 0.83 |
| 910 | 305.7 | −0.03 | 0.12 | 304.9 | 0.00 | 41.25 | 294.7 | 0.82 |
| 920 | 305.7 | −0.03 | 0.14 | 304.9 | 0.00 | 41.50 | 296.2 | 0.82 |
| 930 | 305.6 | −0.03 | 0.16 | 304.9 | 0.00 | 41.75 | 297.6 | 0.82 |
| 940 | 305.5 | −0.03 | 0.18 | 304.9 | 0.00 | 42.00 | 299.1 | 0.82 |
| 950 | 305.4 | −0.03 | 0.20 | 304.9 | * | 42.25 | 300.6 | 0.82 |
| 960 | 305.3 | −0.03 | 0.22 | 304.9 | 0.00 | 42.50 | 302.0 | 0.82 |
| 970 | 305.3 | −0.03 | 0.24 | 304.9 | 0.00 | 42.75 | 303.5 | 0.82 |
| 980 | 305.2 | −0.03 | 0.26 | 304.9 | 0.00 | 43.00 | 304.9 | * |
| 990 | 305.1 | −0.03 | 0.28 | 304.9 | 0.00 | 43.25 | 306.4 | 0.81 |
| 1000 | 305.0 | −0.03 | 0.30 | 304.9 | 0.00 | 43.50 | 307.8 | 0.81 |
| 1010 | 305.0 | * |  |  |  | 43.75 | 309.2 | 0.81 |
| 1020 | 304.9 | −0.03 |  |  |  | 44.00 | 310.7 | 0.81 |
| 1030 | 304.8 | −0.03 |  |  |  | 44.25 | 312.1 | 0.81 |
| 1040 | 304.7 | −0.03 |  |  |  | 44.50 | 313.5 | 0.80 |
| 1050 | 304.6 | −0.03 |  |  |  | 44.75 | 314.9 | 0.80 |
| 1060 | 304.6 | −0.03 |  |  |  | 45.00 | 316.3 | 0.80 |
| 1070 | 304.5 | −0.03 |  |  |  |  |  |  |
| 1080 | 304.4 | −0.03 |  |  |  |  |  |  |
| 1090 | 304.3 | −0.03 |  |  |  |  |  |  |
| 1100 | 304.3 | −0.03 |  |  |  |  |  |  |

*indicates nominal value

TABLE 15

Ozone equation sensitivity to extraterrestrial constants (ET)

| Io1 (ET 1) | OZONE | %/% | Io2 (ET 2) | OZONE | %/% | Io3 (ET 3) | OZONE | %/% |
|---|---|---|---|---|---|---|---|---|
| 30000 | 151.3 | 1.87 | 9000 | 609.4 | −3.65 | 5500 | 144.9 | 1.86 |
| 31000 | 167.3 | 1.84 | 9250 | 582.7 | −3.60 | 5700 | 162.3 | 1.82 |
| 32000 | 182.7 | 1.81 | 9500 | 556.8 | −3.55 | 5900 | 179.0 | 1.79 |
| 33000 | 197.7 | 1.78 | 9750 | 531.6 | −3.51 | 6100 | 195.2 | 1.77 |
| 34000 | 212.2 | 1.76 | 10000 | 506.9 | −3.47 | 6300 | 210.9 | 1.74 |
| 35000 | 226.3 | 1.73 | 10250 | 482.9 | −3.43 | 6500 | 226.1 | 1.71 |
| 36000 | 239.9 | 1.71 | 10500 | 459.5 | −3.39 | 6700 | 240.8 | 1.69 |
| 37000 | 253.3 | 1.69 | 10750 | 436.7 | −3.35 | 6900 | 255.1 | 1.66 |
| 38000 | 266.2 | 1.66 | 11000 | 414.3 | −3.31 | 7100 | 269.0 | 1.64 |
| 39000 | 278.8 | 1.64 | 11250 | 392.5 | −3.27 | 7300 | 282.5 | 1.62 |
| 40000 | 291.2 | 1.62 | 11500 | 371.1 | −3.24 | 7500 | 295.6 | 1.60 |
| 41000 | 303.2 | * | 11750 | 350.2 | −3.20 | 7700 | 308.4 | * |
| 42000 | 314.9 | 1.58 | 12000 | 329.7 | −3.17 | 7900 | 320.9 | 1.56 |
| 43000 | 326.3 | 1.57 | 12250 | 309.7 | * | 8100 | 333.0 | 1.54 |
| 44000 | 337.5 | 1.55 | 12500 | 290.1 | −3.11 | 8300 | 344.9 | 1.52 |
| 45000 | 348.4 | 1.53 | 12750 | 270.8 | −3.08 | 8500 | 356.5 | 1.50 |

TABLE 15-continued

Ozone equation sensitivity to extraterrestrial constants (ET)

| Io1 (ET 1) | OZONE | %/% | Io2 (ET 2) | OZONE | %/% | Io3 (ET 3) | OZONE | %/% |
|---|---|---|---|---|---|---|---|---|
| 46000 | 359.1 | 1.51 | 13000 | 251.9 | −3.05 | 8700 | 367.8 | 1.48 |
| 47000 | 369.5 | 1.50 | 13250 | 233.4 | −3.02 | 8900 | 378.8 | 1.46 |
| 48000 | 379.8 | 1.48 | 13500 | 215.2 | −2.99 | 9100 | 389.6 | 1.45 |
| 49000 | 389.8 | 1.46 | 13750 | 197.4 | −2.96 | 9300 | 400.2 | 1.43 |
| 50000 | 399.6 | 1.45 | 14000 | 179.9 | −2.93 | 9500 | 410.5 | 1.42 |
|  |  |  | 14250 | 162.7 | −2.91 |  |  |  |
|  |  |  | 14500 | 145.8 | −2.88 |  |  |  |
|  |  |  | 14750 | 129.2 | −2.86 |  |  |  |
|  |  |  | 15000 | 112.8 | −2.83 |  |  |  |

*indicates nominal value

TABLE 16

Ozone equation sensitivity to wavelength

| Iam1 | OZONE | %/% | Iam2 | OZONE | %/% | Iam3 | OZONE | %/% |
|---|---|---|---|---|---|---|---|---|
| 305.0 | 203.4 | 109.13 | 310.5 | 621.4 | −302.18 | 316.0 | 271.2 | 38.14 |
| 305.1 | 211.6 | 112.39 | 310.6 | 566.3 | −275.27 | 316.1 | 274.8 | 38.30 |
| 305.2 | 220.4 | 115.83 | 310.7 | 520.2 | −252.78 | 316.2 | 278.4 | 38.46 |
| 305.3 | 229.7 | 119.49 | 310.8 | 481.1 | −233.71 | 316.3 | 282.0 | 38.62 |
| 305.4 | 239.6 | 123.38 | 310.9 | 447.4 | −217.32 | 316.4 | 285.7 | 38.78 |
| 305.5 | 250.3 | 127.53 | 311.0 | 418.2 | −203.09 | 316.5 | 289.4 | 38.95 |
| 305.6 | 261.6 | 131.95 | 311.1 | 392.6 | −190.62 | 316.6 | 293.1 | 39.11 |
| 305.7 | 273.8 | 136.68 | 311.2 | 370.0 | −179.60 | 316.7 | 296.9 | 39.26 |
| 305.8 | 286.8 | 141.74 | 311.3 | 349.8 | −169.79 | 316.8 | 300.7 | 39.42 |
| 305.9 | 300.9 | 147.28 | 311.4 | 331.7 | −161.06 | 316.9 | 304.5 | 39.60 |
| 306.0 | 316.1 | * | 311.5 | 315.4 | −153.16 | 317.0 | 308.3 | * |
| 306.1 | 332.6 | 159.56 | 311.6 | 300.6 | * | 317.1 | 312.2 | 39.92 |
| 306.2 | 350.5 | 166.48 | 311.7 | 287.2 | −139.48 | 317.2 | 316.1 | 40.08 |
| 306.3 | 370.1 | 174.02 | 311.8 | 274.9 | −133.53 | 317.3 | 320.1 | 40.24 |
| 306.4 | 391.5 | 182.26 | 311.9 | 263.6 | −128.07 | 317.4 | 324.1 | 40.40 |
| 306.5 | 415.0 | 191.30 | 312.0 | 253.2 | −123.04 | 317.5 | 328.1 | 40.56 |
| 306.6 | 440.9 | 201.27 | 312.1 | 243.5 | −118.40 | 317.6 | 332.1 | 40.72 |
| 306.7 | 469.7 | 212.31 | 312.2 | 234.6 | −114.10 | 317.7 | 336.2 | 40.88 |
| 306.8 | 501.8 | 224.61 | 312.3 | 226.3 | −110.10 | 317.8 | 340.3 | 41.04 |
| 306.9 | 537.8 | 238.41 | 312.4 | 218.5 | −106.38 | 317.9 | 344.4 | 41.20 |

Based upon the above tables and figures, there is little sensitivity to pressure and altitude. Even though pressure appears in the ozone equation (see Equation 6, $y=m(Z)P/P_0$), very minimal error will be incurred by setting $P=P_0$. As a result, it was decided that this instrument would be developed initially with no pressure sensor. As improvements to accuracy approach the point of squeezing out the last percent error, then it will be worthwhile to include pressure as a variable.

The ozone equation is more sensitive to error in solar elevation angle. According to Table 14 (and FIG. 24), 1% error in elevation angle produces almost 1% error in calculated ozone. Therefore, the solar position equations should accurately predict the elevation angle. Comparison was done between the equations used in this instrument and the NOAA Solar Position Calculator (NOAA-SRRB 2005). The instrument equations produce an elevation angle that is typically within 0.5% of the more accurate NOAA equations used on their website, though errors have been noted as high as 1.5%.

Next, looking at sensitivity to extraterrestrial constants (Table 15, FIGS. 25-27) the ozone equation is fairly sensitive to these parameters, particularly $I_{o2}$. It is understandable that the equation is more sensitive to $I_{o2}$ since it appears in two ratios (see Equation 11). The way to minimize the error due to extraterrestrial constants is to perform the Langley calibration very carefully on a cloudless day that is free from particulate pollution. This is done at a point of high altitude far from metropolitan smog. Table 16 and FIG. 28-FIG. 30 show that the ozone result is extremely sensitive to wavelength. (Note: The nominal wavelengths used in the sensitivity analysis were the effective wavelengths calculated for the instrument calibration on Mar. 30, 2005.) There is greater than 100% change in calculated ozone for a 1% variation in either $\lambda 1$ or $\lambda 2$. This effect is due to the wavelength sensitivity of the ozone and Rayleigh attenuation constants (Equations 28 and 29). Again, the Langley plots are key to getting accurate results, but, in this case, it is also crucial to have a calibrated ozone meter at the same location where the instrument calibration is being done. Recall, Equation (36) relies on knowing total column ozone in order to calculate effective wavelengths. Collocation with a standard instrument such as Brewer or Dobson is the best way to obtain accurate local ozone readings and thereby minimize effective wavelength errors.

Calibration. The Langley method, which is a component of system calibration, has been discussed above, and is used in calculating the extraterrestrial constants as well as determining the effective wavelengths needed to calculate the ozone and Rayleigh attenuation constants. Though Langley data is collected automatically, the calibration process is not fully automated yet and the operator should copy the Langley data into a spreadsheet for regression analysis to determine the slopes and intercepts for the regression lines. The operator can also obtain the local ozone reading and solve Equation

(36) for effective wavelengths. Automating the calibration process is considered to be within the spirit and scope of this invention.

There are additional components of instrument calibration at the subsystem level such as spectrometer wavelength and intensity calibration and collimating lens adjustment. There are a five collimating lenses that may need to be adjusted in this system, considering the light collection lens and two filter holders, each containing two lenses.

Spectrometer Calibration. Prior to collecting any data, the spectrometer is calibrated for both wavelength and intensity using calibrated reference lamps. An HG-1 Mercury Argon Calibration Source from Ocean Optics is used for wavelength calibration. This light source generates a series of narrow band peaks (lines) which are displayed on the spectrometer. The mercury lines are the ones of interest, being in the UV/visible range. Calibration involves running a regression analysis of the spectrometer's pixel location for each of these light peaks. The equation being solved with the regression is $$\lambda_p = I + C_1 p + C_2 p^2 + C_3 p^3 \qquad (44)$$

where $\lambda$ is the wavelength of pixel p, I is the y-intercept and $C_1$, $C_2$, and $C_3$ are the third order polynomial coefficients (Ocean Optics 2000). This analysis is aided by the use of a spreadsheet program such as Microsoft Excel which provides analysis tools for performing polynomial curve fitting. Once the regression constants are obtained they are programmed into the spectrometer using the "Spectrometer/Configure" menu.

Spectrometer trace amplitude is calibrated using an LS-1-CAL Calibrated Light Source, also from Ocean Optics. The spectral intensity of the LS-1-CAL is traceable to a National Institute of Standards and Technology ("NIST") intensity standard. The LS-1-CAL is shipped with a disk containing the Lamp Calibration Reports for the specific calibration light source. The Ocean Optics spectrometer has built in software that reads this calibration data and then produces a linear 15th order polynomial regression which represents the spectral response of the system. This polynomial is stored in a file and used by the spectrometer to report and display trace magnitudes.

Collimating Lens Adjustment. Prior to collecting data for Langley plots, all of the collimating lenses in the system should be focused, particularly the light collection lens. Focusing involves attaching each lens via fiber optic to a light source such as the LS-1 (a the calibrated light source is not needed), shining the light onto a wall about 2 meters away, and then adjusting the barrel of the lens until the edge definition is crisp. Room lighting may need to be dimmed in order to clearly see the edge of the spot.

Each collimating lens is shipped from Ocean Optics with only one set screw. This seems to be OK for the collection lens, but, in order to minimize loss through the filter holders, an additional set screw was used for these lenses. The additional set screw was inserted in one of the three remaining holes after focusing the lens. The determination of where to place the set screw was made by aiming the light collection lens at the sun and then, while watching the signal amplitude on the spectrometer, trying a set screw (one at a time) in each of the three open locations. The one producing the greatest amplitude is the preferred location for the set screw. This is done for both input and output of each filter holder. This procedure provides better alignment of the input to output beam trough the filter holders by judiciously cocking the sliding barrel in each lens assembly against the inner wall of the lens tube. Using two set screws makes the input/output beam alignment far more robust against vibration and other unintended movement of the fiber optic cables.

Frequency of Calibration. The UNT ozone results reported for the six month period Mar. 30, 2005 through Oct. 4, 2005 used the Langley calibration performed on Mar. 30, 2005. Referring back to FIG. 21 ("Comparison of TOMS and UNT") and the RMS percent error (Table 12), the calibration performed on Mar. 30, 2005 has yielded accurate results for the six month period shown. Data collection is continuing, using this calibration. At this time, based upon available data, the supported calibration frequency is every six months, but it is suspected that an annual calibration will suffice.

While overall system calibration is useful, it should not be necessary to recalibrate the spectrometer and lenses as often. Absolute amplitude calibration of the spectrometer is not critical due to the fact that extraterrestrial intensities are unit-less digital numbers determined from Langley plots. No absolute amplitude scale is needed since ozone is calculated by intensity (digital number) ratio. Also, because the ozone equation uses ratios of intensities, any amplitude drift that is common mode, will cancel out. However, any relative drift of the spectrometer amplitude between different wavelengths may affect ozone accuracy. This can be compensated by a new system level calibration (e.g. new Langley data), but the spectrometer intensity accuracy should be checked at every other system calibration event prior to the system calibration. If there is more than a few percent error in spectrometer intensity, then it should be recalibrated first.

Spectrometer wavelength calibration is useful in order to allow selective collection of intensity data for the precise wavelengths needed to measure ozone. Small initial spectrometer calibration errors (on the order of 0.25 nm) are tolerable due to the system level calculation of effective wavelengths based upon Langley data. However, any drift of spectrometer wavelength calibration with time affects the ozone accuracy, as demonstrated by the above sensitivity analysis. The spectrometer wavelength accuracy should be checked prior to every system calibration to verify its stability. If variation of more than 0.05 nm is observed since the last calibration, then the accuracy of the recent ozone data should be reevaluated and the spectrometer should be monitored more closely for wavelength drift in the future.

In general, the spectrometer wavelength accuracy should be checked prior to every system calibration and the intensity accuracy should be checked at every other system calibration event. Once the lenses are adjusted, they should not need additional adjustment, unless the set screws are loosened for some reason.

The apparatus and method described above has demonstrated that stratospheric ozone can be measured cost effectively, with reasonable accuracy, using a fiber optic spectrometer coupled with fiber optic cables, narrow FOV lenses, and optical bandpass filters. The overall relative error calculated above was about ±3.2% with maximum error of about +4.8% and −7.7%. Thus, it has been demonstrated that a fiber optic spectrometer system for ozone measurement can be automated in an inexpensive manner. An off-the-shelf stepper motor driven pan and tilt (PT) unit was employed as a positioning system for aiming the lenses and "freeware" scripting software was used to develop overall system control programs. A pan and tilt positioning system is readily suited to this application, since the solar position calculation equations yield azimuth and elevation angles, which map directly to pan and tilt coordinates, respectively. The resolution of the chosen PT and its RS-232 interface allow fully automated closed loop aiming of the collection lenses, using the 330 nm light intensity from the spectrometer as feedback.

The apparatus described above can be built inexpensively using the following items, as described in 2005 U.S. dollars:

| Item Description | | Approx. Cost |
|---|---|---|
| Dual channel spectrometer - Ocean Optics SD200 | | 2,600 |
| 10 um slit - Ocean Optics SLIT-10 | | 150 |
| Solar blind filter - Carion SB-300-F | | 350 |
| Schott glass filter - Melles Griot UG11 | | 155 |
| Filter holder (x2) - Ocean Optics FHS-UV | 400 × 2 = | 800 |
| Fiber optic cable - Ocean Optics (200 um × 20 m) | | 350 |
| Fiber optic cable (x2) - Ocean Optics (200 um × 1 m) | 100 × 2 = | 200 |
| Pan & Tilt (PT) unit - Directed Perception PTU-46-17.5 | | 2,000 |
| PT 20 degree bracket | | 15 |
| 12 V power supply for PT unit | | 40 |
| 12 V power cable for PT unit (20 m) | | 10 |
| Weatherproof enclosure for motor driver (6" × 8") | | 15 |
| RS-232 cable (20 m) | | 15 |
| PC - 500 MHz+ (assume old PC is available - no cost) | | 0 |
| Domed enclosure to cover PT and lenses | | 250 |
| | Total | $6,950 |

Additionally

The Calculation/Control Program script for reading ozone using (QUICK BASIC Version 4.5) could be determined by one of ordinary skill in the art using the above description for guidance. Similarly, the script program for measuring ozone Automatic closed loop aiming enables this instrument to function for its intended purpose and allows an easy setup. However, without closed loop positioning, the PT would require very accurate leveling both front to back and side to side. Rotational mounting accuracy is not as critical, since program offsets for the pan axis are used to compensate. Even with a perfectly level PT, the open loop positional accuracy of the PT may not be adequate for all possible solar angles. While the PT used in this system has excellent resolution for this task, its open loop accuracy is not specified, by closing the loop using spectrometer feedback, resolution becomes useful and the PT accuracy is not a critical concern. A further advantage is accrued by closing the loop on the positioning system; the required accuracy of the solar position equations is relaxed. Without the aid of intensity feedback from the spectrometer, more accurate calculation of the azimuth and elevation angles are needed to center the sun within the collection lens field of view.

An inherent advantage afforded this instrument due to utilizing a spectrometer with a CCD array to capture light intensity data, as compared to using multiple light sensing diodes like in the MICROTOPS II. As discussed, the equation used to calculate ozone employs ratios of intensities at different wavelengths. Therefore, if the gain of one sensor drifts relative to another, error is injected directly into the calculated ozone value. Having three independent light sensing diodes, MICROTOPS II is subject to this type of error. By using a CCD to capture intensity data, one single substrate contains all of the sensing elements and any drift is likely to be shared by all elements and this common mode drift will cancel out in the ratio. Calculated ozone is therefore not affected as long as the gains of all elements drift equally.

Example 2

The Apparatus and method described in Example 1 can be used with simultaneous (single scan) collection of intensity data for all three wavelengths that can yield an improvement in accuracy. In order to implement this single scan feature, the light intensity for the longer wavelengths should be attenuated such that, at solar noon, the spectral intensity plot is nearly flat for all wavelengths in the range of interest. Shaping the spectral curve in this way may require a custom designed filter, with a transmittance curve shaped roughly as the inverse of the solar intensity spectrum. For example, the solar blind filter could be retained, and the Schott UG-11 could be replace, with the goal being that the combined transmittance of both filters yields roughly a flat intensity plot for the 300-330 nm range.

Example 3

The Apparatus and methods described in Examples 1 and 2, could also utilized components and methods for transmitting more light into the spectrometer. This is desirable to reduce the integration time (particularly for the 305.5 nm wavelength) and further limit error due to optical density variation of the atmosphere. Transmission of more light coupled with the single scan of Example 2 would also open the door to multiple scan averaging without re-aiming the lenses.

There are several ways to get more light into the spectrometer. For example, a larger spectrometer entrance slit (25 μm) would enable a reduction in integration times for all wavelengths by a factor of about 2.5. However, this option trades off spectrometer wavelength resolution. Increasing the slit width to 25 μm worsens the spectrometer FWHM resolution from 0.234 nm to 0.308 nm.

Another approach to increasing light intensity in the spectrometer is to use a larger fiber optic diameter. Increasing the diameter of the fiber optic from 200 μm to 400 μm, with an about 10 μm entrance slit, approximately doubles the light striking the spectrometer grating. This allows the integration time to be cut almost in half.

A further method for increasing light throughput to the spectrometer is the installation of an L2 lens or equivalent thereof from what Ocean Optics. This lens can be installed in the spectrometer, at the factory, and serves to focus the light beam such that more light passes through the slit and hits the grating. Use of an L2 lens provides almost four times the light intensity at the grating when using a 10 μm slit and 200 μm fiber optic. Therefore, reduction by a factor of approximately four can be expected for integration time.

By implementing both the single scan and increased light intensity enhancements, multiple scan averaging could be implemented in place of boxcar averaging. This would enable the instrument to regain the spectrometer resolution which was given up to perform boxcar averaging while at the same time maintain the S/N improvement afforded by averaging. Better wavelength resolution should result in more consistent readings for a wider range of airmass values.

By collecting all wavelengths in a single scan and increasing light intensity to reduce integration time, multiple scans (replicates) could be made without re-aiming the lenses. Ozone could be calculated for each of these replicates and then averaged. Actually, the same robust averaging technique which is employed currently in this instrument could be used to average the replicates. This replicate average is to be considered a single ozone reading. After an ozone reading is done, the system would re-aim the lenses and collect and average another set of replicates, producing the second ozone reading, and so on. After ten ozone values are obtained in this manner, they would be further processed using the exact algorithm of the present instrument. The result is a multi-level average which improves spectrometer S/N as well as reducing the effects of other system noise sources.

Additional instrument accuracy may be acquired through the use of higher precision equations for calculating the solar elevation angle. The ozone result varies by almost 1% per 1% change in elevation angle. Any improvement in the equations which calculate elevation angle therefore have a direct, almost one-to-one, effect on ozone accuracy. As mentioned in the section on sensitivity, the solar position equations were checked against the more accurate NOAA equations. The elevation angle computed by the instrument equations was typically within 0.5% of the more precise equations, but the error was observed to be as high as 1.5%. Therefore, more accurate solar position equations should be a rather high priority when making future enhancements to the instrument.

The inclusion of measuring local barometric pressure and including this variable in the ozone calculation can also improve accuracy. As shown in the sensitivity analysis, the ozone equation is not very sensitive to pressure, only about 0.03% change in ozone per 1% change in barometric pressure. Barometric pressure typically varies less than a percent, which results in only a slight improvement if this indicator is used.

Example 4

The apparatus and methods described in Examples 1, 2 and 3 could also include an increased in the fiber optic diameter and then splitting the light into three beams which are then fed into three separate spectrometer channels. Attenuators could be used in the longer wavelength channels to match their intensities to the shorter wavelength channel. Simultaneous scans could then be made, drastically reducing the effects of sky variability. The existing bandpass filter would still be used to remove high intensity longer wavelengths prior to the three way splitter Example 5

The apparatus and methods described in Examples 1, 2, 3 and 4 that is equipped with a high resolution fiber optic spectrometer and precision remote controlled aiming device, is a flexible platform with potential to study various atmospheric constituents in addition to total column ozone. Applications exist in a variety of ecosystems and air quality studies. As stated above, both UV/visible and visible/IR channels are present in the spectrometer along with the accompanying optics. The high resolution of the spectrometer allows good discrimination between many wavelengths (a total of 4096). The spectrometer-based Brewer instrument presently measures $SO_2$ and $NO_x$, and it is therefore expected that concentrations of these pollutants are discernable within the spectral bands of this new instrument. Beyond $SO_2$, $NO_x$, and other pollutants, haze measurement would be a natural addition. Haze data gives a quantitative local indicator of overall visibility and air clarity. Once calibrated, haze measurements could be made directly using the visible spectra. This instrument can be programmed and calibrated to compute the UV exposure index by integrating UV-B spectral data. Thus, this one instrument platform can report total column ozone, UV exposure index, haze, and other atmospheric constituents.

One skilled in the art readily appreciates that this invention is well adapted to carry out the objectives and obtain the ends and advantages mentioned as well as those inherent therein. Thus, it should be evident that the apparatus and method of this invention is related to an instrument that employs a high-resolution fiber-optic spectrometer, coupled with precisely aimed fiber optics to acquire intensity data at multiple UV wavelengths within the UV-B range (280-320 nm), and variations of the components, and methods are encompassed by the invention. For example, software, hardware, or method steps may change as manufacturing of these devices are needed, such industrial scaling of production are understood to be within the spirit of the invention. The components, methods, procedures and techniques described herein are presently representative of the preferred embodiments and are intended to be exemplary and are not intended as limitations of the scope. As such, changes therein and other uses will occur to those skilled in the art which are encompassed within the spirit of the invention or defined by the scope of the pending claims.

REFERENCES CITED

The following references, to the extent that they provide exemplary procedural or other details supplementary to those set forth herein, are specifically incorporated herein by reference.

U.S. Patent Documents

U.S. Pat. No. 4,441,815, issued to Izumi on Apr. 10, 1984 and titled "Self-Modulating Spectrometer."
U.S. Pat. No. 4,652,761 issued to Kerr, et al., on Mar. 24, 1987, and titled "Grating Ozone Spectrophotometer."

References

Acevedo, M. F. 2004. *Simulation of Ecological and Environmental Models*. Denton, Tex.: University of North Texas.
Andrady, A. L., Hamid, S. H., Hu, X., and Torikai, A. 1998. Effects of increased solar ultraviolet radiation on materials. *J. Photochem. Photobiol.* 46:96-103.
ARIC-DEFRA, Ozone Depletion Fact Sheet Series for Key Stage 4 and A-level. Web site accessed 2005. http://www.ace.mmu.ac.uk/Resources/Fact_Sheets/Key_Stage__4/Ozone_Depletion/index.html
Bigelow D. S., J. R. Slusser, A. F. Beaubien, J. H. Gibson. 1998. The USDA ultraviolet radiation monitoring program. *Bull. Am. Meteor. Soc.* 79:601-615.
Bojkov R. D. and V. E. Fioletov. 1995. Estimating the global ozone characteristics during the last 30 years. *J. Geophys. Res.* 100:16 537-551.
Bramstedt K, J. Gleason, D. Loyola, W. Thomas, A. Bracher, M. Weber, and J. P. Burrows. 2002. Comparison of total ozone from the satellite instruments GOME and TOMS with measurements from the Dobson network 1996.2000. *Atmos. Chem. Phys. Discuss.* 2:1131.1157.
Caldwell, M. M., Bjorn, L. O., Bomman, J. F., Flint, S. D., Kulandaivelu, G., Teramura, A H., and Tevini, M. 1998. Effects of increased solar ultraviolet radiation on terrestrial ecosystems, *J. Photochem. Photobiol.* 46:40-52.
Enger, E. D. and Smith, B. F. 2002. *Environmental Science A Study of Interrelationships*. New York, N.Y.: McGraw-Hill.
Farman, J. C., Gardiner, B. G. and Shanklin, J. D. 1985. Large losses of total ozone in Antarctica reveal seasonal ClOx/NOx interaction. *Nature* 315:207-210
Fellers, T. J. and Davidson, M. W. 2005. Optical Microscopy Primer: Digital Imaging in Optical Microscopy. *Molecular Expressions*. Web site accessed in 2005. http://micro.magnet.fsu.edu/primer/digitalimaging/concepts/ccdsnr.html
Gao W., Z. Youfey, J. R. Slusser, Y. He, Z. Ronggang. 2003. Impact of enhanced ultraviolet. B irradiance on maize yield formation and structure: a field evaluation. Proceedings of the SPIE, *Ultraviolet ground and space based measurements, models and Effects III* 396-402.

González R., R. Mepsted, A. R. Wellburn and N. D. Paul. 1998. Non-photosynthetic mechanisms of growth reduction in pea (*Pisum sativum* L.) exposed to UV-B radiation. *Plant, Cell and Environment* 21:23-32.

Häder, D. P., Kumar, H. D. Smith, R. C. and Worrest, R. C. 1998. Effects on aquatic ecosystems. *J. Photochem. Photobiol.* 46:53-68.

Hall, C. W. 2000. *Laws and Models: Science, Engineering, and Technology*. Boca Raton, Fla.: CRC Press LLC.

Hartwig, M. 1994. Ultraviolet and Your Health. *Currents in Science, Technology & Society* 3:11-12, 16.

Huber, P. J. 1981. *Robust Statistics*. New York, N.Y.: John Wiley & Sons

Kaufman, Y. J., Dubovik, O., Smirnov, A. Holben, B. N. 2002. Remote Sensing of Non-aerosol Absorption in Cloud Free Atmosphere. Geoph. Res. Lett., 29(18):1857.

Köhler, U. 1999. A Comparison of the New Filter Ozonometer MICROTOPS II with Dobson and Brewer Spectrometers at Hohenpeissenberg. *Geophysical Research Letters* 26(10):1385-1388

Midgley G. F., S. J. E. Wand and C. F. Musil. 1998. Repeated exposure to enhanced UV-B radiation in successive generations increases developmental instability (leaf fluctuating asymmetry) in a desert annual. *Plant, Cell and Environment* 21:437-442.

Miller, G. T. 2001. *Environmental Science: Working with the Earth*. Pacific Grove, Calif.: Brooks/Cole Molina, L. T., Molina, M. J. 1986. Absolute Absorption Cross Sections of Ozone in the 185- to 350-nm Wavelength Range. *J. Geophys. Res.* 91(D13): 14501-14508.

Morys, M., F. M. Mims III, and S. E. Anderson. 1996. Design, calibration and performance of MICROTOPS II hand-held ozonometer. $12_{th}$ International Symposium on Photobiology, Vienna, Austria.

NASA-TOMS 2005. Earth Probe TOMS Instrument and Satellite Information. Web site accessed 2005. http://toms.gsfc.nasa.gov/eptoms/epsat.html NASA-GSFC 2003. Stratospheric Ozone An Electronic Textbook. Web site released 2003. Accessed 2005. http://www.ccpo.odu.edu/SEES/ozone/oz_class.htm National Research Council 1993: *Protecting Visibility in National Parks and Wilderness Areas*. Washington, D.C.: National Academy Press Nebgen, G., B. "AUTOMATED LOW COST INSTRUMENT FOR MEASURING TOTAL COLUMN OZONE," Dissertation, University of North Texas, Denton, Tex. (Available to the public after May 2006).

NOAA 2004a. U.S. Global Change Research Program. Interagency program on Ultraviolet radiation. Web site accessed 2004. http://www.arl.noaa.gov/research/programs/uv.html)

NOAA 2004b. Stratospheric Ozone: Monitoring and research in NOAA. Web site accessed 2004. http://www.ozonelayer.noaa.gov/

NOAA-CMDL 2004. CMDL Total Ozone. Web site accessed 2004. http://www.cmdl.noaa.gov/ozwv/dobson/

NOAA-NWS-CPC 2004. Stratosphere: UV Index. Web Site. Accessed 2004. http://www.cpc.ncep.noaa.gov/products/stratosphere/uv_index/

NOAA-SRRB 2005a. Central UV Cal Facility and UV Information & Monitoring pages. Web site accessed 2005. http://www.srrb.noaa.gov/

NOAA-SRRB 2005b. General Solar Position Calculations. Web site accessed 2005. http://www.srrb.noaa.gov/highlights/sunrise/solareqns.PDF NSF 2004. National Science Foundation. Polar programs UV Monitoring Network. Web Site accessed 2004. http://www.biospherical.com/nsf/Ocean Optics 2000. *Operating Manual and User's Guide S2000 Miniature Fiber Optic Spectrometers and Accessories*. Dunedin, Fla.: Ocean Optics Inc.

Penndorf, R. 1957. Table of the Refractive Index for Standard Air and the Rayleigh Scattering Coefficient for the Spectral Region between 0.2 and 20.0µ ant Their Application to Atmospheric Optics, *J. Opt. Soc. Amer.* 47(2): 176-182.

PHOTOMET 2005. Photometrics: Encyclopedia (Binning, Signal-to-Noise-Ratio). Web site accessed 2005. http://www.photomet.com/library_encyclopedia.shtml Santee, M. L., W. G. Read, J. W. Waters, L. Froidevaux, G. L. Manney, D. A. Flower, R. F. Jarnot, R. S. Harwood, and G. E. Peckham. 1995. Interhemispheric differences in polar stratospheric $HNO_3$, $H_2O$, ClO and $O_3$. *Science* 267-849-853.

Slusser, J. R., J. H. Gibson, D. S. Bigelow, D. Kolinski, P. Disterhoft, K. Lantz and A. Beaubien. 2000. Langley Method of Calibrating UV Filter Radiometers, *J. Geophys. Res.* 105: 4841-4849.

Ullrich, S. E. 2002. Photoimmune suppression and photocarcinogenesis. *Frontiers in BioScience* 7:d684-703.

USDA 2004. UV-B Monitoring and Research Program. Web Site accessed 2004. http://uvb.nrel.colostate.edu/UVB/home_page.html USEPA 2004. Ultraviolet Monitoring Program: UV-Net Web site accessed 2004. http://www.epa.gov/uvnet/

USEPA 2005. The Effects of Ozone Depletion. Web site accessed 2005. http:www.epa.gov/ozone/science/effects.html Varotsos, C., Tzannis, C., Christodoulakis, J. 2002. Contribution of the Athens University to Envisat Intercomparison of the Total Ozone Observations at Athens, Greece. *Proc. of Envisat Validation Workshop*, Frascati, Italy, December 2002 (ESA SP-531, August 2003)

WMO-UNEP 2002. Scientific Assessment of Ozone Depletion: 2002. World Meteorological Organization.

What is claimed:

1. An apparatus for measuring ozone in the atmosphere, comprising:

(a) a fiber optic cable having a first end and a second end;

(b) a collimating lens having narrow field of view coupled to the first end of the fiber optic cable, wherein light from a Sun is capable of being funneled into the fiber-optic medium and is transmitted through the fiber optic cable, wherein the narrow field of view is in the range of from about 1° to about 45°;

(c) a spectrometer having a ultra-violet/visible light ("UV/VIS") channel coupled to the second end of the fiber optic cable; (d) an optical bandpass filter coupled to the fiber optic cable; and (e) a pan-and-tilt positioning unit having a pan-axis capable of tracking an azimuth angle of the Sun, and a tilt-axis capable of tracking an elevation angle of the Sun, wherein pan-and-tilt positioning unit further comprises a means for mounting the collimating lens.

2. The apparatus of claim 1, further comprising: a computer in electrical communication with the spectrometer and the pan-and-tilt unit, wherein the pan-axis and the tilt-axis is controlled by the computer using software through a RS232 interface.

3. The apparatus of claim 2, further comprising, a software architecture that utilizes a script; a mechanism control and calculation algorithm; file storage device; and the spectrometer for communicating instructions and data, wherein the script communicates information to the mechanism control and calculation algorithm, and the spectrometer; the spectrometer communicates information to the file storage device; the mechanism control and calculation algorithm communicates information to the file storage device; and the file storage device communicates information to the script and to the mechanism control and calculation algorithm.

4. The apparatus of claim 1, further comprising: a second fiber optic cable having a first end and a second end; a second collimating lens having narrow field of view coupled to the first end of the second fiber optic cable; and the spectrometer having a second channel for tracking a visible-light/near infra-red ("VIS/NIR") spectrum that is coupled to the second end of the second fiber optic cable.

5. The apparatus of claim 4, wherein the first and second collimating lenses have a narrow field of view comprising about 2.5°.

6. The apparatus of claim 1, wherein the fiber optic cable connects the collimating lens and the spectrometer through a barrier that separates an outdoor place from an indoor place.

7. The apparatus of claim 1, wherein the fiber optic cable comprises a diameter of about 200 μm and a length up to about 20 meters.

8. The apparatus of claim 1, wherein the bandpass filter comprises a two-stage optical bandpass filter capable of filtering wavelengths of light that are outside the range of about 260 nm to about 340 nm.

9. The apparatus of claim 1, wherein the spectrometer comprises a grating having 1800 lines for detecting UV/VIS in a range of about 200-350 nm; a 2048-element linear CCD array detector; a 10 um entrance slit; and optical resolution of 0.234 nm full width at half maximum ("FWHM").

10. The apparatus of claim 1, wherein the pan-and-tilt positioning unit comprises a stepper motor driven mechanism capable of a 360° pan axis rotation with the tilt axis range being about 111° with a resolution of about 0.051° per half-step for each axis that corresponds to about 49 steps across an about 2.5° lens field of view.

11. The apparatus of claim 1, wherein the means for mounting the collimating lens comprises an aluminum bracket having a bend angle of about 20°.

12. A method for measuring ozone in the atmosphere, comprising:
(a) initializing an outdoor pan-and-tilt positioning unit having a pan-axis capable of tracking an azimuth angle of a Sun, and a tilt-axis capable of tracking an elevation angle of the Sun, wherein the outdoor pan-and-tilt positioning unit comprises a mounted collimating lens that is coupled to an indoor spectrometer through a fiber optic cable, and the outdoor pan-and-tilt positioning unit is in electrical communication with a computer capable of controlling the pan-axis and the tilt-axis using software through an interface;
(b) using the software for calculating the azimuth angle of the Sun and the elevation of the Sun for a date, time, and location, creating a calculated azimuth angle and a calculated elevation angle of the Sun;
(c) pointing the mounted collimating lens toward the Sun by controlling the pan-axis and the tilt-axis with the computer using software through the interface, wherein mounted collimating lens is pointed toward the calculated azimuth angle and the calculated elevation angle of the Sun,
(d) fine-positioning the collimating lens toward the Sun by programming a series of fine movements of the pan-axis and the tilt-axis until the light intensity striking the collimating lens has a maximum signal of about 330 nm for a filtered spectrum of sunlight having a range of about 260-340 nm;
(e) gathering spectrometer data for calculating column ozone base upon Lambert-Beer- Bouguer Law, and calculating column ozone, forming a calculated column ozone value;
(f) averaging the calculated column ozone value for each time step (e) is completed, forming an average column ozone value;
(g) repeating step (b) at least once before proceeding to step (h); and
(h) recording the average column ozone value.

13. The method of claim 12, further comprising, selecting a software architecture that utilizes a script; a mechanism control and calculation algorithm; file storage device; and the spectrometer for communicating instructions and data, wherein the script communicates information to the mechanism control and calculation algorithm, and the spectrometer; the spectrometer communicates information to the file storage device; the mechanism control and calculation algorithm communicates information to the file storage device; and the file storage device communicates information to the script and to the mechanism control and calculation algorithm.

14. The method of claim 12, further comprising, selecting the collimating lens to have a narrow field of view comprising about 2.5°.

15. The method of claim 12, further comprising, selecting the fiber optic cable to comprises a diameter of about 200 μm and a length up to about 20 meter.

16. The method of claim 12, further comprising, selecting a two-stage optical bandpass filter capable of filtering wavelengths of light that are outside the range of about 260 nm to about 340 nm, wherein the optical bandpass filter is installed and coupled to the fiber optic cable interposing the collimating lens and the spectrometer.

17. The method of claim 12, further comprising, selecting the spectrometer having a grating with 1800 lines for detecting UV/VIS in a range of about 200-350 nm; a 2048-element linear CCD array detector; a 10 um entrance slit; and optical resolution of 0.234 nm full width at half maximum ("FWHM").

18. The method of claim 12, further comprising, selecting the pan-and-tilt positioning unit having a stepper motor driven mechanism capable of a 360° pan axis rotation with the tilt axis range being about 111° with a resolution of about 0.051° per half-step for each axis that corresponds to about 49 steps across an about 2.5° lens field of view.

19. The method of claim 12, further comprising, selecting the means for mounting the collimating lens to be an aluminum bracket having a bend angle of about 20°.

20. The method of claim 12, further comprising, selecting a closed loop positioning algorithm for determining the series of fine movements used until the light intensity striking the collimating lens has the maximum signal of about 330 nm for a filtered spectrum of sunlight.

21. The method of claim 12, further comprising, selecting the computer for recording the average column ozone value.

* * * * *